(12) United States Patent
Szpak et al.

(10) Patent No.: US 11,833,517 B2
(45) Date of Patent: Dec. 5, 2023

(54) WATER TESTING SYSTEMS AND DEVICES

(71) Applicant: Sundance Spas, Inc., Chino, CA (US)

(72) Inventors: James Edward Szpak, Cleveland Heights, OH (US); Sergey V. Makarov, Solon, OH (US); Benjamin Philip Parker, Chardon, OH (US); Robert Craig Allen, Richmond Heights, OH (US)

(73) Assignee: Sundance Spas, Inc., Chino, CA (US)

( * ) Notice: Subject to any disclaimer, the term of this patent is extended or adjusted under 35 U.S.C. 154(b) by 517 days.

(21) Appl. No.: 17/097,153

(22) Filed: Nov. 13, 2020

(65) Prior Publication Data

US 2021/0146367 A1 May 20, 2021

Related U.S. Application Data

(60) Provisional application No. 62/936,009, filed on Nov. 15, 2019.

(51) Int. Cl.
*B01L 3/00* (2006.01)
*A61H 33/00* (2006.01)

(52) U.S. Cl.
CPC .......... *B01L 3/527* (2013.01); *A61H 33/0087* (2013.01); *B01L 2200/0689* (2013.01); *B01L 2300/0663* (2013.01); *B01L 2300/0681* (2013.01); *B01L 2300/1894* (2013.01); *B01L 2400/0475* (2013.01); *B01L 2400/0633* (2013.01)

(58) Field of Classification Search
CPC ............. B01L 3/527; B01L 2300/0663; B01L 2300/0681; G01N 33/18; G01N 21/78; G01N 21/77; G01N 21/80; G01N 2001/2064
See application file for complete search history.

(56) References Cited

U.S. PATENT DOCUMENTS

| | | |
|---|---|---|
| 4,217,331 A | 8/1980 | Schaub |
| 4,917,868 A | 4/1990 | Alexander et al. |

(Continued)

FOREIGN PATENT DOCUMENTS

| | | |
|---|---|---|
| FR | 2656006 A1 | 6/1991 |
| FR | 2704872 A1 | 11/1994 |

(Continued)

*Primary Examiner* — Lore R Jarrett
(74) *Attorney, Agent, or Firm* — THE WEBB LAW FIRM

(57) ABSTRACT

A spa tub includes a spa shell configured to contain a volume of water; a circulation system configured to create a flow of the water to and from the spa shell; and a testing system configured to acquire water samples from the volume of water and to perform water quality tests on the water samples. The testing system includes a housing; a circulation pump disposed within the housing configured to acquire the water samples from the volume of water; a replaceable reagent cartridge removably received within the housing; and a water test assembly disposed within the housing. The water test assembly is configured to receive the water samples acquired by the circulation pump and a reagent from the reagent cartridge. The water test assembly is configured to mix the water samples and the reagent and to perform the water quality tests on the mixed water samples and reagent.

20 Claims, 26 Drawing Sheets

(56) References Cited

U.S. PATENT DOCUMENTS

| | | | |
|---|---|---|---|
| 4,979,245 A | 12/1990 | Gandini | |
| 4,997,540 A | 3/1991 | Howlett | |
| 5,012,535 A | 5/1991 | Klotzbach | |
| 5,374,356 A | 12/1994 | Miller et al. | |
| 5,383,239 A | 1/1995 | Mathis et al. | |
| 5,587,023 A | 12/1996 | Booth | |
| 5,801,516 A | 9/1998 | Rice et al. | |
| 5,862,545 A | 1/1999 | Mathis et al. | |
| 5,882,602 A * | 3/1999 | Savage | B01L 3/0293 422/537 |
| 5,985,155 A | 11/1999 | Maitland | |
| 6,255,117 B1 | 7/2001 | Johnson | |
| 6,309,538 B1 | 10/2001 | Khan | |
| 6,332,972 B1 | 12/2001 | Orolin et al. | |
| 6,340,431 B2 | 1/2002 | Khan | |
| 6,509,551 B2 | 1/2003 | Metcalfe et al. | |
| 6,673,248 B2 | 1/2004 | Chowdhury | |
| 6,751,814 B2 | 6/2004 | Mattson, Jr. et al. | |
| 6,913,684 B1 | 7/2005 | Barak et al. | |
| 6,920,653 B2 | 7/2005 | Selover | |
| 6,942,790 B1 | 9/2005 | Dolton | |
| 6,944,893 B1 | 9/2005 | Mattson, Jr. et al. | |
| 6,948,510 B2 | 9/2005 | King | |
| 6,992,488 B2 | 1/2006 | Lin | |
| 7,167,087 B2 | 1/2007 | Corrington et al. | |
| 7,243,379 B2 | 7/2007 | Panopoulos | |
| 7,258,783 B2 | 8/2007 | Harbol | |
| 7,306,660 B2 | 12/2007 | Seto et al. | |
| 7,347,934 B2 | 3/2008 | King et al. | |
| 7,347,935 B2 | 3/2008 | King | |
| 7,488,415 B2 | 2/2009 | Hui et al. | |
| 7,489,986 B1 | 2/2009 | Laflamme et al. | |
| 7,736,523 B2 | 6/2010 | King | |
| 7,752,893 B2 | 7/2010 | Biberger | |
| 7,767,067 B2 | 8/2010 | Silveri | |
| 7,883,622 B1 | 2/2011 | Barnes | |
| 7,982,625 B2 | 7/2011 | Brochu et al. | |
| 8,002,978 B2 | 8/2011 | King | |
| 8,021,545 B2 | 9/2011 | Schuster et al. | |
| 8,133,398 B2 | 3/2012 | King et al. | |
| 8,164,470 B2 | 4/2012 | Brochu et al. | |
| 8,459,100 B2 | 6/2013 | Biberger | |
| 8,464,743 B2 | 6/2013 | King et al. | |
| 8,480,373 B2 | 7/2013 | Stiles, Jr. et al. | |
| 8,545,682 B2 | 10/2013 | Jones et al. | |
| 8,566,972 B2 | 10/2013 | Vogtner et al. | |
| 8,624,749 B2 | 1/2014 | Brochu et al. | |
| 8,646,759 B2 | 2/2014 | Cunningham et al. | |
| 8,680,983 B2 | 3/2014 | Ebrom et al. | |
| 8,987,000 B2 | 3/2015 | Evtodienko et al. | |
| 8,993,337 B2 | 3/2015 | Evtodienko et al. | |
| 9,034,193 B2 | 5/2015 | Shalon | |
| 9,285,790 B2 | 3/2016 | Pruchniewski et al. | |
| 9,452,393 B2 | 9/2016 | King et al. | |
| 9,475,011 B2 | 10/2016 | Cunningham et al. | |
| 9,493,369 B2 | 11/2016 | McCague | |
| 9,732,765 B2 | 8/2017 | Surowinski et al. | |
| 9,776,888 B1 | 10/2017 | Kurani et al. | |
| 9,834,451 B2 | 12/2017 | Miller et al. | |
| 9,982,451 B2 | 5/2018 | McMurphy | |
| 10,047,535 B2 | 8/2018 | King et al. | |
| 10,060,148 B2 | 8/2018 | King et al. | |
| 10,098,823 B2 | 10/2018 | Cohen | |
| 10,119,287 B2 | 11/2018 | King et al. | |
| 10,123,539 B2 | 11/2018 | King et al. | |
| 10,150,680 B1 | 12/2018 | Kurani et al. | |
| 10,286,365 B2 | 5/2019 | Guy et al. | |
| 10,287,180 B1 * | 5/2019 | Kurani | C02F 1/66 |
| 10,444,208 B2 | 10/2019 | Chung et al. | |
| 10,577,256 B1 | 3/2020 | Kurani et al. | |
| 10,604,954 B2 | 3/2020 | Shalon et al. | |
| 2002/0148911 A1 | 10/2002 | Beck et al. | |
| 2003/0147777 A1 | 8/2003 | Ghanekar | |
| 2003/0147932 A1 | 8/2003 | Nun et al. | |
| 2003/0150796 A1 | 8/2003 | Heinig, Jr. | |
| 2005/0039795 A1 | 2/2005 | King | |
| 2005/0044619 A1 | 3/2005 | Mattson, Jr. et al. | |
| 2005/0097666 A1 | 5/2005 | Christensen | |
| 2005/0211612 A1 | 9/2005 | Mattson, Jr. et al. | |
| 2005/0263459 A1 | 12/2005 | Bowers | |
| 2006/0090251 A1 | 5/2006 | Harbol | |
| 2008/0093225 A1 | 4/2008 | Cline et al. | |
| 2008/0264447 A1 | 10/2008 | Eyal | |
| 2008/0268009 A1 | 10/2008 | Schuster et al. | |
| 2009/0176314 A1 * | 7/2009 | Steinboeck | B01L 3/502 422/400 |
| 2009/0220559 A1 | 9/2009 | Feldman et al. | |
| 2009/0266753 A1 | 10/2009 | Johnson et al. | |
| 2009/0317312 A1 | 12/2009 | Mikuski et al. | |
| 2010/0072119 A1 | 3/2010 | Wyatt, Jr. | |
| 2011/0195664 A1 | 8/2011 | Keirstead et al. | |
| 2012/0103919 A1 | 5/2012 | McCague | |
| 2015/0211043 A1 * | 7/2015 | Ram | C12Q 1/04 435/288.7 |
| 2015/0218835 A1 | 8/2015 | Shalon | |
| 2015/0329383 A1 * | 11/2015 | Mehl | C02F 1/24 204/240 |
| 2017/0029304 A1 | 2/2017 | Teichberg | |
| 2017/0092096 A1 | 3/2017 | Fernandes et al. | |
| 2017/0153217 A1 | 6/2017 | Johnston | |
| 2017/0209338 A1 | 7/2017 | Potucek et al. | |
| 2017/0284115 A1 | 10/2017 | Rejniak et al. | |
| 2017/0356209 A1 | 12/2017 | He et al. | |
| 2018/0229919 A1 | 8/2018 | King et al. | |
| 2018/0237320 A1 | 8/2018 | King | |
| 2018/0245272 A1 | 8/2018 | Bocchino et al. | |
| 2018/0273404 A1 | 9/2018 | Denkewicz, Jr. et al. | |
| 2019/0194046 A1 | 6/2019 | Sweeney | |

FOREIGN PATENT DOCUMENTS

| | | |
|---|---|---|
| JP | H04300552 A | 10/1992 |
| KR | 200333575 Y | 11/2003 |
| NZ | 233010 A | 1/1992 |
| WO | 2016087874 A1 | 6/2016 |
| WO | 2016176169 A1 | 11/2016 |

* cited by examiner

WATER TESTING SYSTEMS AND DEVICES

CROSS REFERENCE TO RELATED APPLICATION

This application claims priority to U.S. Provisional Patent Application No. 62/936,009, entitled "Water Testing System," filed Nov. 15, 2019, the disclosure of which is hereby incorporated by reference in its entirety.

BACKGROUND

Technical Field

The present disclosure relates to systems and devices for testing water of a spa, pool, hot tub, or similar water containing vessel and, in particular, to systems and devices for introducing fluid reagents to a water sample obtained from the vessel and for determining water quality parameters from the water samples.

Background

Pool and spa owners often manage their own water chemistry by testing water quality parameters including pH, free chlorine, total chlorine, and total alkalinity. The owner can add chemicals and/or take other corrective action based on test results for the different water quality parameters. Different types of colorimetric, photometric, and spectrometric water tests are currently available. These tests involve mixing a fluid reagent to a water sample from the pool or spa to cause a color change. The degree of color change is compared to a color scale by the user to determine the water quality parameters for the sample.

Devices for testing spa water quality without direct involvement of the spa user are known. For example, U.S. Pat. No. 6,340,431, entitled "Spa chemistry monitor and treatment unit," is directed to a free-floating spa chemistry monitor unit for automated checking and adjustment of water chemistry in a spa and for maintaining the sanitization of the spa. The unit includes a buoyant housing, an on-board controller, and a plurality of sensors for taking water chemistry, such as pH and oxidation reduction potential levels at predetermined time intervals. The unit delivers selected metered doses of one or more chemicals based on the water chemistry readings.

U.S. Pat. No. 9,834,451, entitled "Chemical monitoring devices and methods," also describes a monitoring device for monitoring swimming pool water parameters (e.g., pH, chlorine, bromine, and/or oxygen reduction potential, total dissolved solids, etc.) that floats in the pool. The device periodically collects and tests water samples to determine water parameters for water in the pool. The device can be configured to communicate measured parameters and suggested actions for treatment to a remote location, such as to a user's smart phone.

Systems are also known for remotely controlling a spa based on information received from the pool or spa. Transmitted information can be accessed through a website or App to provide users with real-time or periodically updated information about the spa. For example, U.S. Pat. Nos. 7,982,625; 8,164,470; and U.S. Pat. No. 8,624,749 to Brochu et al. are directed to methods for monitoring a bathing system that measure electrical current drawn by the bathing system to determine whether the system is operating under normal or abnormal operating conditions. Results of the comparison can be transmitted wirelessly to a remote device and displayed to a user on a website or App.

SUMMARY

Non-limiting examples of the present invention will now be described in the following numbered clauses:

Clause 1: A spa tub, comprising: a spa shell defining an interior cavity configured to contain a volume of water; a circulation system in communication with the interior cavity of the spa shell, the circulation system being configured to create a flow of the water to and from the interior cavity of the spa shell; and a testing system configured to acquire water samples from the volume of water and perform water quality tests on the water samples, the testing system comprising: a housing; a circulation pump disposed within the housing, the circulation pump being configured to acquire the water samples from the volume of water; a replaceable reagent cartridge removably received within the housing, the replaceable reagent cartridge comprising at least one pouch for containing at least one chemical reagent; and a water test assembly disposed within the housing, the water test assembly being configured to receive the water samples acquired by the circulation pump and the at least one chemical reagent from the reagent cartridge, wherein the water test assembly is configured to mix the water samples and the chemical reagent and perform the water quality tests on the mixed water samples and chemical reagent.

Clause 2: The spa tub according to clause 1, wherein the water test assembly comprises a cartridge receiving portion and a reusable test portion.

Clause 3: The spa tub according to clause 2, wherein the reusable test portion comprises at least one reagent dispenser for accessing the at least one reagent in the at least one pouch and distributing the at least one reagent within the reusable test portion.

Clause 4: The spa tub according to clause 3, wherein the at least one pouch comprises a sealable closure at an end thereof and the at least one reagent dispenser comprises a needle configured to extend through the sealable closure to access the at least one reagent.

Clause 5: The spa tub according to clause 3 or clause 4, wherein the reagent cartridge and the cartridge receiving portion are configured to align the at least one reagent pouch with the at least one reagent dispenser.

Clause 6: The spa tub according to clause 5, wherein the cartridge receiving portion comprises at least one recess defined therein aligned with the at least one reagent dispenser and the at least one pouch comprises a spout projecting from the reagent cartridge, the spout of the at least one pouch being configured to be received in the at least one recess in the cartridge receiving portion to align the spout with the at least one reagent dispenser.

Clause 7: The spa tub according to any of clauses 3-6, wherein the reagent cartridge comprises a plurality of pouches each containing a respective chemical reagent and the reusable test portion comprises a plurality of reagent dispensers for accessing each of the reagents in the plurality of pouches and distributing the reagents within the reusable test portion.

Clause 8: The spa tub according to clause 7, wherein the reagent cartridge and the cartridge receiving portion are configured to align the plurality of reagent pouches with a respective one of the plurality of reagent dispensers.

Clause 9: The spa tub according to clause 7 or clause 8, wherein the plurality of pouches comprises five pouches each containing a respective chemical reagent and the reusable test portion comprises five reagent dispensers.

Clause 10: The spa tub according to any of clauses 2-9, wherein the cartridge receiving portion is configured such that the reagent cartridge is top-loaded within the cartridge receiving portion, the reagent cartridge and the cartridge receiving portion being configured to avoid incorrect insertion of the reagent cartridge in the cartridge receiving portion.

Clause 11: The spa tub according to clause 10, wherein the housing of the testing system comprises a door hingedly connected to a top of the housing to provide access to the cartridge receiving portion to allow the reagent cartridge to be inserted to and removed from the cartridge receiving portion.

Clause 12: The spa tub according to clause 11, wherein the housing further comprises a latch for securing the door in a closed position.

Clause 13: The spa tub according to any of clauses 1-12, wherein the reagent cartridge comprises a plurality of vent openings defined therein to allow cooling air to flow through the cartridge to maintain a temperature of the reagent.

Clause 14: The spa tub according to any of clauses 1-13, wherein the water test assembly is configured to conduct water quality tests for acidity, free chlorine, total chlorine, and/or total alkalinity.

Clause 15: The spa tub according to any of clauses 1-14, wherein the testing system further comprises a pre-filter disposed upstream of the circulation pump, the pre-filter being configured to remove particulate matter from the water samples acquired by the circulation pump.

Clause 16: The spa tub according to any of clauses 1-15, wherein the testing system further comprises a discharge filter disposed downstream of the water test assembly, the discharge filter being configured to at least partially remove the at least one reagent from the water samples after the water quality tests are performed.

Clause 17: The spa tub according to clause 16, wherein the discharge filter comprises an activated carbon layer and an ion exchange resin layer.

Clause 18: The spa tub according to clause 17, wherein the discharge filter further comprises an oxidation reduction alloy layer.

Clause 19: The spa tub according to any of clauses 1-18, wherein the testing system further comprises a main pump configured to draw a portion of the volume of water through the testing system, the main pump being disposed downstream of the water test assembly.

Clause 20: The spa tub according to clause 19, wherein the circulation pump within the housing is configured to acquire the water samples from the portion of the volume of water drawn by the main pump.

Clause 21: The spa tub according to clause 19, wherein the testing system further comprises a cooling assembly configured to maintain a temperature of the reagent cartridge.

Clause 22: The spa tub according to clause 21, wherein the portion of the volume of water drawn through the testing system by the main pump is directed through the cooling assembly and the cooling assembly is configured to transfer heat from an interior of the housing of the testing system to the portion of the volume of water directed through the cooling assembly.

Clause 23. The spa tub according to clause 22, wherein the cooling assembly comprises a thermoelectric cooling device, a water block for receiving and channeling the portion of the volume of water, a heat sink, and a fan configured to circulate air within the housing of the testing system, wherein the thermoelectric cooling device is configured to cool the heat sink and the fan is configured to draw air within the housing across the cooled heat sink.

Clause 24: The spa tub according to any of clauses 1-23, wherein the water test assembly comprises a test plate assembly comprising: a base plate comprising a top surface, a bottom surface, and a peripheral edge extending therebetween; a mixing chamber on the base plate comprising a waterسعة sample port, a reagent port, and a drain port; a sensor on the base plate configured to detect light transmitting through or reflecting from the mixing chamber; and a fluid circuit on the base plate for providing the water samples to the mixing chamber through the water sample port, for providing a dose of the at least one chemical reagent to the mixing chamber through the reagent port, and for conducting a mixed sample from the mixing chamber through the drain port after testing, the fluid circuit comprising: an inflow portion comprising at least one conduit extending between a plate inflow port and the water sample port of the mixing chamber; a reagent portion comprising at least one conduit extending from at least one plate reagent port to the reagent port of the mixing chamber; a drain outlet portion comprising a conduit extending from the drain port of the mixing chamber to a plate drain port; and at least one pump mounted to the base plate for moving the water samples, dose of the at least one chemical reagent, and/or mixed sample through the portions of the fluid circuit.

Clause 25: The spa tub according to clause 24, wherein the base plate comprises a substantially clear or transparent acrylic plate, and wherein the mixing chamber and conduits of the fluid circuit are machined or etched into a surface of the base plate.

Clause 26: The spa tub according to clause 24 or clause 25, wherein the at least one pump is configured to be operably connected to a motor enclosed in the housing of the testing system for driving the at least one pump.

Clause 27: The spa tub according to any of clauses 24-26, wherein the at least one pump comprises a peristaltic pump configured to contact a flexible portion of one of the conduits of the fluid circuit to move the water and/or the reagent through the conduits.

Clause 28: The spa tub according to any of clauses 24-27, wherein the at least one pump comprises a mixing pump positioned within a mixing loop portion of the fluid circuit, the mixing pump being configured to provide the water samples from the mixing chamber to the reagent portion through the mixing loop portion.

Clause 29: The spa tub according to any of clauses 24-28, further comprising a light source for projecting light through the mixing chamber, the light source comprising a broad spectrum white light source.

Clause 30: The spa tub according to clause 29, wherein the sensor is a CMOS optical sensor.

Clause 31: The spa tub according to clause 29, wherein the light source comprises at least one light-emitting diode that emits white light, and the sensor comprises a red-green-blue (RGB) light sensor configured to measure intensity of red, green, and blue light through the mixed sample.

Clause 32: The spa tub according to any of clauses 24-31, wherein the mixing chamber comprises a conduit arranged in a serpentine path on the top surface of the base plate, the serpentine path comprising multiple substantially straight segments connected by curved segments.

Clause 33: The spa tub according to clause 32, wherein the light source is configured to shine light through the multiple substantially straight segments of the serpentine path, and wherein the sensor measures color and/or intensity of light passing through the multiple substantially straight segments.

Clause 34: The spa tub according to any of clauses 24-33, wherein the mixing chamber is configured to contain a water sample with a volume of 2 mL or less.

Clause 35: The spa tub according to any of clauses 24-34, wherein the fluid circuit further comprises at least one valve for preventing fluid flow through portions of the conduits of the fluid circuit to control delivery of the water samples and/or the dose of the at least one chemical reagent to the mixing chamber.

Clause 36: The spa tub according to clause 35, wherein the fluid circuit further comprises a plurality of check valves positioned in the conduits for preventing backflow through conduits of the fluid circuit.

Clause 37: The spa tub according to any of clauses 24-36, wherein the fluid circuit further comprises a reagent input valve positioned on the reagent portion between the plate reagent inflow port and the reagent port of the mixing chamber, the reagent input valve having an open state in which the at least one chemical reagent from the reagent cartridge passes through the reagent input valve toward the mixing chamber and a closed state in which the at least one chemical reagent is prevented from passing through the reagent input valve.

Clause 38: The spa tub according to clause 37, wherein a volume of a conduit extending between the reagent input valve and the reagent port of the mixing chamber is a predetermined volume for a dose of the at least one chemical reagent to be used for a water test being performed.

Clause 39: The spa tub according to clause 38, wherein the volume of the conduit extending between the reagent input valve and the reagent port of the mixing chamber is from about 0.05 mL to about 1.0 mL.

Clause 40: The spa tub according to clause 39, wherein the conduit between the reagent input valve and the reagent port of the mixing chamber is arranged in a serpentine path, at least a portion of the conduit has a cross section area of less than 1.5 mm$^2$, and the conduit forming the serpentine path is substantially rigid.

Clause 41: The spa tub according to clause 40, wherein the conduit between the reagent inflow valve and the reagent port is sized to prevent the at least one chemical reagent from flowing backward from the mixing chamber into the reagent portion of the fluid circuit through the reagent port of the mixing chamber.

Clause 42: The spa tub according to any of clauses 24-41, further comprising a drain valve along the drain outlet portion of the fluid circuit positioned between the drain port of the mixing chamber and a drain outlet of the water test device, the drain valve having an open state in which the mixed sample passes through the drain valve from the mixing chamber toward the drain outlet and a closed state in which the mixed sample is prevented from passing through the drain valve toward the drain outlet.

Clause 43: The spa tub according to any of clauses 24-27, wherein the fluid circuit further comprises a mixing loop portion comprising at least one conduit extending between the water inflow portion and the reagent portion for flushing the at least one chemical reagent from the reagent portion into the mixing chamber.

Clause 44: The spa tub according to clause 43, wherein the mixing loop portion further comprises at least one mixing loop valve configured such that, when in an open state, the water samples flow from the mixing chamber, through the mixing loop portion, and reagent portion back to the mixing chamber, and when in a closed state, the water samples are prevented from passing from the mixing loop portion to the reagent portion of the fluid circuit.

Clause 45: The spa tub according to clause 44, wherein the at least one pump comprises a mixing pump positioned in the mixing loop portion upstream from the mixing loop valve, the mixing pump being configured to move the water samples through the mixing loop portion and reagent portion when the mixing loop valve is in the open state.

Clause 46: The spa tub according to any of clauses 24-45, wherein the testing system further comprises a motor configured to operate the at least one pump of the test plate assembly.

Clause 47: The spa tub according to clause 46, wherein the water test assembly comprises multiple test plate assemblies, and wherein the at least one pump of each of the multiple test plate assemblies is operated by the motor.

Clause 48: The spa tub according to clause 46 or clause 47, wherein the testing system further comprises a controller in electronic communication with the motor and the sensor of the at least one test plate assembly, the controller configured to activate the motor according to a predetermined water test protocol and receive and process color and/or light intensity information from the sensor obtained during the water test protocol.

Clause 49: The spa tub according to clause 48, wherein the controller is further configured to determine at least one water quality parameter for the water sample based on the received color and/or light intensity information.

Clause 50: The spa tub according to clause 49, wherein determining the at least one water quality parameter comprises calculating Hue, Saturation, and Value (HSV) for the mixed sample based on the measured color and/or light intensity information and determining the at least one water quality parameter based on the calculated Hue, Saturation, and Value.

Clause 51: The spa tub according to any of clauses 46-50, wherein the fluid circuit of the at least one test plate assembly further comprises at least one valve for preventing the water samples from flowing through conduits of the fluid circuit to control delivery of the water sample and/or reagent to the mixing chamber.

Clause 52: The spa tub according to clause 51, further comprising a valve actuator plate operably connected to a second motor poisoned in the housing by a cam assembly, wherein the base plate is mounted to the valve actuator plate, and wherein movement of the valve actuator plate opens and closes the at least one valve of the test plate assembly.

Clause 53: The spa tub according to clause 52, further comprising a cover plate positioned over the base plate and at least one flat resilient gasket positioned between the base plate and the cover plate.

Clause 54: The spa tub according to clause 53, wherein the at least one valve comprises a retractable member extending through the cover configured to press the flat resilient member into one of the conduits of the fluid circuit, thereby restricting or preventing fluid flow through the conduit.

Clause 55: The spa tub according to clause 54, wherein the resilient flat member biases the retractable member away from the conduit, thereby causing the at least one valve to open.

Clause 56: The spa tub according to any of clauses 52-55, wherein the controller is configured to cause the valve actuator plate to move between a plurality of positions corresponding to different states of the water test protocol, and wherein moving the valve actuator plate to a first position causes the least one valve to open and/or close to provide a purge state of the water test protocol, moving the valve actuator plate to a second position causes the at least one valve to open and/or close to provide a reagent preparation state of the water test protocol; moving the valve actuator plate to a third position opens and/or closes the at least one valve to provide a dose trim state of the water test protocol, and moving the valve actuator plate to a fourth position opens and/or closes the at least one valve to provide a mixing state of the water test protocol.

Clause 57: A testing system for performing water quality tests on a volume of water within a spa tub, the testing system comprising: a housing; a circulation pump disposed within the housing, the circulation pump being configured to acquire water samples from the volume of water in the spa tub; a replaceable reagent cartridge removably received within the housing, the replaceable reagent cartridge comprising at least one pouch for containing at least one chemical reagent; a water test assembly disposed within the housing, the water test assembly being configured to receive the water samples acquired by the circulation pump and the at least one chemical reagent from the reagent cartridge, wherein the water test assembly is configured to mix the water samples and the chemical reagent and perform the water quality tests on the mixed water samples and chemical reagent.

Clause 58: The testing system according to clause 57, wherein the water test assembly comprises a cartridge receiving portion and a reusable test portion.

Clause 59: The testing system according to clause 58, wherein the reusable test portion comprises at least one reagent dispenser for accessing the at least one reagent in the at least one pouch and distributing the at least one reagent within the reusable test portion.

Clause 60: The testing system according to clause 59, wherein the at least one pouch comprises a sealable closure at an end thereof and the at least one reagent dispenser comprises a needle configured to extend through the sealable closure to access the at least one reagent.

Clause 61: The testing system according to clause 59 or clause 60, wherein the reagent cartridge and the cartridge receiving portion are configured to align the at least one reagent pouch with the at least one reagent dispenser.

Clause 62: The testing system according to clause 61, wherein the cartridge receiving portion comprises at least one recess defined therein aligned with the at least one reagent dispenser and the at least one pouch comprises a spout projecting from the reagent cartridge, the spout of the at least one pouch being configured to be received in the at least one recess in the cartridge receiving portion to align the spout with the at least one reagent dispenser.

Clause 63: The testing system according to clause 59, wherein the reagent cartridge comprises a plurality of pouches each containing a respective chemical reagent and the reusable test portion comprises a plurality of reagent dispensers for accessing each of the reagents in the plurality of pouches and distributing the reagents within the reusable test portion.

Clause 64: The testing system according to clause 63, wherein the reagent cartridge and the cartridge receiving portion are configured to align the plurality of reagent pouches with a respective one of the plurality of reagent dispensers.

Clause 65: The testing system according to clause 63 or clause 64, wherein the plurality of pouches comprises five pouches each containing a respective chemical reagent and the reusable test portion comprises five reagent dispensers.

Clause 66: The testing system according to any of clauses 58-65, wherein the cartridge receiving portion is configured such that the reagent cartridge is top-loaded within the cartridge receiving portion, the reagent cartridge and the cartridge receiving portion being configured to avoid incorrect insertion of the reagent cartridge in the cartridge receiving portion.

Clause 67: The testing system according to clause 66, wherein the housing of the testing system comprises a door hingedly connected to a top of the housing to provide access to the cartridge receiving portion to allow the reagent cartridge to be inserted to and removed from the cartridge receiving portion.

Clause 68: The testing system according to clause 67, wherein the housing further comprises a latch for securing the door in a closed position.

Clause 69: The testing system according to any of clauses 57-68, wherein the reagent cartridge comprises a plurality of vent openings defined therein to allow cooling air to flow through the cartridge to maintain a temperature of the reagent.

Clause 70: The testing system according to any of clauses 57-69, wherein the water test assembly is configured to conduct water quality tests for acidity, free chlorine, total chlorine, and/or total alkalinity.

Clause 71: The testing system according to any of clauses 57-70, further comprising a pre-filter disposed upstream of the circulation pump, the pre-filter being configured to remove particulate matter from the water samples acquired by the circulation pump.

Clause 72: The testing system according to any of clauses 57-71, further comprising a discharge filter disposed downstream of the water test assembly, the discharge filter being configured to at least partially remove the at least one reagent from the water samples after the water quality tests are performed.

Clause 73: The testing system according to clause 72, wherein the discharge filter comprises an activated carbon layer and an ion exchange resin layer.

Clause 74: The testing system according to clause 73, wherein the discharge filter further comprises an oxidation reduction alloy later.

Clause 75: The testing system according to any of clauses 57-74, further comprising a main pump configured to draw a portion of the volume of water through the testing system, the main pump being disposed downstream of the water test assembly.

Clause 76: The testing system according to clause 75, wherein the circulation pump within the housing is configured to acquire the water samples from the portion of the volume of water drawn by the main pump.

Clause 77: The testing system according to clause 75 or clause 76, further comprising a cooling assembly configured to maintain a temperature of the reagent cartridge.

Clause 78: The testing system according to clause 77, wherein the portion of the volume of water drawn through the testing system by the main pump is directed through the cooling assembly and the cooling assembly is configured to transfer heat from an interior of the housing of the testing system to the portion of the volume of water directed through the cooling assembly.

Clause 79: The testing system according to clause 78, wherein the cooling assembly comprises a thermoelectric cooling device, a water block for receiving and channeling the portion of the volume of water, a heat sink, and a fan configured to circulate air within the housing of the testing system, wherein the thermoelectric cooling device is configured to cool the heat sink and the fan is configured to draw air within the housing across the cooled heat sink.

Clause 80: The testing system according to any of clauses 57-79, wherein the water test assembly comprises a test plate assembly comprising: a base plate comprising a top surface, a bottom surface, and a peripheral edge extending therebetween; a mixing chamber on the base plate comprising a water sample port, a reagent port, and a drain port; a sensor on the base plate configured to detect light transmitting through or reflecting from the mixing chamber; and a fluid circuit on the base plate for providing the water samples to the mixing chamber through the water sample port, for providing a dose of the at least one chemical reagent to the mixing chamber through the reagent port, and for conducting a mixed sample from the mixing chamber through the drain port after testing, the fluid circuit comprising: an inflow portion comprising at least one conduit extending between a plate inflow port and the water sample port of the mixing chamber; a reagent portion comprising at least one conduit extending from at least one plate reagent port to the reagent port of the mixing chamber; a drain outlet portion comprising a conduit extending from the drain port of the mixing chamber to a plate drain port; and at least one pump mounted to the base plate for moving the water samples, dose of the at least one chemical reagent, and/or mixed sample through the portions of the fluid circuit.

Clause 81: A testing system for performing water quality tests on a volume of water within a spa tub, the testing system comprising: a housing; a circulation pump disposed within the housing, the circulation pump being configured to acquire water samples from a volume of water in the spa tub; a reagent cartridge received within the housing, the reagent cartridge comprising at least one pouch for containing at least one chemical reagent; a cooling assembly disposed in the housing, the cooling assembly being configured to transfer heat from an interior of the housing of the testing system to the volume of water in the spa tub to maintain a temperature of the reagent cartridge; a water test assembly disposed within the housing, the water test assembly being configured to receive the water samples acquired by the circulation pump and the at least one chemical reagent from the reagent cartridge, wherein the water test assembly is configured to mix the water samples and the chemical reagent and perform the water quality tests on the mixed water samples and chemical reagent.

Clause 82: The testing system according to clause 81, wherein the cooling assembly comprises a thermoelectric cooling device, a water block for receiving and channeling the portion of the volume of water, a heat sink, and a fan configured to circulate air within the housing of the testing system, wherein the thermoelectric cooling device is configured to cool the heat sink and the fan is configured to draw air within the housing across the cooled heat sink.

Clause 83: The testing system according to clause 82, further comprising a main pump configured to draw the portion of the volume of water through the cooling assembly, the main pump being disposed downstream of the water test assembly.

Clause 84: The testing system according to clause 83, wherein the circulation pump within the housing is configured to acquire the water samples from the portion of the volume of water drawn by the main pump.

Clause 85: The testing system according to any of clauses 81-84, wherein the reagent cartridge is removably received in the housing.

Clause 86: The testing system according to clause 85, wherein the water test assembly comprises a cartridge receiving portion and a reusable test portion.

Clause 87: The testing system according to clause 86, wherein the reusable test portion comprises at least one reagent dispenser for accessing the at least one reagent in the at least one pouch and distributing the at least one reagent within the reusable test portion.

Clause 88: The testing system according to clause 87, wherein the at least one pouch comprises a sealable closure at an end thereof and the at least one reagent dispenser comprises a needle configured to extend through the sealable closure to access the at least one reagent.

Clause 89: The testing system according to clause 87 or clause 88, wherein the reagent cartridge and the cartridge receiving portion are configured to align the at least one reagent pouch with the at least one reagent dispenser.

Clause 90: The testing system according to clause 89, wherein the cartridge receiving portion comprises at least one recess defined therein aligned with the at least one reagent dispenser and the at least one pouch comprises a spout projecting from the reagent cartridge, the spout of the at least one pouch being configured to be received in the at least one recess in the cartridge receiving portion to align the spout with the at least one reagent dispenser.

Clause 91: The testing system according to clause 87, wherein the reagent cartridge comprises a plurality of pouches each containing a respective chemical reagent and the reusable test portion comprises a plurality of reagent dispensers for accessing each of the reagents in the plurality of pouches and distributing the reagents within the reusable test portion.

Clause 92: The testing system according to clause 91, wherein the reagent cartridge and the cartridge receiving portion are configured to align the plurality of reagent pouches with a respective one of the plurality of reagent dispensers.

Clause 93: The testing system according to clause 91 or clause 92, wherein the plurality of pouches comprises five pouches each containing a respective chemical reagent and the reusable test portion comprises five reagent dispensers.

Clause 94: The testing system according to any of clauses 86-93, wherein the cartridge receiving portion is configured such that the reagent cartridge is top-loaded within the cartridge receiving portion, the reagent cartridge and the cartridge receiving portion being configured to avoid incorrect insertion of the reagent cartridge in the cartridge receiving portion.

Clause 95: The testing system according to clause 94, wherein the housing of the testing system comprises a door hingedly connected to a top of the housing to provide access to the cartridge receiving portion to allow the reagent cartridge to be inserted to and removed from the cartridge receiving portion.

Clause 96: The testing system according to clause 95, wherein the housing further comprises a latch for securing the door in a closed position.

Clause 97: The testing system according to any of clauses 86-96, wherein the reagent cartridge comprises a plurality of vent openings defined therein to allow cooling air to flow through the cartridge to maintain a temperature of the reagent.

Clause 98: The testing system according to any of clauses 81-97, wherein the water test assembly is configured to conduct water quality tests for acidity, free chlorine, total chlorine, and/or total alkalinity.

Clause 99: The testing system according to any of clauses 81-98, further comprising a pre-filter disposed upstream of the circulation pump, the pre-filter being configured to remove particulate matter from the water samples acquired by the circulation pump.

Clause 100: The testing system according to any of clauses 81-99, further comprising a discharge filter disposed downstream of the water test assembly, the discharge filter being configured to at least partially remove the at least one reagent from the water samples after the water quality tests are performed.

Clause 101: The testing system according to clause 100, wherein the discharge filter comprises an activated carbon layer and an ion exchange resin layer.

Clause 102: The testing system according to clause 101, wherein the discharge filter further comprises an oxidation reduction alloy later.

Clause 103: The testing system according to any of clauses 81-102, wherein the water test assembly comprises a test plate assembly comprising: a base plate comprising a top surface, a bottom surface, and a peripheral edge extending therebetween; a mixing chamber on the base plate comprising a water sample port, a reagent port, and a drain port; a sensor on the base plate configured to detect light transmitting through or reflecting from the mixing chamber; and a fluid circuit on the base plate for providing the water samples to the mixing chamber through the water sample port, for providing a dose of the at least one chemical reagent to the mixing chamber through the reagent port, and for conducting a mixed sample from the mixing chamber through the drain port after testing, the fluid circuit comprising: an inflow portion comprising at least one conduit extending between a plate inflow port and the water sample port of the mixing chamber; a reagent portion comprising at least one conduit extending from at least one plate reagent port to the reagent port of the mixing chamber; a drain outlet portion comprising a conduit extending from the drain port of the mixing chamber to a plate drain port; and at least one pump mounted to the base plate for moving the water samples, dose of the at least one chemical reagent, and/or mixed sample through the portions of the fluid circuit.

Clause 104: A water test device for a pool or spa for testing water from the pool or spa using one or more fluid reagents, the test device comprising: a base plate comprising a top surface, a bottom surface, and a peripheral edge extending therebetween; a mixing chamber on the base plate comprising a water sample port, a reagent port, and a drain port; a sensor on the base plate configured to detect light transmitting through or reflecting from the mixing chamber; and a fluid circuit on the base plate for providing the water from the pool or spa to the mixing chamber through the water sample port, for providing a dose of a reagent to the mixing chamber through the reagent port, and for conducting a mixed sample from the mixing chamber through the drain port after test, the fluid circuit comprising: an inflow portion comprising at least one conduit extending between a device inflow port and the water sample port of the mixing chamber; a reagent portion comprising at least one conduit extending from at least one device reagent port to the reagent port of the mixing chamber; a drain outlet portion comprising a conduit extending from the drain port of the mixing chamber to a device drain port; and at least one pump for moving the water from the pool or spa, reagent, and/or mixed sample through the portions of the fluid circuit.

Clause 105: The test device of clause 104, wherein the water test device is configured to be placed in fluid communication with the water of the pool or spa, so that a water sample can be provided to the water test device directly from the pool or spa.

Clause 106: The test device of clause 104 or clause 105, wherein the base plate comprises a substantially clear or transparent acrylic plate, and wherein the mixing chamber and conduits of the fluid circuit are machined or etched into a surface of the base plate.

Clause 107: The test device of any of clauses 104-106, wherein the at least one pump is configured to be operably connected to a motor for driving the at least one pump.

Clause 108: The test device of any of clauses 104-107, wherein the at least one pump comprises a peristaltic pump configured to contact a flexible portion of one of the conduits of the fluid circuit to move the water and/or the reagent through the conduits.

Clause 109: The test device of any of clauses 104-108, wherein the at least one pump comprises a mixing pump positioned within a mixing loop portion of the fluid circuit, the mixing pump being configured to provide water from the mixing chamber to the reagent portion of the fluid circuit.

Clause 110: The test device of any of clauses 104-109, further comprising a light source for projecting light through the mixing chamber, the light source comprising a broad spectrum white light source.

Clause 111: The test device of clause 110, wherein the sensor is a CMOS optical sensor.

Clause 112: The test device of clause 110, wherein the light source comprises at least one light-emitting diode that emits white light, and the sensor comprises a red-green-blue (RGB) light sensor configured to measure intensity of red, green, and blue light through the mixed sample.

Clause 113: The test device of any of clauses 104-112, wherein the mixing chamber comprises a conduit arranged in a serpentine path on the top surface of the base plate, the serpentine path comprising multiple substantially straight segments connected by curved segments.

Clause 114: The test device of clause 113, wherein the light source is configured to shine light through the multiple substantially straight segments of the serpentine path, and wherein the sensor measures an intensity of light passing through the multiple substantially straight segments.

Clause 115: The test device of any of clauses 104-114, wherein the test device is configured to be connected to multiple reagent sources containing different reagents that test different water quality parameters, the water quality parameters comprising pH, total alkalinity, free chlorine, total chlorine, or total dissolved solids.

Clause 116: The test device of any of clauses 104-115, wherein the mixing chamber is configured to contain a water sample with a volume of 2 mL or less.

Clause 117: The test device of any of clauses 104-116, wherein the fluid circuit further comprises at least one valve for preventing water flow through portions of the conduits of the fluid circuit to control delivery of the pool or spa water and/or the dose of the reagent to the mixing chamber.

Clause 118: The test device of clause 117, wherein the base plate is configured to be directly or indirectly mounted to a valve actuator plate, and wherein the water test device is configured so that lateral movement of the valve actuator plate opens and closes the at least one valve.

Clause 119: The test device of clause 117 or clause 118, wherein the fluid circuit further comprises a plurality of check valves positioned in the conduits for preventing water backflow.

Clause 120: The test device of any of clauses 104-119, wherein the fluid circuit further comprises a reagent input valve positioned on the reagent portion between the device reagent port and the reagent port of the mixing chamber, the reagent input valve having an open state in which reagent from a reagent source passes through the reagent input valve toward the mixing chamber and a closed state in which the reagent is prevented from passing through the reagent input valve.

Clause 121: The test device of clause 120, wherein a volume of a conduit extending between the reagent input valve and the reagent port of the mixing chamber is a predetermined volume for a dose of the reagent to be used for a water test being performed.

Clause 122: The test device of clause 121, wherein the volume of the conduit extending between the reagent input valve and the reagent port of the mixing chamber is from about 0.05 mL to about 1.0 mL.

Clause 123: The test device of clause 121 or clause 122, wherein the predetermined volume of the dose of the reagent is determined based on a volume of the mixing chamber, a volume of a water sample obtained from the pool or spa, and the water test being performed.

Clause 124: The test device of any of clauses 121-123, wherein the conduit between the reagent input valve and the reagent port of the mixing chamber is arranged in a serpentine path, at least a portion of the conduit has a cross section area of less than 1.5 mm$^2$, and the portion of the conduit forming the serpentine path is substantially rigid.

Clause 125: The test device of clause 124, wherein the conduit between the reagent inflow valve and the reagent port is sized to prevent reagent from flowing backward from the mixing chamber into the reagent portion of the fluid circuit through the reagent port of the mixing chamber.

Clause 126: The test device of any of clauses 104-125, further comprising a drain valve along the drain outlet portion of the fluid circuit positioned between the drain port of the mixing chamber and a drain outlet of the water test device, the drain valve having an open state in which the mixed sample passes through the drain valve from the mixing chamber toward the drain outlet and a closed state in which the mixed sample is prevented from passing through the drain valve toward the drain outlet.

Clause 127: The test device of any of clauses 104-108, wherein the fluid circuit further comprises a mixing loop portion comprising at least one conduit extending between the water inflow portion and the reagent portion for flushing reagent from the reagent portion into the mixing chamber.

Clause 128: The test device of clause 127, wherein the mixing loop portion further comprises at least one mixing loop valve configured such that, when in an open state, water flows from the mixing chamber, through the mixing loop portion, and reagent portion back to the mixing chamber, and when in a closed state, water is prevented from passing from the mixing loop portion to the reagent portion of the fluid circuit.

Clause 129: The test device of clause 128, wherein the at least one pump comprises a mixing pump positioned in the mixing loop portion upstream from the mixing loop valve, the mixing pump being configured to move water through the mixing loop portion and reagent portion when the mixing loop valve is in the open state.

Clause 130: A method for testing a water sample from a pool or spa with a water test device in fluid communication with water contained in the pool or spa, the method comprising: connecting a water test device to a water circulation assembly of a pool or spa for providing water from the pool or spa to the water test device, wherein the water test device comprises: a base plate comprising a top surface, a bottom surface, and a peripheral edge extending therebetween; a mixing chamber on the base plate comprising a water sample port, a reagent port, and a drain port; a sensor on the base plate configured to detect light transmitting through or reflecting from the mixing chamber; and a fluid circuit on the base plate for providing the water from the pool or spa to the mixing chamber through the water sample port, for providing a dose of a reagent to the mixing chamber through the reagent port, and for conducting a mixed sample from the mixing chamber through the drain port after test; introducing the reagent to the water test device from a reagent source; introducing the water of the pool or spa to the water test device; causing a dose of the introduced reagent and a sample of the water from the pool or spa to mix together thereby providing the mixed sample in the mixing chamber of the water test device; measuring color and/or light intensity for light shown through or reflected from the mixed sample in the mixing chamber with the sensor of the water test device; and determining, with at least one computer processor, water quality parameters for the water sample based on the measured color and/or light intensity.

Clause 131: The method of clause 130, wherein introducing the reagent to the water test device comprises introducing at least two types of reagents to the mixing chamber of the test device for testing at least two water quality parameters simultaneously.

Clause 132: The method of clause 131, wherein the at least two water quality parameters comprise at least two of pH, total alkalinity, free chlorine, total chlorine, or total dissolved solids.

Clause 133: The method of any of clauses 130-132, wherein introducing the reagent to the water test device comprises: opening a reagent inflow valve positioned on a reagent portion of the fluid circuit so that reagent from the reagent source flows into a regent dose conduit of the reagent portion of the fluid circuit and so that excess reagent passes through the reagent port into the mixing chamber; and trimming the excess reagent from the mixing chamber by flushing the mixing chamber with water from the pool or spa.

Clause 134: The method of clause 133, wherein a volume of the reagent dose conduit between the reagent inflow valve and the reagent port of the mixing chamber corresponds to a volume for a dose of reagent for the water test being performed.

Clause 135: The method of any of clauses 130-134, wherein the fluid circuit comprises: an inflow portion comprising at least one conduit extending between a device inflow port and the water sample port of the mixing chamber; a reagent portion comprising at least one conduit extending from at least one device reagent port to the reagent port of the mixing chamber; a drain outlet portion comprising a conduit extending from the drain port of the mixing chamber to a device drain port; and a mixing loop portion comprising at least one conduit extending between the water inflow portion and the reagent portion.

Clause 136: The method of clause 135, wherein the mixing loop portion further comprises a mixing loop valve that, when in an open state, permits water to pass through the mixing loop portion to the reagent portion and, when in a closed state, prevents water from passing through the mixing loop portion to the reagent portion of the fluid circuit.

Clause 137: The method of clause 136, further comprising purging the fluid circuit and mixing chamber prior to introducing a water sample to be tested to the water test device, wherein purging the fluid circuit comprises: opening an inflow valve on the inflow portion of the fluid circuit so that water passes through the inflow portion of the fluid circuit directly to the mixing chamber; opening a drain valve positioned in the drain outlet portion of the fluid circuit so that the water passes through the mixing chamber and away from the mixing chamber of the water test device, and causing the water from the pool or spa to flow through the mixing chamber and through the drain.

Clause 138: The method of clause 137, wherein purging the fluid circuit further comprises opening the mixing loop valve so that the water from the pool or spa passes through the mixing loop portion and reagent portion of the fluid circuit to the mixing chamber to flush fluids from the mixing loop portion and reagent portion of the fluid circuit.

Clause 139: The method of any of clauses 136-138, wherein causing a dose of the introduced reagent and the water sample to mix together comprises closing a water sample inflow valve to prevent a water sample in the mixing chamber from flowing back to the pool or spa, opening the mixing loop valve so that the water sample passes from the mixing chamber through the water sample port of the mixing chamber, through the mixing loop portion, through the reagent portion and, along with any reagent in the reagent portion, back to the mixing chamber.

Clause 140: The method of clause 139, wherein the water test device further comprises at least one mixing pump positioned in the mixing loop portion upstream from the mixing loop valve, and wherein causing the introduced dose of reagent and water sample to mix together further comprises activing the mixing pump to move the water sample through the mixing loop portion and reagent portion of the fluid circuit back to the mixing chamber.

Clause 141: The method of clause 139 or clause 140, wherein water flow from the mixing chamber through the mixing loop portion and reagent portion is carried out for a duration sufficient to allow the water sample to mix with reagent in the reagent portion of the fluid circuit, wherein the sufficient duration is from about 100 seconds to about 150 seconds.

Clause 142: A water quality test system comprising: at least one water test device comprising a base plate comprising a top surface, a bottom surface, and a peripheral edge extending therebetween, a mixing chamber on the base plate comprising a water sample port, a reagent port, and a drain port, a sensor on the base plate configured to detect light transmitting through or reflecting from the mixing chamber, a fluid circuit on the base plate for providing the water from the pool or spa to the mixing chamber through the water sample port, for providing a dose of a reagent to the mixing chamber through the reagent port, and for conducting a mixed sample from the mixing chamber through the drain port after test, and at least one pump for moving the water from the pool or spa, reagent, and/or mixed sample through the portions of the fluid circuit; a motor configured to operate the at least one pump of the at least one test device; and a controller in electronic communication with the motor and the sensor of the water test device, the controller configured to activate the motor according to a predetermined water test protocol and receive and process color and/or light intensity information from the sensor obtained during the water test protocol.

Clause 143: The test system of clause 142, comprising multiple water test devices, and wherein the at least one pump of each of the multiple test devices is operated by the motor.

Clause 144: The test system of clause 142 or clause 143, wherein the controller is further configured to determine at least one water quality parameter for the water sample based on the received color and/or light intensity information.

Clause 145: The test system of clause 144, wherein the at least one water quality parameter comprises at least one of pH, total alkalinity, free chlorine, total chlorine, or total dissolved solids.

Clause 146: The system of clause 144 or clause 145, wherein determining the at least one water quality parameter comprises calculating Hue, Saturation, and Value (HSV) for the mixed sample based on the measured color and/or light intensity information and determining the at least one water quality parameter based on the calculated Hue, Saturation, and Value.

Clause 147: The test system of any of clauses 142-146, wherein the fluid circuit of the at least one water test device further comprises at least one valve for preventing water flow through conduits of the fluid circuit to control delivery of the water sample and/or reagent to the mixing chamber.

Clause 148: The test system of clause 147, further comprising a valve actuator plate operably connected to a second motor by a cam assembly, wherein the water test device is mounted to the valve actuator plate, and wherein movement of the valve actuator plate opens and closes the at least one valve of the water test device.

Clause 149: The test system of clause 148, further comprising a cover plate positioned over the base plate and at least one flat resilient gasket positioned between the base plate and the cover plate.

Clause 150: The test system of clause 149, wherein the at least one valve comprises a retractable member extending through the cover configured to press the flat resilient member into one of the conduits of the fluid circuit, thereby restricting or preventing fluid flow through the conduit.

Clause 151: The test system of clause 150, wherein the resilient flat member biases the retractable member away from the conduit, thereby causing the valve to open.

Clause 152: The test system of any of clauses 148-151, wherein the controller is configured to cause the valve actuator plate to move between a plurality of positions corresponding to different states of the water test protocol, and wherein moving the valve actuator plate to a first position causes the least one valve to open and/or close to provide a purge state of the water test protocol, moving the valve actuator plate to a second position causes the at least one valve to open and/or close to provide a reagent preparation state of the water test protocol; moving the valve actuator plate to a third position opens and/or closes the at least one valve to provide a dose trim state of the water test protocol, and moving the valve actuator plate to a fourth position opens and/or closes the at least one valve to provide a mixing state of the water test protocol.

Clause 153: The test system of any of clauses 142-152, wherein the controller is configured to execute the water test protocol by: causing a reagent valve of the water test device to open to introduce the reagent to the water test device from a reagent source; causing a water inflow valve of the test device to open to introduce the water of the pool or spa to the water test device; activating the motor to cause a dose of the introduced reagent and a sample of the water from the pool or spa to mix together thereby providing the mixed sample in the mixing chamber of the water test device; and causing the sensor to measure color and/or light intensity for light shown through or reflected from the mixed sample in the mixing chamber.

Clause 154: The test system of clause 153, wherein the controller is configured to cause at least two types of reagents to be introduced to the mixing chamber of the test device for testing at least two water quality parameters simultaneously.

Clause 155: The test system of clause 153 or clause 154, wherein the controller causes the reagent valve and the water inflow valve to open by causing a valve actuator plate mounted to the water test device to move laterally to a position in which pressure on both valves is released, allowing the vales to open.

Clause 156: The test system of any of clauses 153-155, wherein introducing the reagent to the water test device comprises: opening the reagent valve positioned on the reagent portion of the fluid circuit so that reagent from the reagent source flows into a regent dose conduit of the reagent portion of the fluid circuit and so that excess reagent passes through the reagent port into the mixing chamber; and trimming the excess reagent from the mixing chamber by flushing the mixing chamber with water from the pool or spa.

Clause 157: The test system of clause 156, wherein a volume of the reagent dose conduit between the reagent inflow valve and the reagent port of the mixing chamber is the dose of reagent for the water test being performed.

Clause 158: The test system of any of clauses 153-157, wherein the fluid circuit comprises: an inflow portion comprising at least one conduit extending between a device inflow port and the water sample port of the mixing chamber; a reagent portion comprising at least one conduit extending from at least one device reagent port to the reagent port of the mixing chamber; a drain outlet portion comprising a conduit extending from the drain port of the mixing chamber to a device drain port; and a mixing loop portion comprising at least one conduit extending between the water inflow portion and the reagent portion.

Clause 159: The test device of clause 158, wherein the mixing loop portion further comprises a mixing loop valve that, when in an open state, permits water to pass through the mixing loop portion to the reagent portion and, when in a closed state, prevents water from passing through the mixing loop portion to the reagent portion of the fluid circuit.

Clause 160: The test system of clause 159, wherein the controller is configured to purge the fluid circuit and mixing chamber prior to introducing a water sample to be tested to the water test device, wherein the controller causes purging of the fluid circuit by: causing the water inflow valve on the inflow portion of the fluid circuit to open so that water passes through the inflow portion of the fluid circuit directly to the mixing chamber; causing a drain valve positioned in the drain outlet portion of the fluid circuit to open so that the water passes through the mixing chamber and away from the mixing chamber of the water test device, and causing the water from the pool or spa to flow through the mixing chamber and through the drain.

Clause 161: The test system of clause 160, wherein purging the fluid circuit further comprises causing the mixing loop valve to open so that the water from the pool or spa passes through the mixing loop portion and reagent portion of the fluid circuit to the mixing chamber to flush fluids from the mixing loop portion and reagent portion of the fluid circuit.

Clause 162: The test system of any of clauses 159-161, wherein the controller causes the dose of the introduced reagent and the water sample to mix together by: causing the water sample inflow valve to close to prevent a water sample in the mixing chamber from flowing back to the pool or spa, and causing the mixing loop valve to open so that the water sample passes from the mixing chamber through the water sample port, through the mixing loop portion, through the reagent portion and, along with any reagent in the reagent portion, back to the mixing chamber.

Clause 163: The test system of clause 162, wherein the at least one pump comprises a mixing pump positioned in the mixing loop portion upstream from the mixing loop valve, and wherein causing the introduced dose of reagent and water sample to mix together further comprises activating the mixing pump to move the water sample through the mixing loop portion and reagent dose portion of the fluid circuit back to the mixing chamber, wherein fluid flow from the mixing chamber through the mixing loop portion and reagent portion is carried out for a duration sufficient to allow the water sample to mix with reagent in the reagent dose conduit, wherein the sufficient duration is from about 100 seconds to about 150 seconds.

Clause 164: The test system of any of clauses 142-163, further comprising a circulation pump external to the at least one test device for moving the mixed sample from the test device.

Clause 165: A remote system for water quality monitoring for a pool or spa, the system comprising: a pool or spa comprising a spa controller and a wired or wireless transmitter; a water test device fluidly connected to the pool or spa to receive water from the pool or spa, the water test device comprising a mixing chamber, a sensor electrically connected to the spa controller configured to detect color and/or light intensity information for light transmitting through or reflecting from the mixing chamber, a fluid circuit for providing water from the pool or spa to the mixing chamber, for providing a dose of a reagent to the mixing chamber, and for conducting a mixed sample from the mixing chamber through the drain port after testing; and at least one processor remote from the pool or spa in communication with the spa controller via the wired or wireless transmitter, the at least one processor configured to: receive water quality parameters from the spa controller determined based on the sensed color and/or light intensity information provided by the sensor; and determine at least one instruction to be carried out based on the received water quality parameters.

Clause 166: The remote system of clause 165, wherein the at least one remote processor is further configured to provide the determined instruction to a user device to be displayed to a user of the pool or spa.

Clause 167: The remote system of clause 166, wherein the user device comprises a display on the spa.

Clause 168: The remote system of clause 166 or clause 167, wherein the user device comprises a portable electronic device in wireless communication with the remote processor.

Clause 169: The remote system of any of clauses 166-168, wherein the instruction comprises an instruction to the user to add chemicals to the spa.

Clause 170: The remote system of any of clauses 166-169, wherein the at least one processor is configured to confirm that chemicals have been added a predetermined period of time after providing the instruction to the user.

Clause 171: The remote system of clause 165, wherein the at least one processor is further configured to provide the determined at least one instruction to the spa controller, and wherein the spa controller is configured to automatically activate a spa chemical and/or filter system in response to the received instruction.

Clause 172: The remote system of clause 171, wherein the spa chemical and/or filter system comprises a chlorine generator device, and wherein the spa controller is configured to cause the chlorine generator to provide chorine to the spa water in response to the instruction received from the remote processor.

Clause 173: The remote system of any of clauses 165-172, wherein the at least one processor is in communication with a database of historical water quality parameters for the spa and wherein the determined instruction is based, at least in part, on information in the historical database.

Clause 174: The remote system of clause 173, wherein the historical database comprises historical information about one or more of pH, total alkalinity, total chlorine, total dissolved solids, or temperature for the water of the pool or spa.

Clause 175: The remote system of clause 173 or clause 174, wherein the at least one processor is configured to process information contained in the historical database to determine a trend for one or more of pH, total alkalinity, total chlorine, total dissolved solids, or temperature, and wherein the determined at least one instruction is based at least in part on the identified trend.

Clause 176: The remote system of any of clauses 173-175, wherein the historical database further comprises historical weather information for a location where the spa is installed.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1:
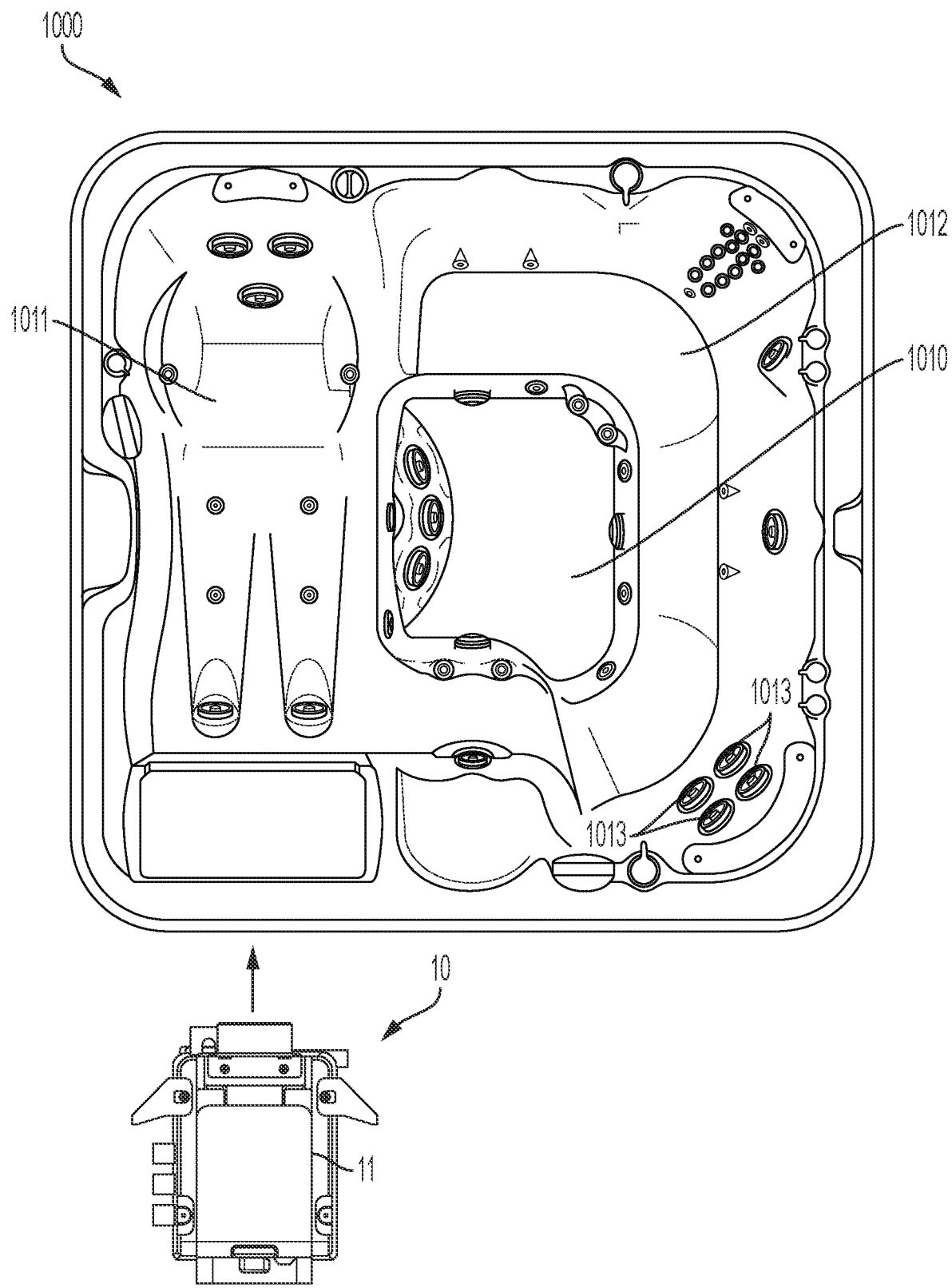
FIG. 1 is a top view of a spa tub including a water testing system according to an example of the present disclosure.

As used herein, the singular forms of "a", "an", and "the" include plural referents unless the context clearly states otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings and described in the following specification are examples. Hence, specific dimensions and other physical characteristics related to the embodiments disclosed herein are not to be considered as limiting.

Unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10. That is, all subranges beginning with a minimum value equal to or greater than 1 and ending with a maximum value equal to or less than 10, and all subranges in between, e.g., 1 to 6.3, or 5.5 to 10, or 2.7 to 6.1.

With reference to the figures, the present disclosure is directed to a water testing system 10 for a water containing vessel such as a pool or spa 1000. While the following discussion focuses primarily on water sensing devices and systems that can be connected to and adapted for use with a spa, the devices and systems disclosed herein can also be used with pools, bathtubs, whirlpools, Roman baths, and similar bathing devices, as are known in the art. The water testing system 10 can be configured to acquire water samples from the pool or spa for testing water quality parameters including acidity (e.g., pH), free chlorine, total chlorine, and/or total alkalinity with optical sensor(s). Other water quality tests may also be performed. For example, other types of sensors (e.g., non-optical sensors) may be used to detect water conductivity (e.g., total dissolved solids), salinity, and/or temperature.

As described in further detail herein, the water testing system 10 for the spa 1000 includes a system housing 11 that houses the components of the system 10. The system 10 also includes a removable cartridge 50 containing one or more containers or pouches 51 of chemical reagents utilized during the water quality tests and a reagent dispensing assembly for directing the chemical reagents from the container or pouches to a water test assembly 12. The system 10 also includes a cooling assembly 70 including a thermoelectric cooling device (TEC) device 78 for controlling a temperature of the cartridge 50 and reagents contained in the containers or pouches 51 to avoid degradation of the reagents, which can occur when the reagents are exposed to high temperatures. The water testing system 10 further includes the water test assembly 12 including water test devices 110 (also referred to herein as test plates or test plate assemblies) that define fluid conduits or grooves for mixing a water sample with a dose of reagent and testing devices for collecting water quality data from test samples. The water testing system 10 can further include a water filter assembly for filtering water samples containing reagents after a water sample is tested. In some examples, the water testing system 10 and/or spa 1000 can be integrated in a spa monitoring network for collecting data from a fleet of spas and/or for providing operating instructions from remote systems or devices to the spas.

Spa and Spa Electrical Components

Figure 2:
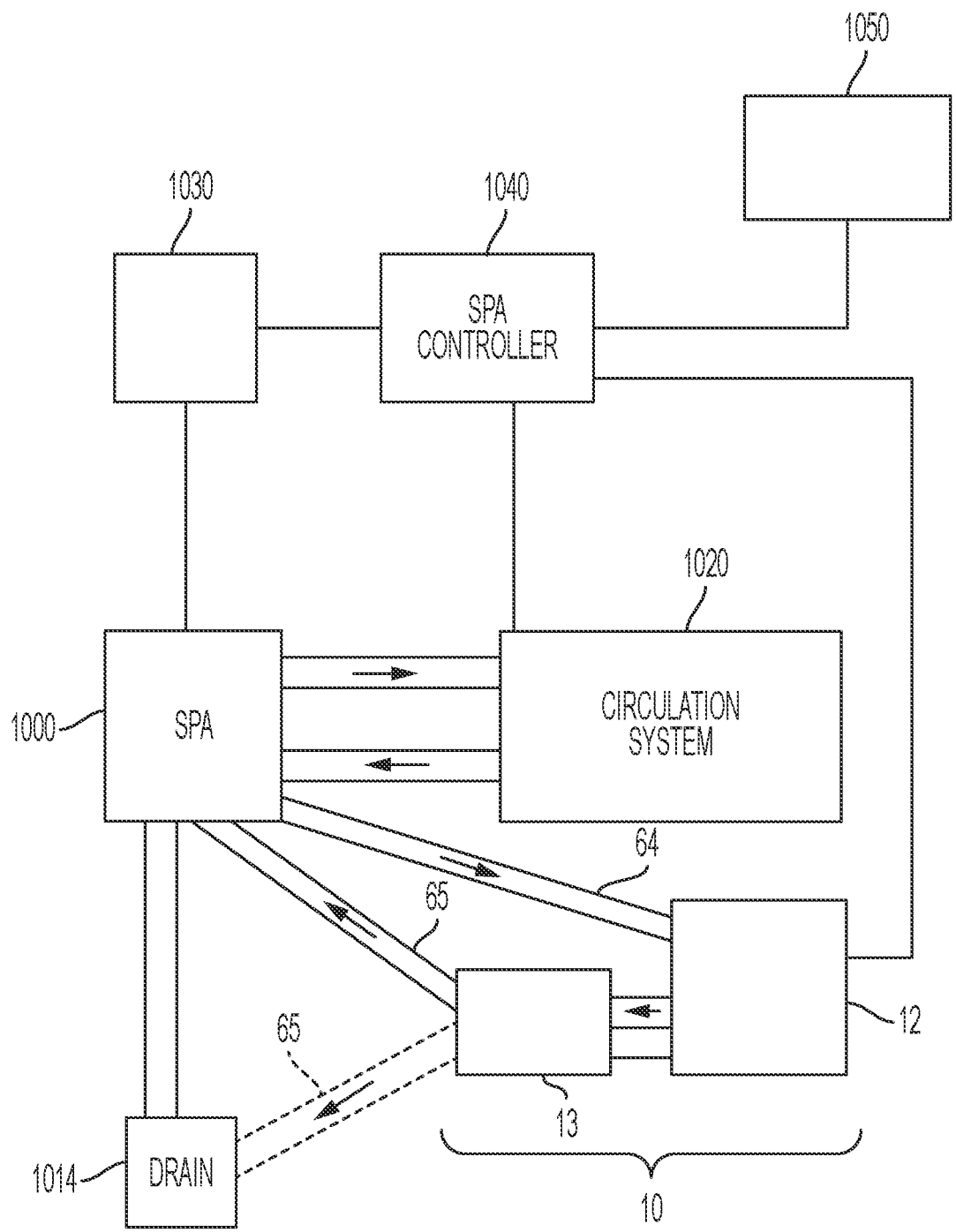
FIG. 2 is a schematic of the fluid and electronic connections of the spa tub and water testing system of FIG. 1 according to an example of the present disclosure.

With reference to FIGS. 1 and 2, the spa tub 1000 including the water testing system 10 is shown in accordance with an example of the present disclosure. The spa tub 1000 may include a spa shell 1010 that defines an interior cavity or basin configured to contain a volume of water. The spa shell 1010 is large enough to accommodate one or more persons therein. According to the example, the spa shell 1010 may include a reclined seating area 1011, on which a person may sit with his/her feet and legs in a reclined position, as well as a bench seating area 1012, upon which one or more persons may sit. The spa shell 1010 may also include a plurality of inlets, such as jet nozzles 1013, of varying types and arranged in varying configurations around the spa shell 1010.

As shown in FIG. 2, the spa tub 1000 also includes a circulation system 1020 in communication with the interior cavity of the spa shell 1010 to create a flow of the water to and from the interior cavity of the spa shell 1010. According to the example, the circulation system 1020 may include several components, such as one or more pumps, one or more water heaters, one or more filtering devices, one or more dispensers for cleaning agents and chemical treatment substances, and/or one or more dispensers for therapeutic or recreational substances (Epsom salts, herb salts, aromatherapy, etc.), as well as any required flow pipes or conduits, for creating the flow of water to and from the interior of the spa shell 1010 in a manner suitable for recreational or therapeutic use of the spa tub 1000. The spa shell 1010 may include a plurality of outlets (not shown) to allow water within the interior cavity of the spa shell 1010 to enter the circulation system 1020.

The circulation system 1020 is configured to direct water into the interior cavity of the spa shell 1010 via the inlets. In particular, the circulation system 1020 may be configured to pump water into the interior cavity via the jet nozzles to create a massaging or therapeutic spray of water into the interior cavity. The spa shell 1010 may include one or more waterfalls or other features that also dispense circulated water into the interior cavity. The spa tub 1000 may further include a drain 1014 allowing for the volume of water contained within the spa shell 1010 to be drained to a local sewage or septic system. The water testing system 10 may be in communication with the interior cavity of the spa shell 1010 by a system intake 64 to draw water from the spa shell 1010 into the water testing system 10 and a system discharge 65 to return water from the water testing system 10 to the interior cavity of the spa shell 1010. According to another example, the system discharge 65 might be connected directly to the drain 1014 so that water exposed to the reagent or reagents used by the water testing system 10 may be disposed of directly. According to another example, the water testing system 10 may be in separate fluid communication with the interior cavity of the spa shell 1010 and the drain 1014 so that water may be discharged to both the interior cavity and the drain 1014. According to another example, the water testing system 10 may be connected in communication with the circulation system 1020 so as to draw water into the water testing system 10 as the water is directed through the circulation system 1020 and may also return water to the circulation system 1020.

The spa tub 1000 may further include a spa controller 1040, such as a programmable microcontroller device, that is configured to transmit instructions to the components of the spa tub 1000, such as the circulation system 1020 and the water testing system 10, to control the operations of the spa tub 1000, and to receive inputs, such as sensor data and control inputs from a user or from the components of the spa tub 1000. The spa tub 1000 may include one or more auxiliary devices 1030, such as a control panel, lighting features, entertainment features (speakers, video display screens, etc.), or other features or devices provided to improve or facilitate use of the spa tub 1000. The spa controller 1040 may also be in communication with a communications device or devices 1050 for transmitting information (sensor data, water quality test results, etc.) regarding the spa tub 1000 to a remote location, such as a remote server or a personal device (phone, tablet, computer, etc.) of the user, and for receiving controls and instructions from the remote location. An example of a spa tub incorporating a spa controller, circulation system, auxiliary devices, and communications devices, as described above, is provided in United States Patent Application Publication No. 2019/0099325 (hereinafter "the '325 publication"), which is hereby incorporated by reference in its entirety. Further details regarding the connection of the spa controller 1040 to the water testing system 10 for transmitting instructions to the water testing system 10 and receiving information from the water testing system 10, including water quality test results, will be provided in further detail below with reference to FIGS. 20-22C.

It is to be appreciated that the spa tub 1000 shown in FIGS. 1 and 2 is of an exemplary configuration only and may be of any suitable configuration. It is further to be appreciated that the water testing system 10 provided herein may be used in connection with water recreation/therapy devices other than spa tubs. For instance, the water testing system 10 may be used in connection with a pool or bathtub incorporating an internal circulation system.

Water Testing System

With reference to FIGS. 1-6 and 13, the water testing system 10 is configured to acquire water samples from the volume of water within the spa tub 1000 and perform water quality tests on the water samples. According to an example, the water testing system 10 is configured to perform one or more tests for various water quality parameters, such as pH (acidity), total alkalinity, free chlorine, total chlorine, and/or total dissolved solids. The water testing system 10 includes the housing 11, the water test assembly 12 disposed in the housing 11, and a main pump 13 (shown in FIGS. 2 and 13). According to an example, the interior of the housing 11 of the water testing system 10 may be lined with insulative panels to maintain a temperature of the interior of the housing 11 and to maintain the temperature of the components of the water testing system 10 and the chemical reagents contained within the water testing system 10.

According to an example, the main pump 13 is provided outside the housing 11, though it is to be appreciated that the housing 11 may be configured to accommodate the main pump 13 within the housing 11. The main pump 13 is disposed downstream of the water test assembly 12 and is configured to draw a portion of the volume of water in the spa tub 1000 through the water testing system 10. According to an example, the water testing system 10 may also include a printed circuit board 25 incorporating a programmed microcontroller and power distribution circuits therein for controlling operations of the water testing system 10, receiving instructions from the spa controller 1040 or a remote server or device, and transmitting water quality test results to the spa controller 1040 or a remote server or device. Further details regarding the microcontroller of the water testing system 10 will be provided in further detail below with reference to FIGS. 18 and 20. A cord 21 is provided to connect the water testing system 10 to an external power supply. The cord 21 may also include communication wires for physically communicating the water testing system 10 to the spa controller 1040 or a separate communications device.

According to an example, the housing 11 of the water testing system 10 is disposed within the interior of the spa tub 1000. In particular, the housing 11 may be mounted within the frame or cabinet (not shown) of the spa tub 1000 under the spa shell 1010 and accessed via an access opening or door formed in the spa cabinet. According to another example, the water testing system 10 may be disposed within a recessed area formed in the spa shell 1010 and accessible from within the spa shell 1010 or the spa shell 1010 may incorporate an opening defined therein to allow for access to the water testing system 10 disposed within the frame or spa cabinet of the spa tub 1000 under the spa shell 1010. According to another example, the water testing system 10 is positioned in a recess or multiple recesses defined in a rim of the spa tub 1000 or under the spa shell 1010, and the spa tub 1000 includes a mechanism for raising and lowering the water testing system 10 to provide access to the water testing system 10 for maintenance and to allow replacement of the chemical reagents contained within the water testing system 10, as will be discussed below.

As shown in FIGS. 1-6, the water testing system 10 also includes a circulation pump 14 disposed within the housing 11. The circulation pump 14 is configured to acquire water samples from the volume of water in the spa tub 1000. According to an example, the circulation pump 14 is configured to acquire the water samples from the portion of the volume of water drawing through the water testing system 10 by the main pump 13. The water testing system 10 further includes the reagent cartridge 50 received within the housing 11. The reagent cartridge 50 includes the at least one pouch 51 for containing at least one chemical reagent for performing water quality tests on the water samples. According to an example, the reagent cartridge 50 is replaceable and is removably received within the housing 11. The water test assembly 12 is configured to receive the water samples acquired by the circulation pump 14 and the at least one chemical reagent from the reagent cartridge 50. The water test assembly 12 mixes the water samples and the chemical reagent, and performs the water quality tests on the mixed water samples and chemical reagent.

Reagent Dispensing and Circulation Systems

With reference to FIGS. 3-12, the water test assembly 12 includes a cartridge receiving portion 15 for receiving the reagent cartridge 50 and a durable or reusable test portion 40 for performing water quality tests on successive water samples acquired by the circulation pump 14. The reusable test portion 40 includes the least one test cell or test plate 110, also referred to herein as a plate assembly or water test device 110, for mixing the water samples with the chemical reagent(s) contained within the reagent cartridge 50 and performing the water quality tests on the mixed water samples and chemical reagent(s). According to an example, the reusable test portion 40 includes three water test devices 110. The water testing assembly 10 further includes a pump motor 24 for actuating mixing pumps associated with each of the water test devices 110 and a valve actuator motor 23 for rotating a valve actuator cam 28 associated with valve actuator plates 216 on each of the water test devices 110. Additional details regarding structure of the water test devices 110 and the operation of the water test devices 110 to mix the water samples with the chemical reagent(s) and perform the water quality tests is provided below with reference to FIGS. 16-19.

As shown in FIGS. 3-12, the reusable test portion 40 also includes at least one reagent dispenser 41 for accessing the at least one reagent in the at least one pouch 51 of the reagent cartridge and for distributing the at least one reagent within the reusable test portion 40. According to an example, the at least one pouch 51 is sealed and includes a sealable closure 52, such as a sealable stopper, a sealable membrane, or a plastic self-sealing septum, at an end thereof and the at least one reagent dispenser 41 includes a needle 43 that extends through the sealable closure 52 to establish fluid communication between the at least one reagent dispenser 41 and the interior of the at least one reagent pouch 51 and access the at least one reagent contained within the at least one reagent pouch 51. According to an example, the needle 43 is a non-boring needle or may be formed as a nozzle configured to be pushed through or penetrate through the sealable closure 52. The sealed configuration of the at least one reagent pouch 51 prevents air from entering the reagent pouch 51, which may cause premature oxidation and spoilage of the chemical reagent contained in the at least one reagent pouch 51. The sealable closure 52 is configured to seal around the needle 43 as the needle 43 is pushed through or penetrates the sealable closure 52 to maintain the sealed state of the at least one reagent pouch 51.

According to an example, the reagent cartridge 50 is removably received in the cartridge receiving portion 15. The reagent cartridge 50 and the cartridge receiving portion 15 are configured to align the at least one reagent pouch 51 with the at least one reagent dispenser 41. According to the example, the cartridge receiving portion 15 includes at least one recess 16 defined in a bottom surface that is aligned with the at least one reagent dispenser 41. The at least one recess 16 may include an opening 19 defined therein to allow the needle 43 of the at least one reagent dispenser 41 to extend into the recess 16 to engage the at least one reagent pouch 51. The at least one pouch 51 includes a spout 53 on an open end thereof. The sealable closure 52 is disposed in the spout 53. The spout 53 of the at least one reagent pouch 51 projects from a bottom side 56 of the reagent cartridge 50 and is configured to be received in the at least one recess 16 in the cartridge receiving portion 15 to align the spout 53 and the sealable closure 52 with the at least one reagent dispenser 41.

According to an example, the reagent cartridge 50 includes a plurality of reagent pouches 51 disposed within an interior of the cartridge 50. Each reagent pouch 51 contains a respective chemical reagent. The reusable test portion 40 includes a plurality of reagent dispensers 41 for accessing each of the reagents in the plurality of pouches 51 and distributing the reagents within the reusable test portion 40. The reagent cartridge 50 and the cartridge receiving portion 15 are configured to align the plurality of reagent pouches 51 with a respective one of the reagent dispensers 41.

As shown in FIGS. 6 and 9-12, the reagent cartridge 50 contains five reagent pouches 51 each containing a respective chemical reagent for conducting water quality tests. The reusable test portion 40 includes five reagent dispensers 41 for accessing and dispensing the contents of each of the five reagent pouches 51. Each reagent pouch 51 includes a spout 53 on an open end thereof that projects from the bottom side 56 of the reagent cartridge 50. Each spout 53 includes a sealable closure 52 on an end thereof to allow for the needle or nozzle 43 of the respective reagent dispenser 41 to extend through the sealable closure 52 to access the interior of the reagent pouch 51 and the chemical reagent contained in the reagent pouch 51. The cartridge receiving portion 15 includes five recesses 16 defined in the bottom side 56 thereof, each recess 16 is configured to receive the spout 53 of a respective reagent pouch 51 to align the spout 53 of the reagent pouch 51 with the respective reagent dispenser 41. Each recess 16 includes an opening 19 to allow for the needle 43 of the respective reagent dispenser 41 to extend into the recess 16 to access the respective reagent pouch 51. According to an example, the reagent cartridge 50 and the cartridge receiving portion 15 are configured such that all five reagent dispensers 41 engage the respective five reagent pouches 51 at the same time when the reagent cartridge 50 is fully inserted into the cartridge receiving portion 15.

According to an example, the chemical reagents contained in the reagent pouches 51 are in liquid form. According to another example, the chemical reagents may instead be provided in a tablet or powder form encapsulated within the reagent pouches 51 in a sealed wrapper or container to preserve the chemical reagent in a dry condition. The reagent pouches 51 may contain water or another solvent surrounding the sealed wrapper or container. When the needle 43 of the respective reagent dispenser 41 penetrates the sealable closure 52 of the reagent pouch 51, the needle 43 also breaks the wrapper or container surrounding the chemical reagent, thereby allowing the chemical reagent to be dissolved by the water or solvent contained within the reagent pouch 51 for distribution to the water test assembly 12 by the respective reagent dispenser 41. According to such an example, the overall shelf life of the chemical reagents within the reagent cartridge 50 may be extended because the sealed, solid chemical reagents are less likely to oxidize or become heat damaged than a liquid reagent.

Figure 10:
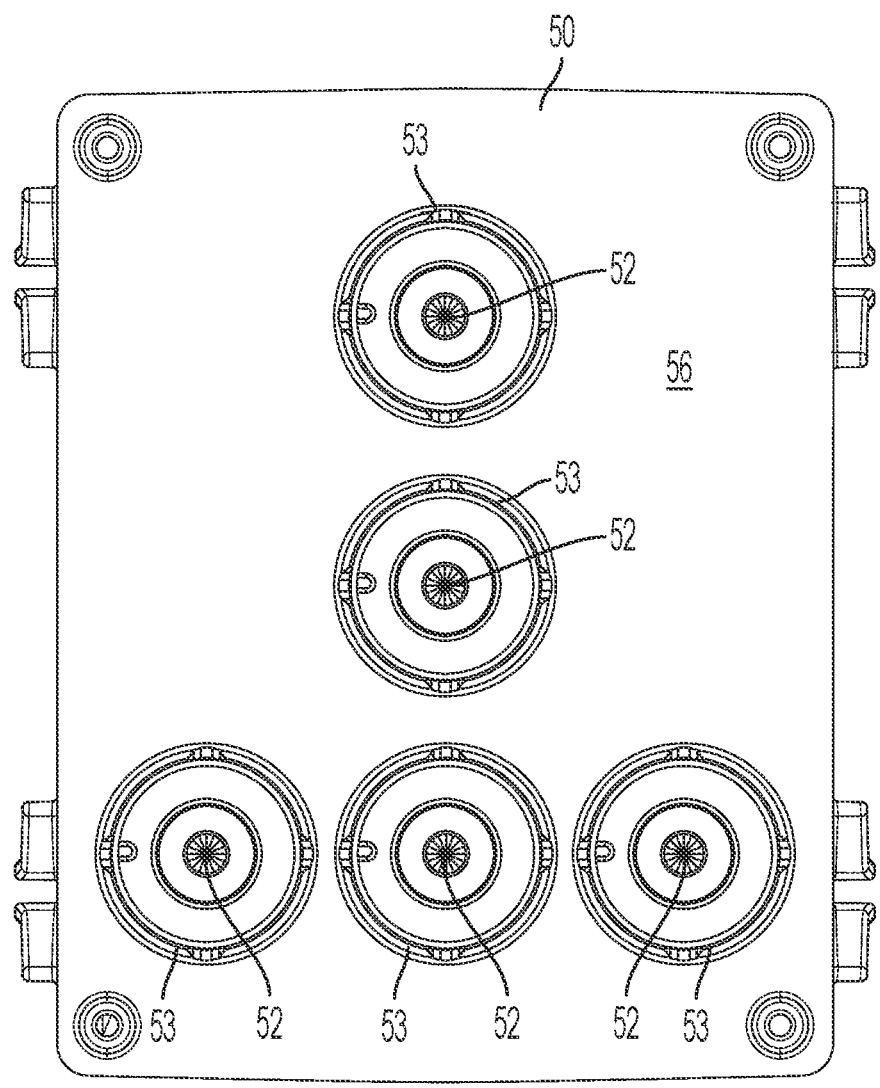
FIG. 10 is a bottom view of the reagent cartridge of FIG. 9.
Figure 11:
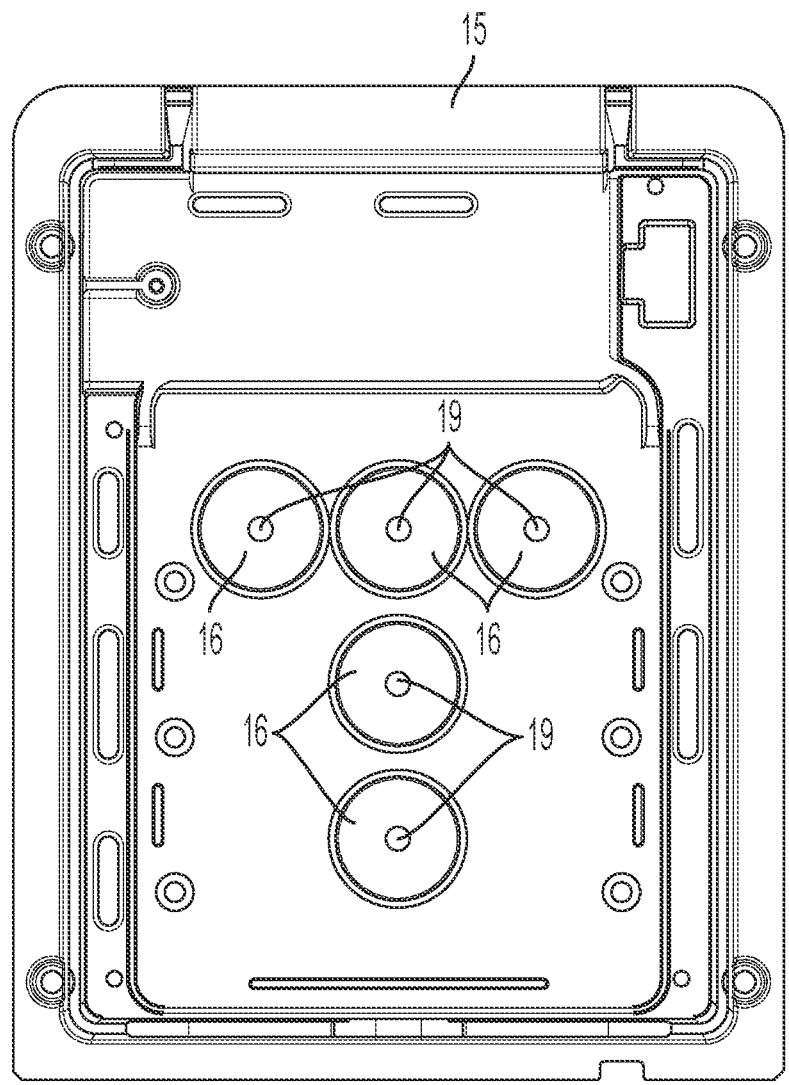
FIG. 11 is a top view of a cartridge receiving portion of the water test assembly of FIG. 7.
Figure 12:
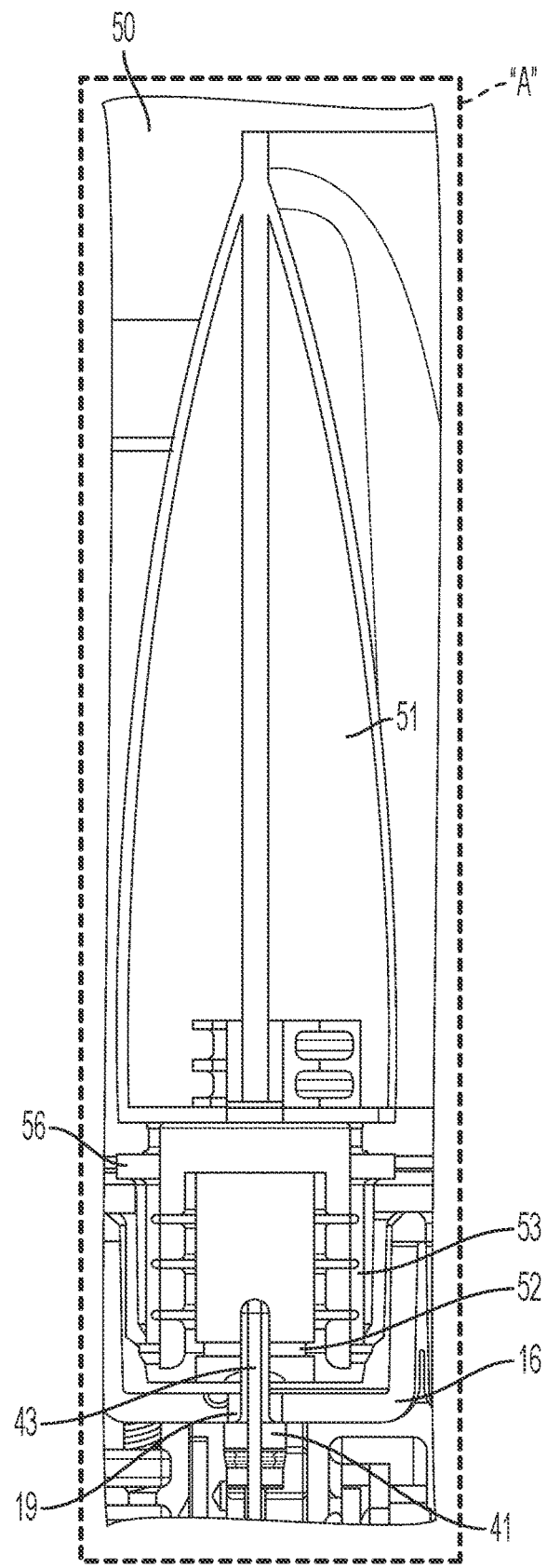
FIG. 12 is an enlarged cross-sectional view of the reagent cartridge and water test assembly taken from area "A" shown in FIG. 6.
Figure 13:
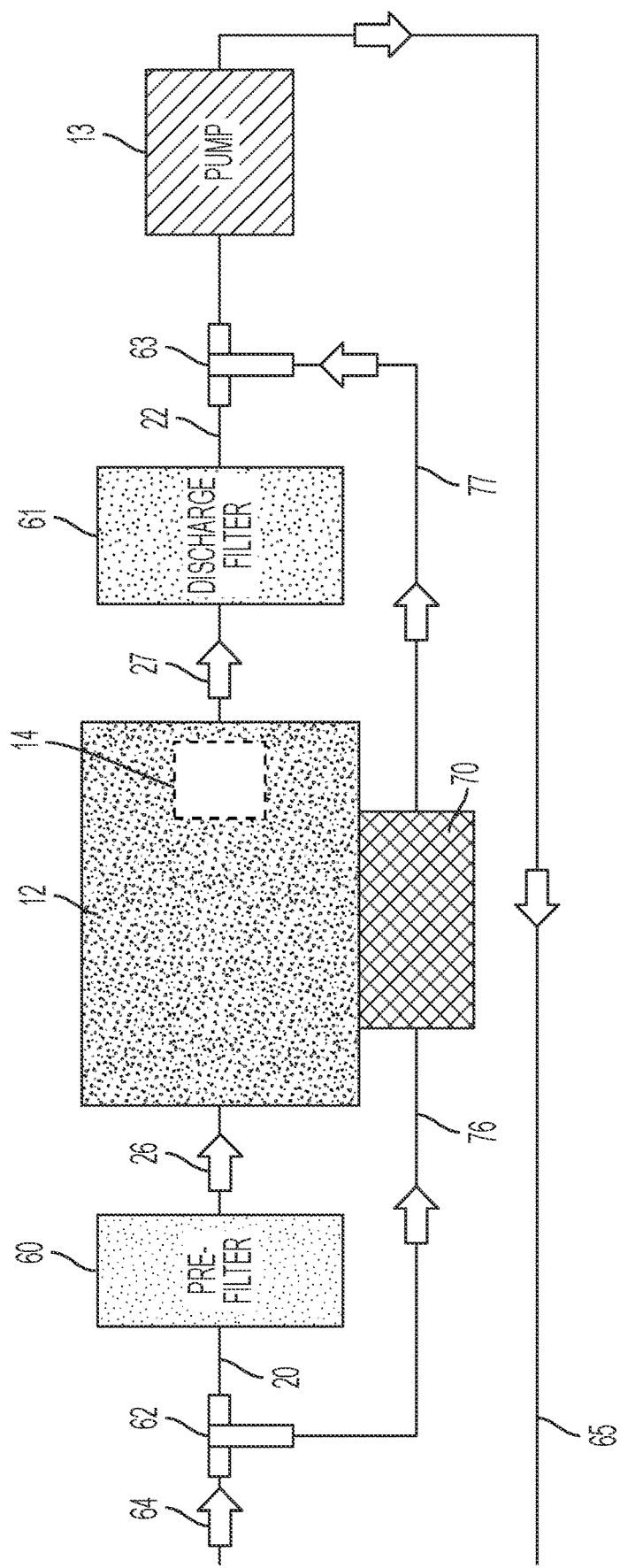
FIG. 13 is a schematic of the fluid connections of the water testing system of FIG. 1 according to an example of the present disclosure.

According to one example, as shown in FIGS. 10 and 11, the reagent pouches 51 are arranged in a "T" shape in the reagent cartridge 50, such that three of the reagent pouches 51 and spouts 53 are aligned across the width of the reagent cartridge (horizontal direction in FIG. 10) and three of the reagent pouches 51 and spouts 53 are aligned along the length of the reagent cartridge (vertical direction in FIG. 10). The recesses 16 in the cartridge receiving portion 15 are correspondingly arranged, as shown in FIG. 11. The respective reagent dispensers 41 associated with each of the reagent pouches 51 may be configured to dispense the chemical reagents to a single one of the water test devices 110 of the reusable test portion 40 or may be connected with more than one of or all of the water test devices 110 to dispense the chemical reagents to the water test devices 110. It is to be appreciated that reagent pouches 51, reagent dispensers 41, and water test devices 110 may be connected and arranged with respect to each other in any suitable manner.

With reference to FIGS. 3-11, the reagent receiving portion 15 defines an interior cavity with an open top configured such that the reagent cartridge 50 may be top-loaded within the cartridge receiving portion 15. According to an example, the reagent cartridge 50 and the cartridge receiving portion 15 are configured to avoid incorrect insertion of the reagent cartridge 50 in the cartridge receiving portion 15. According to the example, the reagent cartridge 50 and the reagent receiving portion 15 may be shaped such that the reagent cartridge can only be appropriately inserted and aligned in the cartridge receiving portion 15 in the correct orientation. Additionally, the spouts 53 of the reagent pouches 51 and recesses 16 in the cartridge receiving portion 15 are arranged such that there is only one orientation of the reagent cartridge 50 with respect to the cartridge receiving portion 15 that will allow for the spouts 53 and the recesses 16 to be correctly aligned. According to the example, the reagent cartridge 50 may include a graspable portion 54 defined in the top side 55 of the reagent cartridge 50 to facilitate handling by the owner/user by allowing the owner/user to easily grasp the reagent cartridge 50 for insertion and removal in the cartridge receiving portion 15. The reagent cartridge 50 may further include indicia formed in or printed on the sides of the reagent cartridge 50 that indicate to the user/owner the correct orientation for insertion of the reagent cartridge 50 in the cartridge receiving portion 15.

According to an example, the reagent cartridge 50 is configured to contain reagent pouches 51 containing the chemical reagents for conducting all of the water quality tests performed by the water testing system 10. The reagent cartridge 50 is configured to be replaced by the user several times a year.

Figure 3:
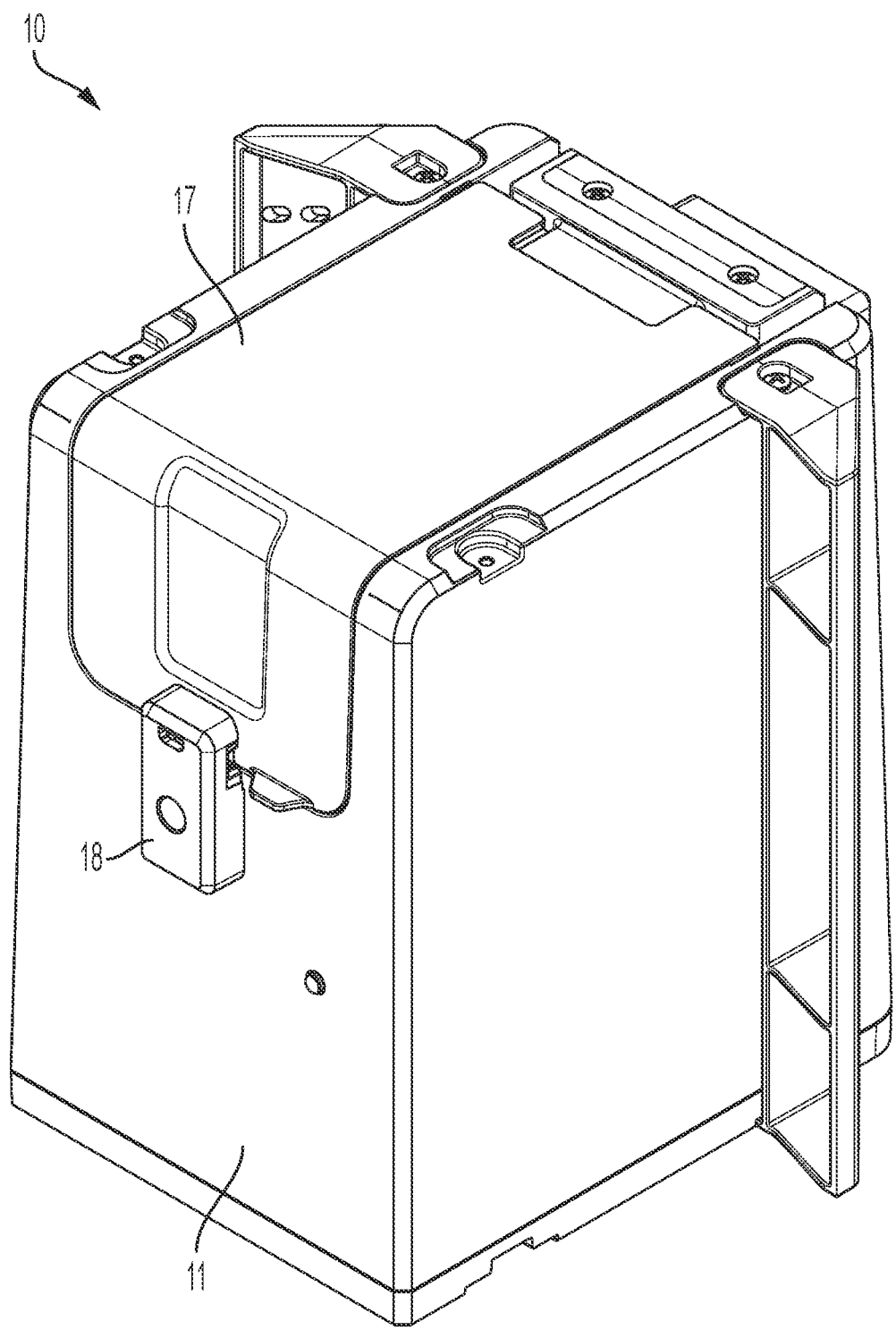
FIG. 3 is a front perspective of the water testing system of FIG. 1.
Figure 4:
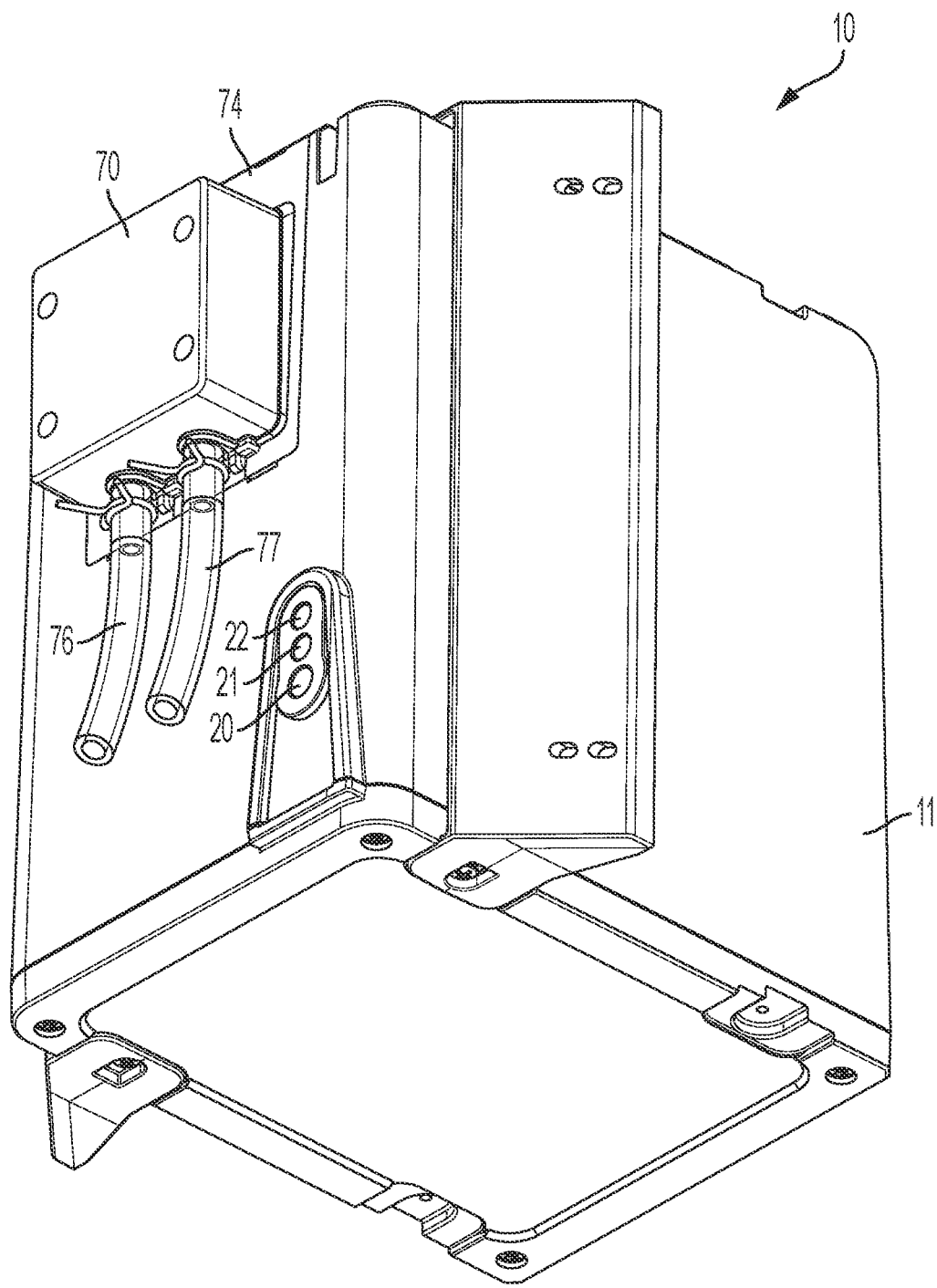
FIG. 4 is a rear perspective view of the water testing system of FIG. 1.
Figure 5:
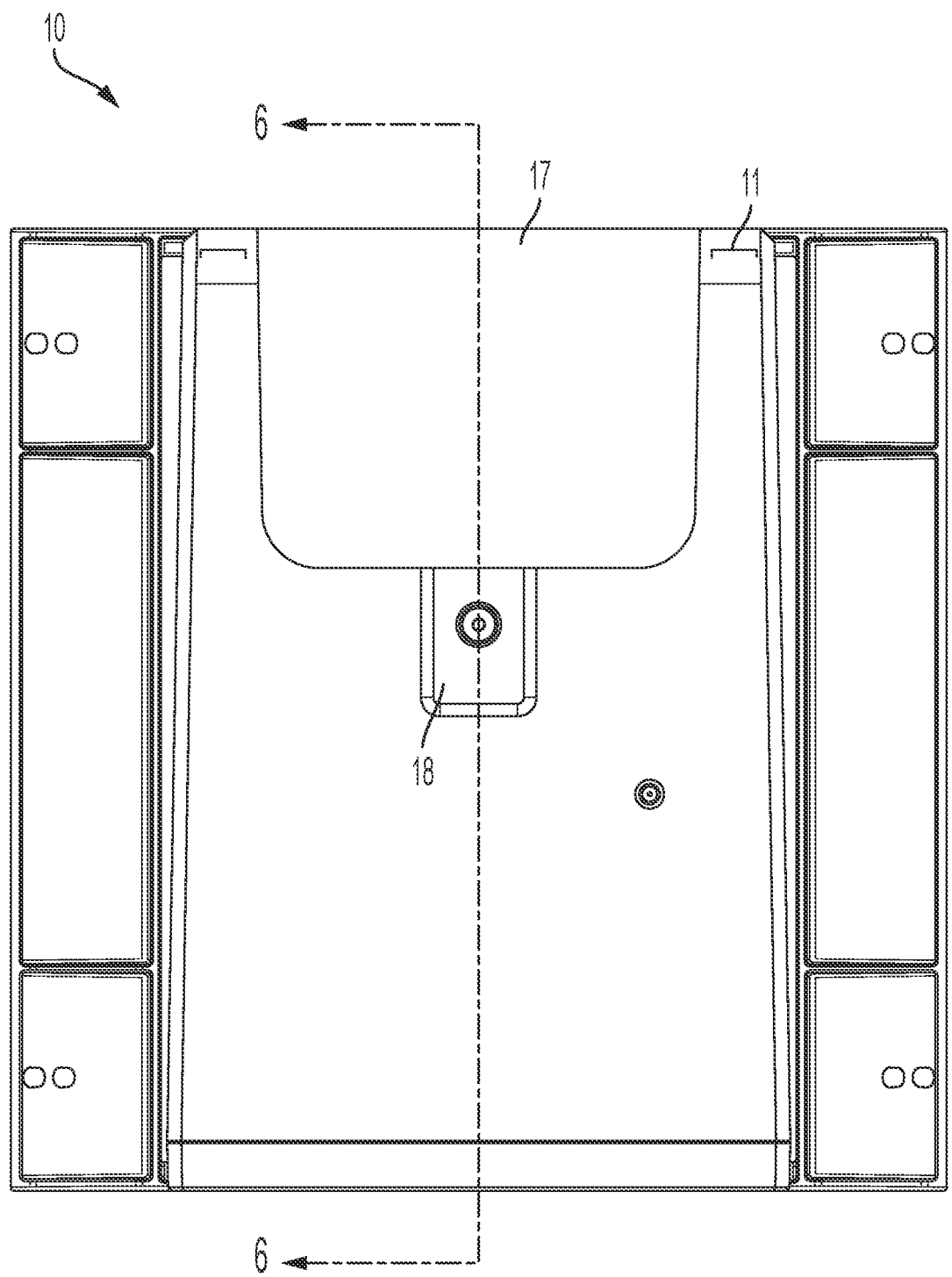
FIG. 5 is a front elevation view of the water testing system of FIG. 1.
Figure 6:
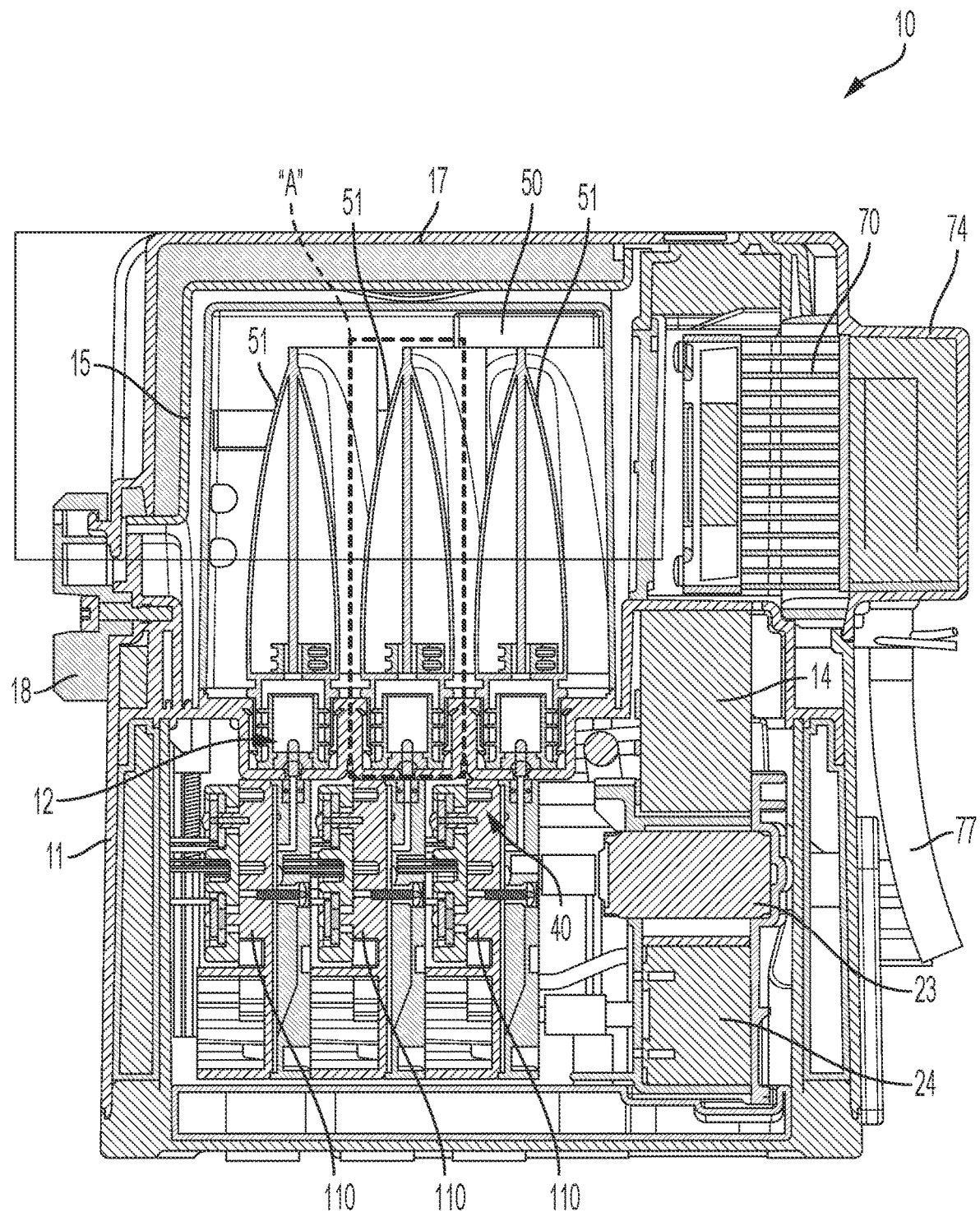
FIG. 6 is a cross-sectional view of the water testing system of FIG. 1 taken along lines 6-6 shown in FIG. 5.

As shown in FIGS. 3, 5, and 6, the housing 11 of the testing system 10 may include a door 17 hingedly connected to a top of the housing 11 to provide access to the cartridge receiving portion 15 and allow the reagent cartridge 50 to be inserted into and removed from the cartridge receiving portion 15 by the owner/user. The door 17 may be opened to allow access to the cartridge receiving portion 15 and closed to shut the housing 11. The housing 11 may further include a latch 18 on a side thereof to secure the door 17 in the closed position. According to an example, the door 17 includes insulation material on an inside surface thereof and is configured to seal the housing 11 when in the closed position.

Figure 9:
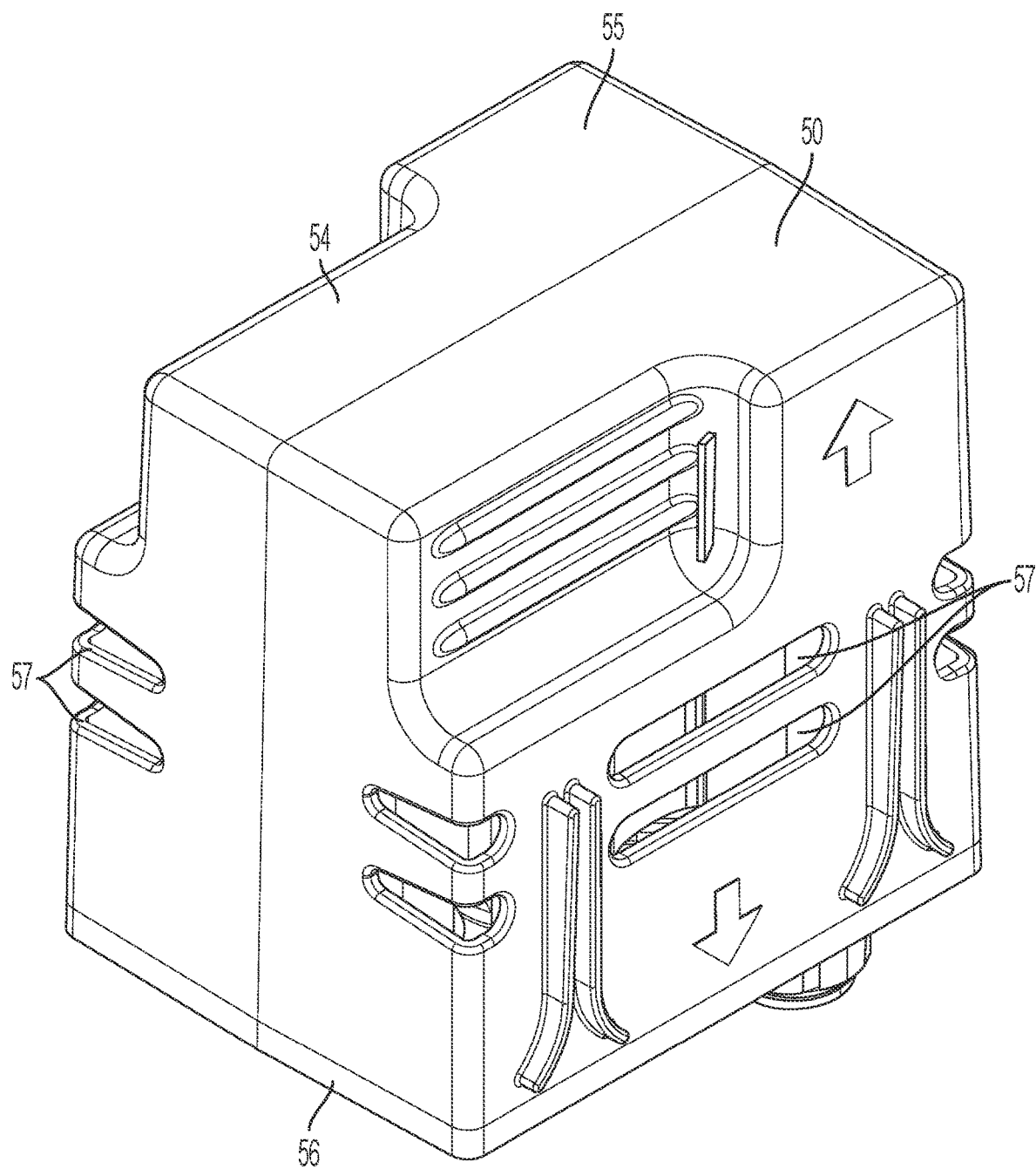
FIG. 9 is a perspective view of a reagent cartridge of the water testing system of FIG. 1 according to an example of the present disclosure.

As shown in FIG. 9, the reagent cartridge 50 may also include vent openings 57 defined in the sides thereof. The vent openings 57 allow for circulation of air through the cartridge to maintain a temperature of the chemical reagents contained within the pouches 51. The testing system 10 may incorporate various features for cooling and cycling air within the housing 11 of the testing system 10, as will be discussed below, or distributing cooling air from outside the spa tub 1000 into the housing 11 of the water testing system 10.

Temperature Control/Cooling Assembly

With reference to FIGS. 4, 6, and 13-15, the testing system 10 may further include a cooling assembly 70 that is provided to maintain a temperature of the reagent cartridge 50 and the chemical reagents contained within the reagent cartridge 50. The cooling assembly 70 is disposed on a bracket 74 fastened to the housing 11. The cooling assembly 70 is in fluid communication between the system intake 64 of the testing system 10 and the main pump 13 of the testing system 10 such that the portion of the volume of water drawn through the testing system 10 by the main pump 13 is directed through the cooling assembly 70. The cooling assembly 70 is configured to transfer heat from the interior of the housing 11 of the water testing system 10 to the portion of the volume of water directed through the cooling assembly 70. In particular, the cooling assembly 68 includes a thermoelectric cooling device 78, such as a Peltier device. The thermoelectric cooling device 78 includes a "cool" side facing inwards toward the interior of the housing 11 and the reagent cartridge 50 and a "hot" side facing towards a water block 71 that channels the portion of the volume of water past the thermoelectric cooling device 78 such that the heat generated by the thermoelectric cooling device 78 is transferred to the portion of the volume of water flowing through the cooling assembly 70.

The chemical reagents contained in the reagent cartridge 51 may be subject to premature oxidation or spoilage when exposed to high temperatures. Accordingly, the cooling assembly 70 is configured to maintain a temperature within the housing 11 of the water testing system 10 below a maximum temperature where the chemical reagents are subject to premature oxidation or spoilage and thereby maintain the chemical stability of the reagents. The volume of water contained within the spa tub 1000 is typically maintained at a temperature of approximately 100° F. to 105° F. (37.8° C. to 40.6° C.) that is less than the temperature of the air within the cabinet of the spa tub 1000 below the spa shell 1010, which can reach between 120° F. and 140° F. (48.9° C. and 60° C.).

The high temperature of the cabinet of the spa tub 1000 allows for the water to be utilized as an effective cooling medium for the thermoelectric cooling device 78. This is because the temperature of the volume of water within the spa tub 1000 is significantly closer to the temperature of the air within the cabinet of the spa tub 1000 than ambient air (~75° F./23.9° C.).

Most thermoelectric cooling devices have a maximum temperature differential ($\Delta T$) at which they can effectively transfer heat to a cooling medium. If ambient air were to be used as a cooling medium, the temperature differential ($\Delta T$) between the interior of the cabinet of the spa tub 1000 and the ambient air would be approximately 45° F.-65° F. (25° C.-36.1° C.), which is beyond the maximum ($\Delta T$) for a typical thermoelectric cooling device, thus necessitating that multiple thermoelectric cooling devices be provided to maintain the temperature of the interior of the housing 11. The temperature differential ($\Delta T$) between the volume of water in the spa tub 1000 and the interior of the cabinet of the spa tub 1000 is approximately 15° F.-40° F. (8.3° C.-22.2° C.), which allows for a single thermoelectric cooling device to effectively transfer the heat. This makes the use of the thermoelectric cooling device 78 more feasible and requires less power consumption by the thermoelectric cooling device 78. According to an example, the thermoelectric cooling device 78 is a 50-70 Watt thermoelectric cooling device utilizing the Peltier Effect. The thermoelectric cooling device 78 is powered through the circuit board 25.

Figure 14:
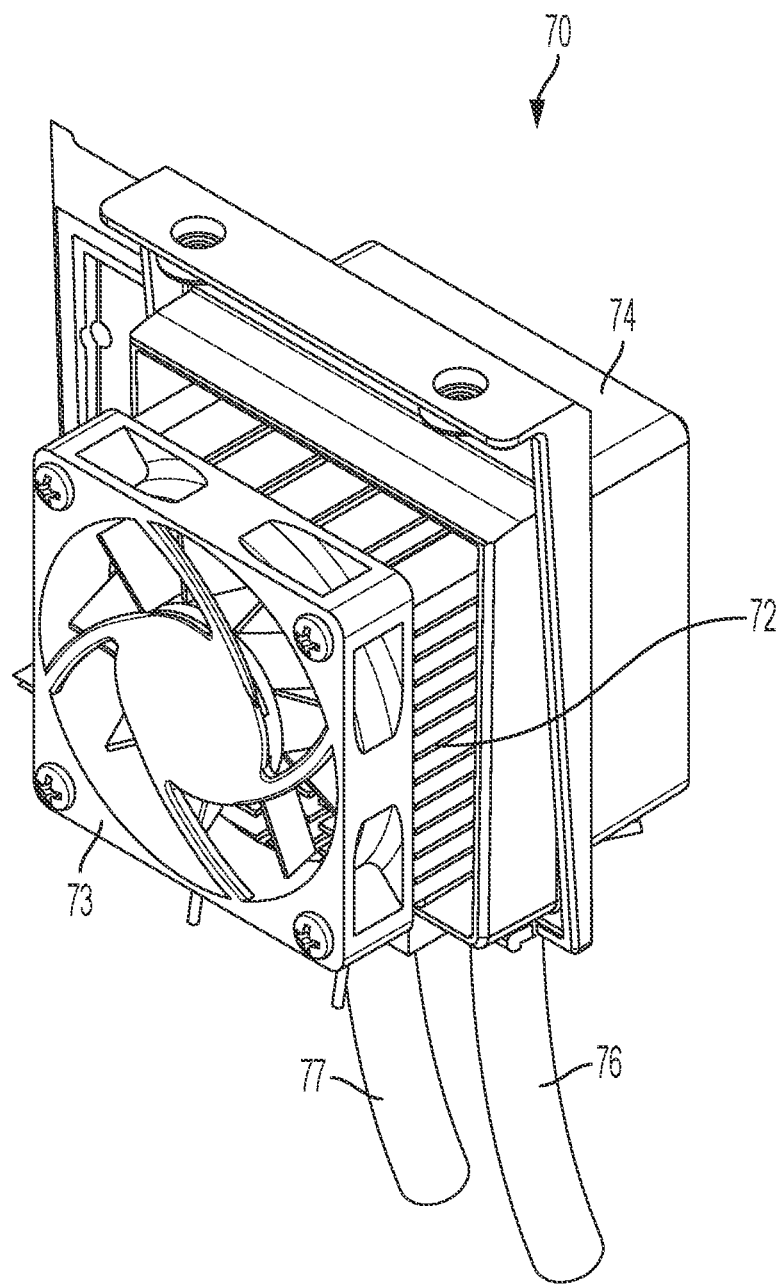
FIG. 14 is a front perspective view of a cooling assembly of the water testing system of FIG. 1, according to an example of the present disclosure.
Figure 15:
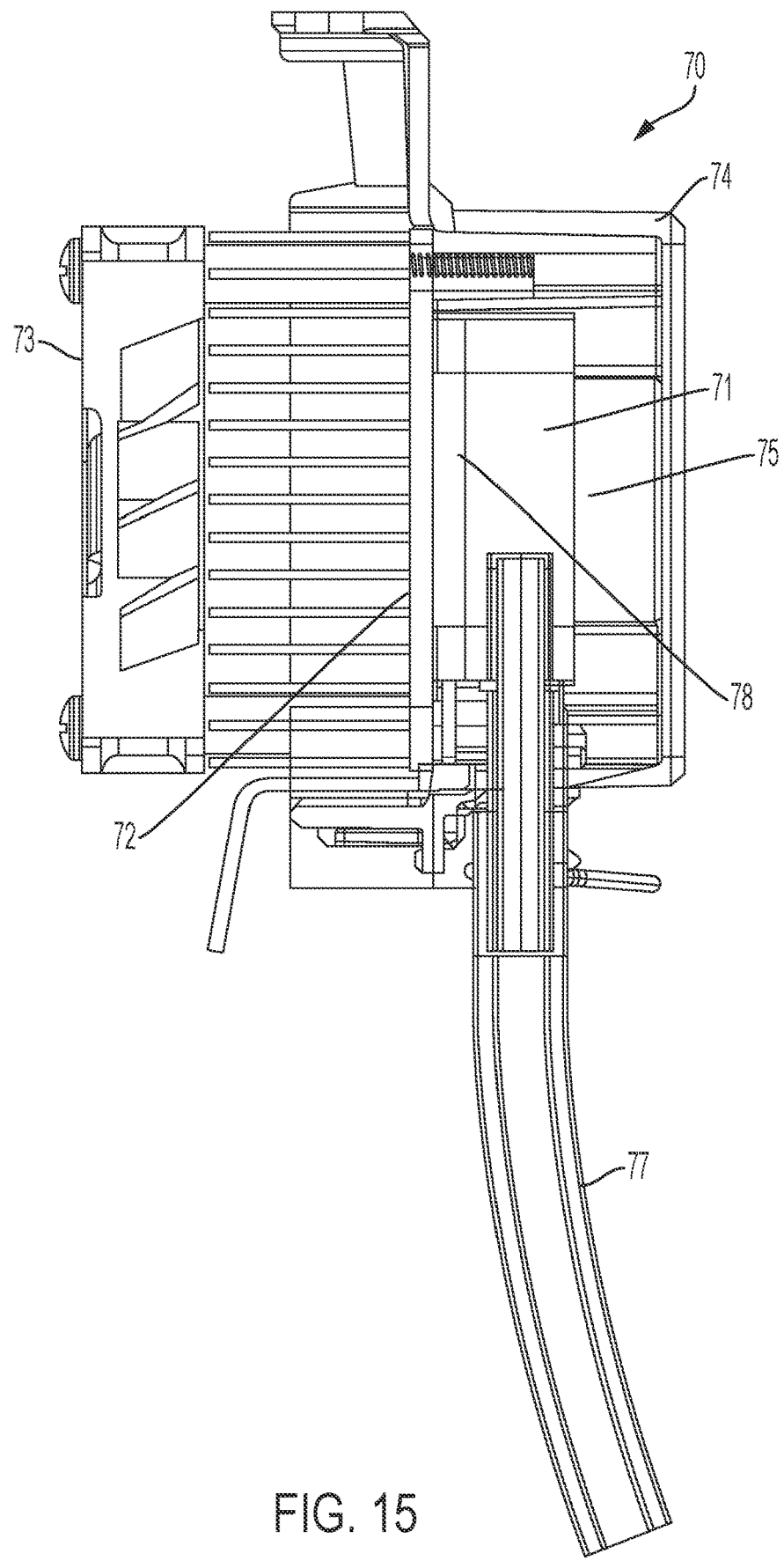
FIG. 15 is a cross-sectional view of the cooling assembly of FIG. 14.

As shown in FIGS. 14 and 15, the cooling assembly 70 includes the thermoelectric cooling device 78 and the water block 71 disposed within the bracket 74. The water block 71 is connected to the system intake 64 of the testing system 10 by an intake line, conduit, or hose 76 and to the main pump 13 by an outlet line, conduit, or hose 77 so that the portion of the volume of water drawn by the main pump 13 is received and channeled by the water block 71. The water block 71 is surrounded by insulation 75 within the bracket 74 to maintain the temperature of the water block 71 with respect to the interior of the cabinet of the spa tub 1000.

The cooling assembly 70 also includes a heat sink 72, which may be made from an aluminum material and is configured to be cooled by the thermoelectric cooling device 78, and a fan 73 configured to circulate air within the housing 11 of the testing system 10 and, particularly, direct cooled air from across the heat sink 72 towards the reagent cartridge 50. The fan 73 and fins of the heat sink 72, which extend away from the "cool" side of the thermoelectric cooling device 78, are positioned in the housing 11 adjacent to or in close proximity with the reagent cartridge 50 and facing toward the reagent cartridge 50. The plate portion of the heat sink 72 is positioned adjacent to the "cool" side of the thermoelectric device 78 such that "cool" side of the thermoelectric cooling device 78 cools the heat sink 72 and/or absorbs heat from the heat sink 72. Accordingly, as the fan 73 is activated to recirculate air within the housing 11, the fan 73 draws air within the housing 11 across the fins of the cooled heat sink 72, which cools the circulating air. The cooled air is then blown by the fan 73 towards the reagent cartridge 50 and into the interior of the reagent cartridge 50 via the vent openings 57.

According to an example, controller 232 (shown in FIG. 21) of the testing system 10 is connected to temperature sensors within the housing 11 and is configured to monitor the temperature of the interior of the housing 11 and operate the cooling assembly 70 to maintain the temperature of the interior of the housing 11 below a threshold maximum temperature; i.e., a closed loop control system. The main pump 13 is simultaneously operated to draw the portion of volume of water through the cooling assembly 70. According to an example, the cooling assembly 70 is configured to maintain a temperature of the interior of the housing between approximately 32° F. and 100° F., more particularly between approximately 45° F. and 85° F. According to an example, the interior of the housing 11 of the water testing system 10, including the interior side of the door 17 for accessing the cartridge receiving portion 15, has a layer of insulation disposed thereon to help maintain the temperature of the interior of the housing 11 with respect to the interior of the cabinet of the spa tub 1000.

According to another example, the thermoelectric cooling device 78 may include a compressor to provide the cooling. According to an example, the testing system 10 may include a cooling fan with ductwork installed on a wall of the cabinet of the spa tub 1000 that pumps ambient air from outside of the spa tub 1000 onto or through the housing 11 of the testing system 10. The cooling fan may be subject to the same closed loop control based on a maximum allowable temperature within the housing 11 as described above. This configuration reduces heat flow into the insulated interior of the housing 11 by reducing the temperature differential (ΔT) across the insulation within the housing 11.

Water Circulation and Filtration Systems

With reference to FIGS. 4, 7, 8, and 13, as discussed above, the main pump 13 of the testing system is disposed downstream of the water test assembly 12 within the housing 11 and the cooling assembly 70 and draws a portion of the volume of water within the spa tub 1000 into the water testing system 10 through the system intake 64. According to an example, the main pump 13 is configured to draw approximately 1-4 liters per minute, more particularly approximately 2-3 liters per minute, and more particularly approximately 2.8 liters per minute through the water testing system 10 for purposes of testing and cooling of the water testing system 10 by the cooling assembly 70. The system intake 64 ends in a T-fitting 62 that joins the system intake 64 to a water inlet conduit 20 leading into the housing 11 and the intake line 76 of the cooling assembly 70.

Water quality tests may be conducted by the testing system 10 a few times a day. When water quality tests are to be performed, the circulation pump 14 in the housing 11 is activated to acquire the water samples from the portion of the volume of water drawn through the testing system 10 by the main pump 13 and draw the water samples into the water test assembly 12 via the water inlet conduit 20. According to an example, the size of the water samples acquired by the circulation pump 14 is minimal compared to the portion of the volume of water drawn by the main pump 11. The circulation pump 14 may only be activated to draw water into the water test assembly 12 when water quality tests are to be performed. The circulation pump 14 may draw some additional water through the water test assembly 12 to flush out the mixed reagent and water samples contained within the water test devices 110 before and/or after the water quality tests are performed. An inlet tube 26 is connected to the water inlet conduit 20 within the housing 11 and is connected to each of the water test devices 110 to direct the water samples into the water test devices 110 as needed. According to an example, the circulation pump 14 is configured to draw approximately 10-40 mL per minute, more particularly 20-30 mL per minute, and more particularly approximately 25 mL per minute of water into and through the water test assembly 12 for purposes of performing the water quality tests.

A pre-filter 60 may be disposed within the water inlet conduit 20 and/or the inlet tube 26 to filter particulate matter or debris and other contaminants from the water samples acquired by the circulation pump before the water samples are drawn into the water test devices 110 to avoid clogging of the fluid passages within the water test devices 110. When water quality tests are not being performed, the portion of the volume of water drawn through the water testing system 10 may entirely be directed through the cooling assembly 70 to maintain the temperature of the chemical reagents in the reagent cartridge 50.

According to an example, the circulation pump 14 is disposed downstream of the water test assembly 12 and draws the water samples through water test devices 110, as well as a sufficient amount to flush out the water test devices 110. The circulation pump 14 is connected to the water test devices 110 by a discharge tube 27. After the water quality tests are performed in the water test devices 110, the mixed reagents and water samples are also drawn from the water test devices 110 by the circulation pump 14. The circulation pump 14 then directs the water out of the housing 11 through a water discharge conduit 22.

The mixed water samples and chemical reagents drawn from the water test devices 110 or water test devices 110 cannot be directly re-circulated to the spa shell 1010, because the chemical reagents may be irritating or unhealthy for users of the spa tub 1000 and/or may result in discoloration of the volume of water contained in the spa tub 1000 and/or discoloration of the materials of the spa shell 1010. Additionally, local ordinances may not allow for passing of the mixed water and chemical reagents to the drain 1014 and the local sewage system. Further, the spa tub 1000 may not be installed in a location that would allow for the mixed water and chemical reagents to be disposed of on the surrounding ground area.

According to an example, the testing system 10 also includes a discharge filter 61 positioned downstream of the water test devices 110 of the water test assembly 12. The discharge filter 61 may be positioned in the discharge tube 27 between water test devices 110 and the circulation pump 14, in the water discharge conduit 22, or may be disposed within the circulation pump 14. The discharge filter 61 may be multilayered and is configured to remove or at least partially remove the chemical reagents from the water samples or significantly reduce the amount of reagents contained in the water samples after the water quality tests are performed, which would allow for the water drawn through the water test assembly 12 to be re-circulated to the spa tub 1000 or directed to the drain 1014. According to an example, the discharge filter 61 includes an activated carbon layer and an ion exchange resin layer. The discharge filter 61 may also include an oxidation reduction alloy layer. The discharge filter 61 may additionally include a distributor configured to evenly distribute the water passing through the discharge filter 61 across the discharge filter 61.

The water discharge conduit 22 from the housing 11 and the outlet line 77 from the cooling assembly 70 are connected to a T-fitting 62 positioned upstream of the main pump 13 such that the portion of the volume of water drawn through the water test assembly 12 and the cooling assembly 70 can be directed out of the testing system 10 by the main pump 13 and into the system discharge 65 to return the portion of the volume of water to the spa shell 1010 and/or the circulation system 1020 or to the drain 1014, as discussed above. The testing system 10 is configured such that the portion of the volume of water drawn through the cooling assembly 70 to provide cooling for the interior of the housing 11 and the reagent cartridge 50 bypasses the water test assembly 12. Accordingly, the water drawn through the cooling assembly 70 does not require filtering for debris and reagents, which preserves the operational lifetime of the filters 60, 61. This also allows for reduction of the size of the conduits and tubes 20, 22, 26, 27 in the housing 11 and of the filters 60, 61, and allows for a smaller circulation pump 14 to be provided, requiring less power to draw the water samples and flushing water through the water test assembly 12, since the amount of water used to conduct the water quality tests and to flush the water test devices 110 can be very small compared to the amount of water drawn through the cooling assembly 70 to effectively cool the interior of the housing 11 and the reagent cartridge 50. The configuration of the main pump 13 and the cooling assembly 70 also allows for the water samples used to conduct the water quality tests to be drawn near the water testing assembly 12 such that the size and power needs of the circulation pump 14 can be reduced and so that separate connections from the spa tub 1000 to the water testing assembly 12 do not need to be established to conduct the water quality tests.

According to an example, the water discharge conduit 22 from the housing 11 is not connected to the T-fitting 63 and is instead connected directly to the drain 1014 such that the water drawn through the water test assembly 12 can be disposed of, while allowing for the water drawn through the cooling assembly 70, which has not been exposed to the chemical reagents, to be re-circulated to the interior of the spa shell 1010 by the main pump 13.

Water Test Device or Test Plate

Having described components of the spa 1000 and water test system 10, features of the test plate assemblies or water test devices 110 will now be described in detail. As previously explained, the water test device 110 or test plates 110 are components of the water test assembly 12 and contained in the housing 11. Water samples are delivered to the water test assembly 12 by the circulation system and main pump 13.

Figure 7:
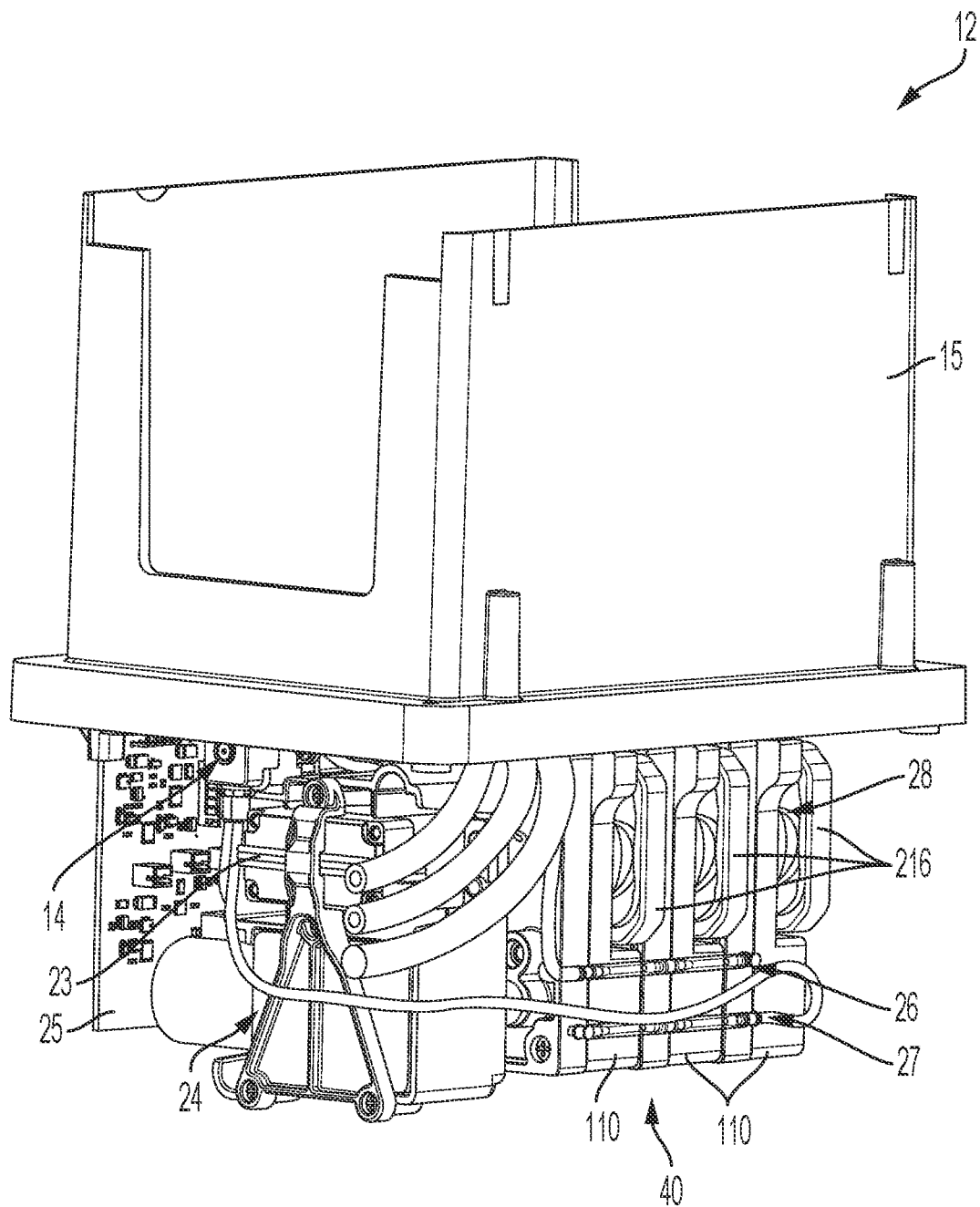
FIG. 7 is a rear perspective of a water test assembly of the water testing system of FIG. 1.
Figure 8:
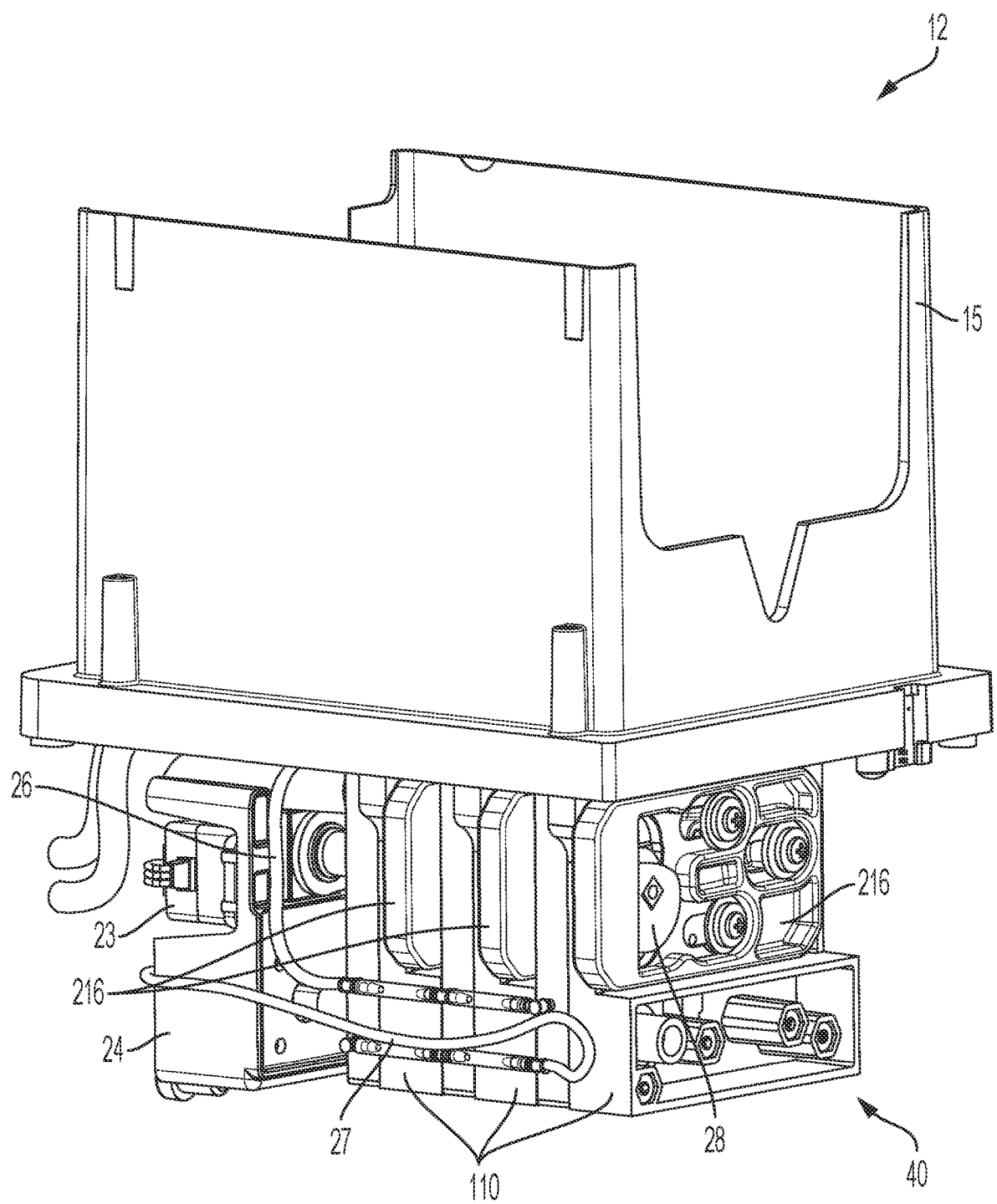
FIG. 8 a front perspective view of the water test assembly of FIG. 7.

The water samples are distributed through the water test assembly 12 to one or more water test devices 110 or test plates 110 of the water test assembly 12 by a manifold and water inflow line 112 (shown in FIGS. 7 and 8). In this way, water samples to be tested can be provided to the water test devices 110 directly from the spa 1000. As used herein, a water sample is "provided directly" to the water test device 110 when the spa 1000 includes mechanical components for delivering the water sample, and wherein delivery of the water sample to the water test device 110 can occur automatically. For example, the user does not need to draw water from the spa 1000, place a test strip in water from the spa 1000, or perform any other action for testing water in the spa 1000. Further, the user does not need to activate or actuate an electronic device to perform water testing. Instead, testing is initiated and performed automatically by the water test device 110.

In some examples, water from the spa 1000 is also used for cleaning, flushing, or purging remaining reagent from the water test devices 110 before or after testing so that the water test devices 110 can be reused. In some examples, the water test assembly 12 contains or comprises multiple test devices 110 or test plates mounted in the housing 11 that can be connected together, controlled, and operated using the same components (e.g., the same motors, water circulation pump, and/or control circuitry). For example, as shown in FIGS. 7 and 8, the water test assembly 12 includes three water test devices 110 connected together in series. The water test devices 110 are connected to the water inflow line 112, which is in turn connected to the inlet tube 26, for introducing the water from the spa 1000 to the water test devices 110. As previously described, the water test assembly 12 can also include a pump, such as the circulation pump 14, for drawing water into the water test assembly 12 and for circulating the water through the test assembly 12. The circulation pump 14 can also expel water from the water test assembly 12 after testing. For example, the circulation pump 114 can move the water to the drain 1014 of the spa 1000 or to a waste receptacle 118 of the testing system 10 and/or spa 1000.

As described herein, the water test devices 110 or test plates 110 are configured to be connected to the reagent sources (e.g., the reagent cartridge 50) for introducing the reagent to the water test devices 110 for optical reagent testing. In some examples, a vent can be provided in fluid communication with the reagent sources. The vent is optional and may not be provided where it is undesirable for the reagent to be exposed to oxygen. A vent 178 (shown in FIG. 16) may also be provided on the mixing chamber 130 for removing an air bubbles from the mixing chamber 130 during mixing of the chemical reagents and water samples.

With reference to FIGS. 16, 17A, and 18A-18D, the water test device 110 includes a base plate 120 or substrate, which can be substantially square or rectangular in shape. The base plate 120 can be a rigid structure having a top surface 122, an opposing bottom surface 124, and a peripheral edge 125 extending between the top surface 122 and the bottom surface 124. The base plate 120 can be formed from a substantially clear or transparent material, such as an acrylic material, to minimize light loss for light passing through portions of the base plate 120. As used herein, "substantially clear" or "substantially transparent" refers to a material that is sufficiently clear or transparent so that light from a light source 126 can pass through portions of the base plate 120 to be used for sensing water quality parameters of a water sample being tested by the water test device 110. In particular, the base plate 120 should be formed from a material that is clear or transparent enough so that coloration of the base plate 120 does not substantially affect light passing through portions of the base plate 120 and does not reduce accuracy of measurements obtained from a sensor 128 configured to detect light transmitted through or reflected from portions of the base plate 120.

The water test device 110 also includes a mixing chamber 130 on the base plate 120 having a water sample port 132, one or multiple reagent ports 134, and a drain port 136. As shown, for example, in FIGS. 18A-18D, the mixing chamber 130 includes one water sample port 132 and one drain port 136. The mixing chamber 130 includes three reagent ports 134, one port for each of the three types of reagents (referred to as Reagent 1, Reagent 2, and Reagent 3) connected to and being introduced to the water test device 110. In other examples, the mixing chamber 130 can include one reagent port 134 configured to receive regents that are mixed together elsewhere on the base plate 120 and provided to the reagent port 134 as a mixed sample. In other examples, the water test device 110 can be connected to more than three reagent sources. In that case, the mixing chamber 130 may include more than three reagent ports 134.

Figure 16:
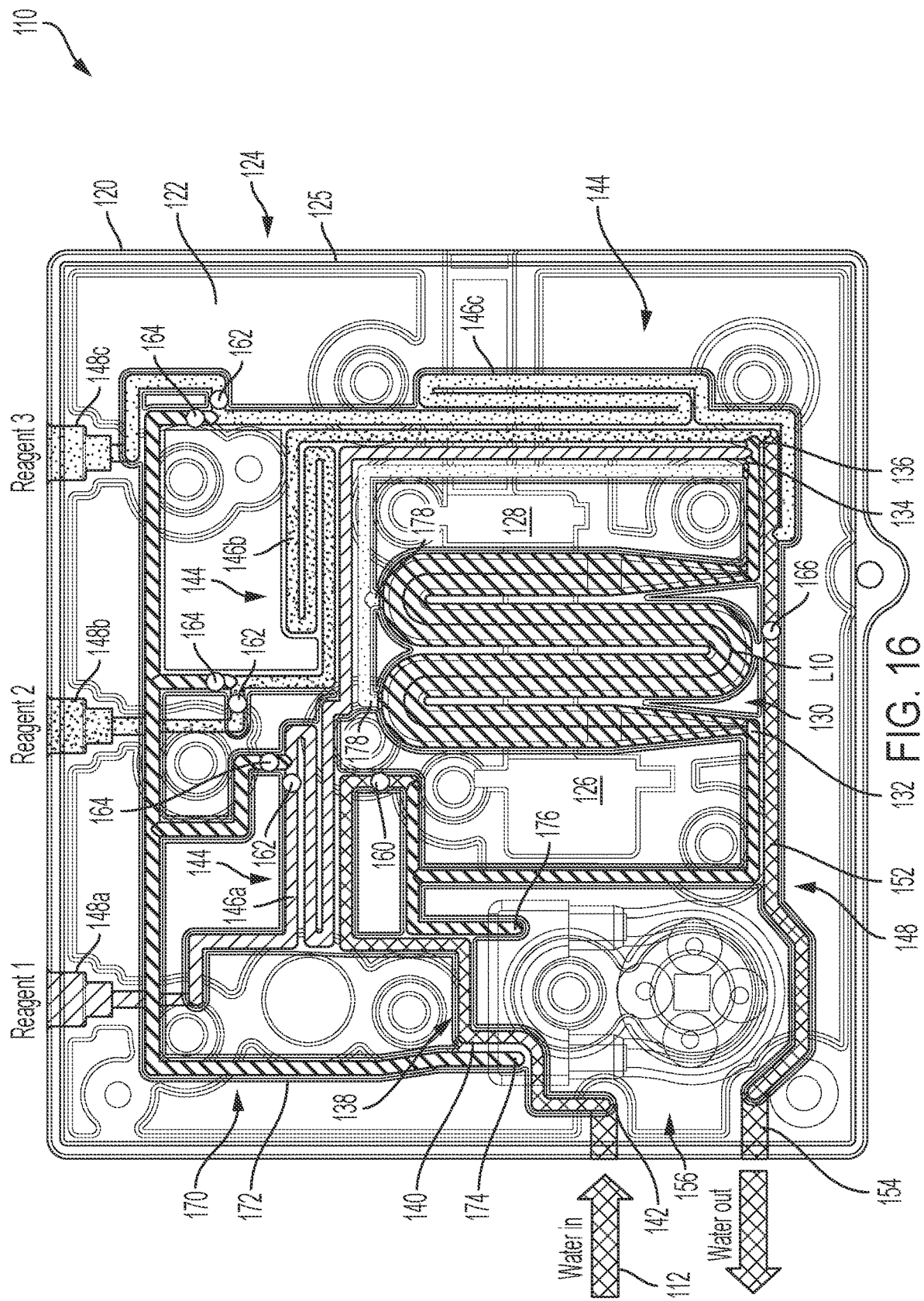
FIG. 16 is a top view of a test plate assembly of a water testing system, according to an example of the disclosure.

In some examples, the mixing chamber 130 is formed directly in the top surface 122 of the base plate 120 by, for example, machining or etching. The mixing chamber 130 can be any shape or configuration sized so that light from the light source 126 can be projected through the mixing chamber 130 and detected by the associated sensor 128. In some examples, as shown in FIG. 16, the mixing chamber 130 is a conduit arranged in a serpentine path on the top surface 122 of the base plate 120. For example, the mixing chamber 130 can be a serpentine conduit with four or more segments positioned so that light from the light source 126 passes through each segment of the serpentine conduit before contacting the sensor 128. It is believed that causing light to project through the multiple segments allows the sensor 128 to more accurately detect color and/or hue of the mixed water sampled in the mixing chamber 130 than if the mixing chamber 130 included only a single cavity or reservoir for receiving the mixed sample. A length (shown by path L10) and cross-sectional area of the serpentine conduit of the mixing chamber 130 are selected based on the volume of the water sample and reagent to be tested. In some examples, the volume of the mixing chamber 130 can be less than about 4.0 mL, from about 1.0 mL to about 3.0 mL, or preferably about 2.3 mL. For example, the mixing chamber 130 can be sized to contain a 2.0 mL water sample and 0.1 mL reagent doses for three different reagents (i.e., a total volume of 2.3 mL). In some examples, the length L10 of the serpentine conduit of the mixing chamber 30 is from about 75 mm to about 150 mm and the cross-sectional area of the serpentine conduit is about 10 mm$^2$ to about 25 mm$^2$. In some examples, a box bounding the serpentine mixing chamber 130 (shown in FIG. 16) can have the following dimensions: 32 mm×17 mm×4.65 mm. However, the dimensions of the mixing chamber 130 described herein are not intended to be limiting, and the mixing chamber 130 can be any shape or dimensions sufficient for containing the water sample and reagents. Specifically, as previously described, it is generally expected that the mixing chamber 130 should be sized to contain from about 1.0 mL to about 3.0 mL of liquid.

The water test device 110 also includes the light source 126 and the sensor 128 for detecting light from the light source 126 projected through and/or reflected from the mixed sample contained in the mixing chamber 130. Both the light source 126 and the sensor 128 can be mounted to the top surface 122 of the base plate 120 in proximity to the mixing chamber 130. In some examples, the light source 126 is a broad spectrum light-emitting light source, such as a broad spectrum light-emitting diode (LED). The sensor 128 can be a red-green-blue (RGB) light sensor configured to measure and/or characterize red, green, and blue components of lights projected through the water sample and onto a light-sensitive portion of the sensor 128. In some examples, the sensor 128 is a complementary metal-oxide-semiconductor (CMOS) sensor, as used in digital cameras and similar imaging devices.

The water test device 110 also includes a fluid circuit (shown generally by reference numbers 138, 144, and 150) on the base plate 120. The fluid circuit includes fluid connections and other fluidic components for one or more of: providing fresh water from the spa to the mixing chamber 130 through the water sample port 132, providing a dose of a reagent to the mixing chamber 130 through the reagent port 134, and for conducting a mixed sample from the mixing chamber through the drain port 136 after testing. In some examples, the fluid circuit includes an inflow portion 138 having at least one conduit 140 extending between a device inflow port 142 and the water sample port 132 of the mixing chamber 130; a reagent inflow portion 144 having conduits 146a, 146b, 146c extending from device reagent inflow ports 148a, 148b, 148c to the reagent ports 134 of the mixing chamber 130; and a drain outlet portion 150 comprising a conduit 152 extending from the drain port 136 of the mixing chamber 130 to a device drain port 154 connected to the discharge tube 27 shown in FIGS. 7 and 8. As previously discussed, water may flow from the water test device 110 to the drain 1014 and/or waste receptacle 118. The conduits 140, 146a-146c, 152 of the various portions 138, 144, 150 of the fluid circuit can include channels or grooves etched or machined into, for example, the top surface 122 of the base plate 120. Alternatively, in some examples, portions of the conduits 140, 146a-146c, 152 can be formed from tubing attached to and/or embedded in the base plate 120. For example, the tubing can be flexible plastic tubing used, for example, in medical peristaltic pumps, as are known in the art. The length and cross-sectional area of the conduits 140, 146a-146c, 152 can be selected based on the volume of water to be tested and/or on the fluid volume for each dose of reagent used for the water testing. For example, the conduits may have a cross-sectional area of less than about 1.5 mm$^2$.

The water test device 110 can also include a pump, such as a mixing pump 156, for moving the water sample, reagent, and/or mixed sample through the portions 138, 144, 150 of the fluid circuit. The pump 156 can be any micro-pump device, as is known in the art, including for example, peristaltic pumps, rotary pumps, impeller pumps, diaphragm pumps, and similar devices. In some examples, it is believed that the pump 156 should be a positive displacement pump, which is self-priming and able to pump air-bubbles through lines or conduits. For example, peristaltic pumps that can be used as mixing pumps 156 with the water test devices 110 of the present disclosure are manufactured by Takasago Fluidic Systems of Nagoya, Japan.

In one example, as shown in FIG. 16, the pump 156 is a peristaltic pump configured to contact a flexible portion of one of the conduits of the fluid circuit to move the water and/or the reagent through the conduits. As described in further detail hereinafter, in some examples, the pump can be a water inflow pump positioned near the device inflow port 142 for providing the water sample directly to the mixing chamber 130 and/or to other portions of the fluid circuit. The pump 156 can also be a mixing pump for mixing the water sample with doses of the reagents. In some examples, the water test device 110 can also include a reagent pump that draws the reagent from the reagent source to the reagent inflow portion 144 of the fluid circuit. In other examples, as described previously, reagents can be introduced from reagent sources to the water test device 110 by gravity or by another pump device external to the water test device 110.

The fluid circuit can further include valves for controlling fluid flow through the different portions 138, 144, 150 of the fluid circuit and, in particular, for controlling delivery of the water sample of the spa 1000 to the mixing chamber 130. The valves can be any device or mechanism for restricting, reducing, or preventing fluid flow through portions of the conduits of the fluid circuit. In some examples, the valves are pinch valves, as described in further detail hereinafter. Beneficially, pinch valves are believed to be simple to operate, especially for very small volumes. In other examples, some or all of the valves can be other types of micro-fluidic mechanisms, as are known in the art, including ball valves, diaphragms, balloons, and other structures capable of restricting or preventing fluid flow through portions of the conduits.

Generally, the valves are configured to move between an open position, where fluid flow through a conduit is permitted, and a closed position where fluid flow through the conduit is prevented. In some examples, the valves may also have a partially open position where a lower flow of fluid is permitted through the valve. As described in further detail hereinafter, in some examples, the valve(s) is/are formed from retractable members configured to extend into the conduits of the fluid circuit for blocking fluid flow through certain portions of the fluid circuit. In some examples, the water test device 110 can be mounted to an actuator device, such as an actuator plate 216 (shown in FIGS. 17A and 17B). The actuator plate 216 can be configured to move laterally, thereby engaging the retractable members to open and close the valves.

Types of valves that can be included in the water test device 110 include an inflow valve 160, reagent inflow valves 162 for restricting flow from each reagent source, mixing loop valves 164, and a drain valve 166 positioned between the drain port 136 of the mixing chamber and the device drain port 154.

The reagent inflow valve or valves 162 can be positioned on the reagent inflow portion 144 of the fluid circuit between the device reagent inflow port 142 and the reagent port 134 of the mixing chamber 130. As shown in FIGS. 16 and 18A-18D, the water test device 110 includes three reagent inflow valves 162, each of which is configured to control flow of a reagent (Reagent 1, Reagent 2, or Reagent 3) from a respective reagent source. The reagent inflow valve(s) 162 can have an open state in which reagent from the reagent source passes through the reagent inflow valve 162 toward the mixing chamber 130 and a closed state in which the reagent is prevented from passing through the reagent inflow valve 162. In some examples, a volume of the conduits 146, referred to as the reagent dose conduit 146a, 146b, 146c, between one of the reagent input valves 162 and the respective reagent port 134 of the mixing chamber 130 can correspond to a desired volume for the dose of reagent that will be introduced to the mixing chamber 130 and mixed with the water sample.

The reagent dose volume can be selected based on a volume of the mixing chamber 130 and the type of water test being performed. For example, the reagent dose volume can be from about 0.05 mL to about 1.0 mL. In some examples, the reagent dose conduits 146a-146c are arranged in a serpentine path to conserve space on the water test device 110. Also, the portion of the conduit 146a-146c forming the serpentine path may be substantially rigid and relatively narrow having a cross-sectional area of, for example, less than about 1.5 mm². It is believed that fluid is unlikely to flow backward through a narrow rigid tube or conduit in the same manner as may occur with larger, wider, and/or more flexible tubes. Accordingly, when the reagent dose conduit is rigid and narrow, it is believed that an inflow or check valve may not be needed to prevent reagent backflow through the fluid circuit, since the shape of the tube or conduit reduces and/or will not accept backflow.

As shown in FIGS. 18A-18D, the drain valve 166 is positioned on the water test device 110 between the drain port 136 of the mixing chamber 130 and device drain port 154. As described herein, the device drain port 154 can be connected to a drain outlet line for directing the mixed fluid sample from the water test assembly 12 to, for example, the drain 1014. The drain outlet line may also be connected to the waste receptacle 118 in the spa.

The fluid circuit may also include check valves 168 for preventing fluid backflow through portions of the fluid circuit. As used herein, a "check valve" refers to a mechanical structure that permits fluid flow through a conduit in one direction and prevents or restricts fluid flow through the conduit in an opposite direction. For example, the reagent inflow portion 144 may include check valves 168 to prevent reagent from flowing back toward the reagent sources. The reagent portion may also include check valves 168 positioned near to the reagent port(s) 134 of the mixing chamber 130 to prevent the water sample and/or reagent from flowing out of the mixing chamber 130 toward the reagent portion 144 of the fluid circuit. In some examples, the water inflow portion 138 may include check valves 168 to prevent water from flowing through the device inflow port 142 back toward the main pump 13 or other components of the circulation system of the spa 1000.

With continued reference to FIGS. 16 and 18A-18D, in some examples, the fluid circuit also includes a mixing loop portion 170 including a conduit 172 extending between the water sample inflow portion 138 and branches of the reagent portion 144 for mixing the water sample and the dose of the reagent. For example, the mixing loop portion 170 of the fluid circuit can include portions or branches connected to reagent dose conduits 146a-146c for three different reagents. As previously discussed, however, the number of reagents connected to the water test device 110 is not intended to limit the scope of the present disclosure. The mixing loop portion includes mixing loop valves 164 connected, for example, between the mixing loop portion 170 and the reagent portion 144 of the fluid circuit. When the mixing loop valves 164 are open, water can pass from the mixing loop portion 170 to the reagent portion 144. The water passing through the mixing loop valves 164 can move the dose of the reagent contained within the reagent dose conduit 146a-146c to the mixing chamber 130. When the mixing loop valve(s) 164 are closed, reagent from the reagent source or sources is prevented from moving into the reagent portion 144 of the fluid circuit.

In some examples, the pump of the test device is a mixing pump 156 positioned in the mixing loop portion 170 of the fluid circuit upstream from the mixing loop inflow valves 164. The mixing pump 156 can be configured to move the water sample from the mixing chamber 130 through the mixing loop portion 170 and reagent portion 144 back to the mixing chamber 130 when the mixing loop valves 164 are open. Moving the water sample in this way allows the water sample to mix with the dose(s) of reagent to provide a mixed sample that can be used for testing. The mixing pump 156 can be a peristaltic pump, as shown in FIG. 16, having an inlet 174 configured to receive a water sample from the mixing chamber 130 and an outlet 176 for expelling the water through the mixing loop portion 170 and reagent portion 144 of the fluid circuit. The pump 156 can be a single-speed pump configured, for example, to operate at 160 rpm with a flow rate of, for example, from about 100 mL/minute to about 200 mL/minute. In other examples, the mixing pump 156 can be a variable speed pump configured to operate at different speeds (e.g., high speed and low speed). For example, the pump 156 may operate at 150 rpm during some portions of a water test protocol and at a higher speed, such as 250 rpm, during other portions of the protocol.

Water Testing and Data Collection Systems

As previously described, the water test assembly 12 can include one or multiple water test devices 110 along with electro-mechanical actuating devices and electronic control circuitry for operating and collecting data from the water test device(s) 110. The water test device(s) 110, actuating devices, and control circuitry can be integrated and/or operably connected together forming the water testing system 10.

In some examples, the water testing system 10 includes the one or more test devices 110. As shown in FIGS. 7 and 8 and as previously described, the multiple water test devices 110 can be aligned in series in the reusable unit or portion of the water test assembly 12. The water test devices 110 can include features of any of the previously described exemplary water test devices 110 described herein, which generally include the base plate 120, mixing chamber 130, light source 126, sensor 128, and fluid circuit including portions 138, 144, 150. The water test devices 110 can also include any of the previously described valves 160, 162, 164, 166, 168 for controlling introduction of the water sample and dose of the reagent to the mixing chamber 130 and for draining the mixed sample from the water test device 110 after the test is completed. The water test devices 110 can also include one or more pumps, such as mixing pump 156, for moving the water sample and reagents through the fluid circuits of the water test devices 110.

In some examples, the multiple water test devices 110 can be operably connected in series to a single actuating device, such as the motors 23, 24. For example, the actuating device can be a single motor configured to actuate a spindle configured to operate pumps 156 of each water test device 110. As previously discussed, the system 110 may also include the valve actuator plates 216 associated with each of the water test devices 110. The valve actuator plates 216 can be moved laterally between different positions to open and close different valves of the fluid circuit. In some examples, the valve actuator plates 216 are operably connected to the valve actuating plate motor 23 or to another driving device by a cam assembly (shown generally by reference number 28) to move the valve actuator plates 216 between the different positions.

Figure 17A:
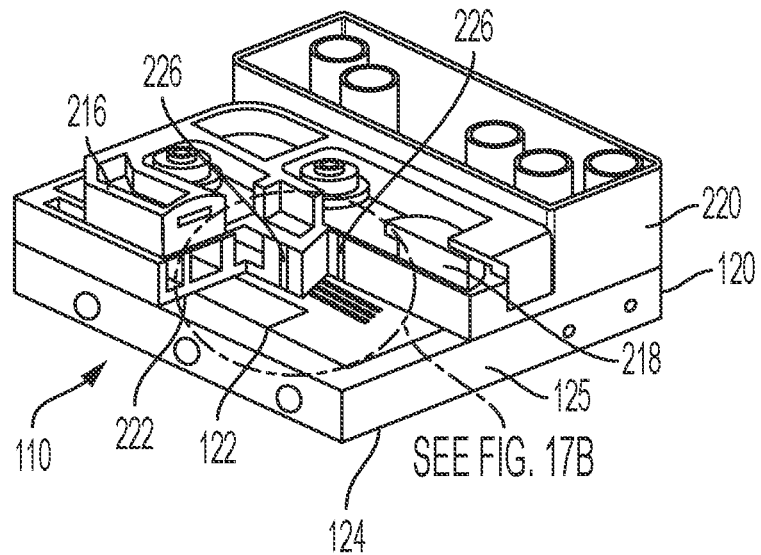
FIG. 17A is a perspective view of a test plate assembly and valve actuator plate of the water testing system.
Figure 17B:
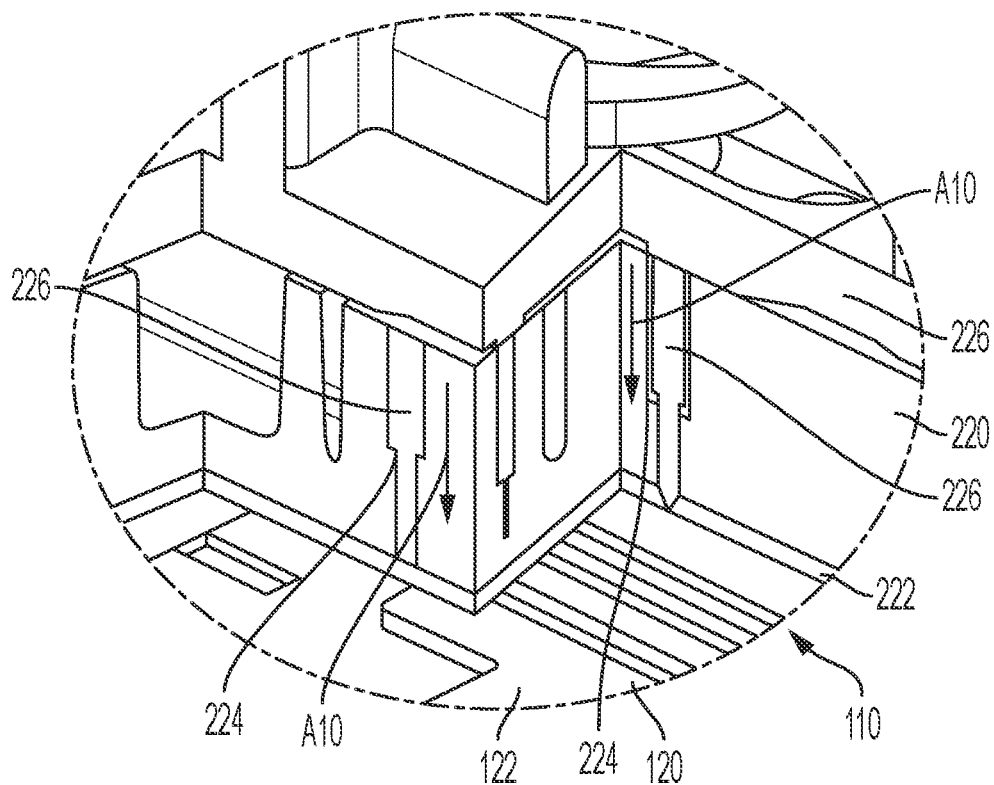
FIG. 17B is an enlarged perspective view of a portion of the test plate assembly of FIG. 17A showing valves of the test plate assembly.

Operation of an exemplary valve actuator plate 216 that can be used with the water test devices 110 described herein is shown in FIGS. 17A and 17B. While only two valves are shown in FIGS. 17A and 17B, it is understood that any or all of the valves of the water test device 110 can function as described herein and as shown in FIGS. 17A and 17B. In other examples, some or all of the valves of the water test assembly 110 may include other micro-fluidic valve structures or devices, such as solenoid valves, ball valves, diaphragms, or balloons, as are known in the art.

As shown in FIGS. 17A and 17B, the valve actuator plate 216 for each water test device 110 is mounted to a cover 220. The cover 220 can be an acrylic plate similar in size and orientation to the base plate 120 of the water test device 110. A resilient flat gasket 222 is positioned between the cover 220 and the base plate 120. The cover 220 includes valve guide holes 224 sized to receive retractable valve members, referred to herein as valve pins 226. Each valve pin 226 cooperates with the flat gasket 222 to operate as a valve for restricting fluid flow through one of the conduits 140, 146a-146c, 152 of the fluid circuit. The valve actuator plate 216 moves with respect to the cover 220 and the base plate 120. Upon movement of the plate 216, the plate 216 contacts a portion of some or all of the valve pins 226, causing the contact pin or pins 226 to move in a downward direction, shown by arrow A10. The valve pin 226 contacts and presses against the flat gasket 222, causing the gasket 222 to press into one of the conduits on the base plate 120, which restricts fluid flow through the conduit. Upon continued movement of the actuator plate 216, the pressure against the portion of the valve pin 226 can be removed. Once the pressure is removed, the resilient gasket 222 exerts a biasing force against the pin 226, causing the pin 226 to move away from the conduit in the base plate 120, meaning that the valve moves to an open position.

As discussed herein, the valve actuator plate 216 can be configured and/or shaped to move between two or more positions, which correspond with different operating states of the water test device 110. For example, when the valve actuator plate 216 is in a first position, the plate 216 can be shaped so that some of the valves are open, which can allow for spa water to be introduced to the water test device 110, to clean or purge portions of the water test device 110. When the valve actuator plate 216 moves to a second position, the plate 216 may be shaped to cause some of the valves to move between open and closed positions. In this second state or position, for example, reagent from reagent sources may be permitted to flow to the water test device 110. The valve actuator plate 216 may have two, three, four, or more positions corresponding to distinct permutations of the individual valves.

In addition to the pumps 156 and valves 160, 162, 164, 166, 168 on the water sensing device(s) 110 themselves, the system 210 can include pumps external to the water test device. For example, the water testing system 10 can include the circulation pump 14 spaced apart from the water test device(s) 110 that draws water from the spa into the water test assembly 12 and distributes the received spa water to the different water test devices 110. In some examples, the circulation pump 14 is also configured to drain the mixing chamber 130 after testing is completed. In other examples, the circulation pump 14 or another pump located in the water test assembly and/or testing system can be configured to draw mixed water samples from the water test device 110 after testing is completed.

The water testing system 10 also includes electronic circuitry for controlling the motors 212, pumps 156, 228, and valve actuator plates 216 of the system 210. The circuitry can include, for example, a controller 232 (shown in FIG. 21), such as a microprocessor and/or computer device, in electronic communication with the pumps 14, 156, motors 23, 24, and with the sensor 128 of the water test device(s) 110. The controller 232 is configured to perform tasks necessary for water testing including, for example, activating the motors 23, 24 and/or causing certain valves to open and close according to a predetermined water test protocol. For example, the water test protocol can include performance of one or more of the following actions: purging or flushing the fluid circuit and mixing chamber 130 of the water test device(s) 110 prior to water testing; introducing a water sample to be tested to the mixing chamber 130; preparing the dose of the reagent; mixing the reagent and the water sample, thereby providing a mixed sample in the mixing chamber 130; collecting measurement data, such as color and/or light intensity measurements, for the mixed water sample in the mixing chamber 130; and draining the mixed sample from the mixing chamber 130 after testing. The water test protocol implemented by the controller 232 can be a short-duration test lasting, for example, less than about 10 minutes, or preferably from about 3 minutes to about 5 minutes. The system 10 can be programmed to perform the water test protocol several times (e.g., two or three times) each day. In other examples, the system 10 can be configured to execute the water test protocol when an instruction (e.g., an instruction from a remote control device or system) is received requesting that a water quality test be performed.

After the measurement data is collected, the controller 132 can also be configured to process or analyze the measurement data to determine water quality parameters for the water sample. The calculated water parameters are based, for example, on received color and/or light intensity values. In some examples, determining at least one water parameter can include calculating a Hue, Saturation, and Value (HSV) for the water sample based on information detected by the sensor 128 and determining the water parameters based on the calculated HSV. For example, the controller 232 can be configured to perform a transfer function on RGB values (e.g., color information) generated by the sensor to convert the RGB values to the HSV (Hue, Saturation, and Value). In some examples, only certain values, e.g., R, G, B, H, S, V, provided directly from the sensor 128 or calculated by the transfer function are used to determine a particular water parameter. For example, the calculated HSV may be the only value used to determine pH and total alkalinity. Other parameters may be calculated based on intensity values for multiple wavelengths of light.

In some examples, carrying out the water test protocol, as implemented by the controller 232, can include moving the water test device 110 between different operating states, such as operating states for preparing the test device 110 to receive the water sample, mixing the water sample with the reagent dose, and flushing the mixed sample from the water test device after testing. Specifically, the water test device 110 transitions between the different operating states by opening and closing valves 160, 162, 164, 166, and by operating the pump 156, optionally at different operating speeds, to control movement of water and reagent through the water test device 110. The different operating states are shown in FIGS. 18A-18D. FIG. 19 shows a flow chart for the water test protocol or process that can be implemented by the controller 232 for water testing using the water test devices 110 and water testing system 10 disclosed herein.

The water test protocol or process includes a step 310 of purging or flushing the fluid circuit and mixing chamber prior to water testing. The purge state is shown schematically in FIG. 18A. In the purge state, the inflow valve 160 and the mixing loop valve 164 are open, allowing fresh water from the spa 1000 to flow through the device inflow port 142 and through the inflow portion 138 and reagent portion 144 of the fluid circuit to the mixing chamber 130. The drain port 136 and/or drain valve 166 are also open so that the water passes through the mixing chamber 130 and the drain outlet portion 150 of the water test device 110 to the drain 1014 of the spa 1000 and/or to the waste container 118.

During the purge state, the circulation pump 14, which can be external to the water test device 110, is actuated or turned on to pump water to the water test device 110. The water passes through the inflow valve 160 to the mixing chamber 130 through the water sample port 132 of the mixing chamber 130 as shown by arrow A12. Also, some water branches off from the inflow portion 138 into the mixing loop portion 170 of the fluid circuit as shown by arrow A14. In the purge state, the mixing pump 156 can be on and, in some cases, can be operated at a high speed of, for example, 250 rpm. The mixing pump 156 moves the water through the mixing loop portion 170 and mixing loop valve 164 to the reagent portion 144 of the fluid circuit, as shown by arrows A16a, A16b, and A16c. In the purge state, the reagent input valves 162 are closed and the reagent pump, if present, is off so that reagent from the reagent sources does not pass to the water test device 110 and so that the water does not flow into the reagent source. The purge state can last for any selected duration sufficient for flushing the mixing chamber 130 and fluid circuit to a sufficient degree to avoid contaminating the water sample and/or to avoid negatively affecting water test results. For example, the purge state can be about 120 seconds in duration.

At step 312 of the water test protocol, a dose of reagent is prepared by introducing a volume of the reagent to the water test device 110 from the reagent source. As shown in FIGS. 16 and 18A-18D, and as previously described, the water test device 110 is connected to three different reagent sources. For some water tests, several different types of reagents can be introduced to the mixing chamber 130 at the same time for testing different water parameters simultaneously. In that case, the reagent dose preparation process may be used to prepare reagent doses for two or more reagents simultaneously. When testing other water parameters (such as pH and total alkalinity), only one reagent is used at a time. In that case, the reagent dose preparation step may be performed for only one reagent.

Figure 18A:
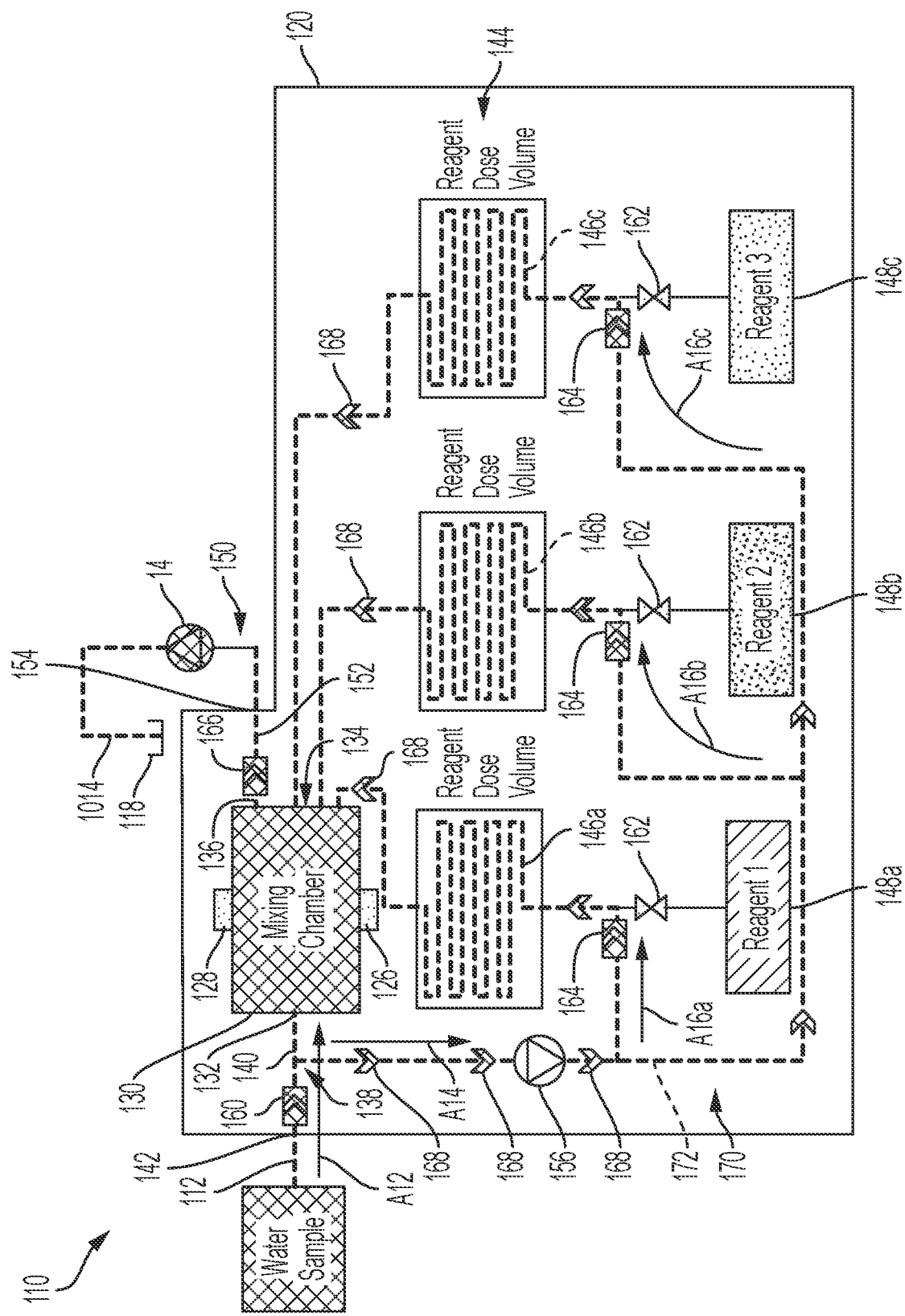
FIGS. 18A-18E are schematic drawings of test plate assemblies in different operating states of a water test protocol, according to an example of the disclosure.
Figure 18B:
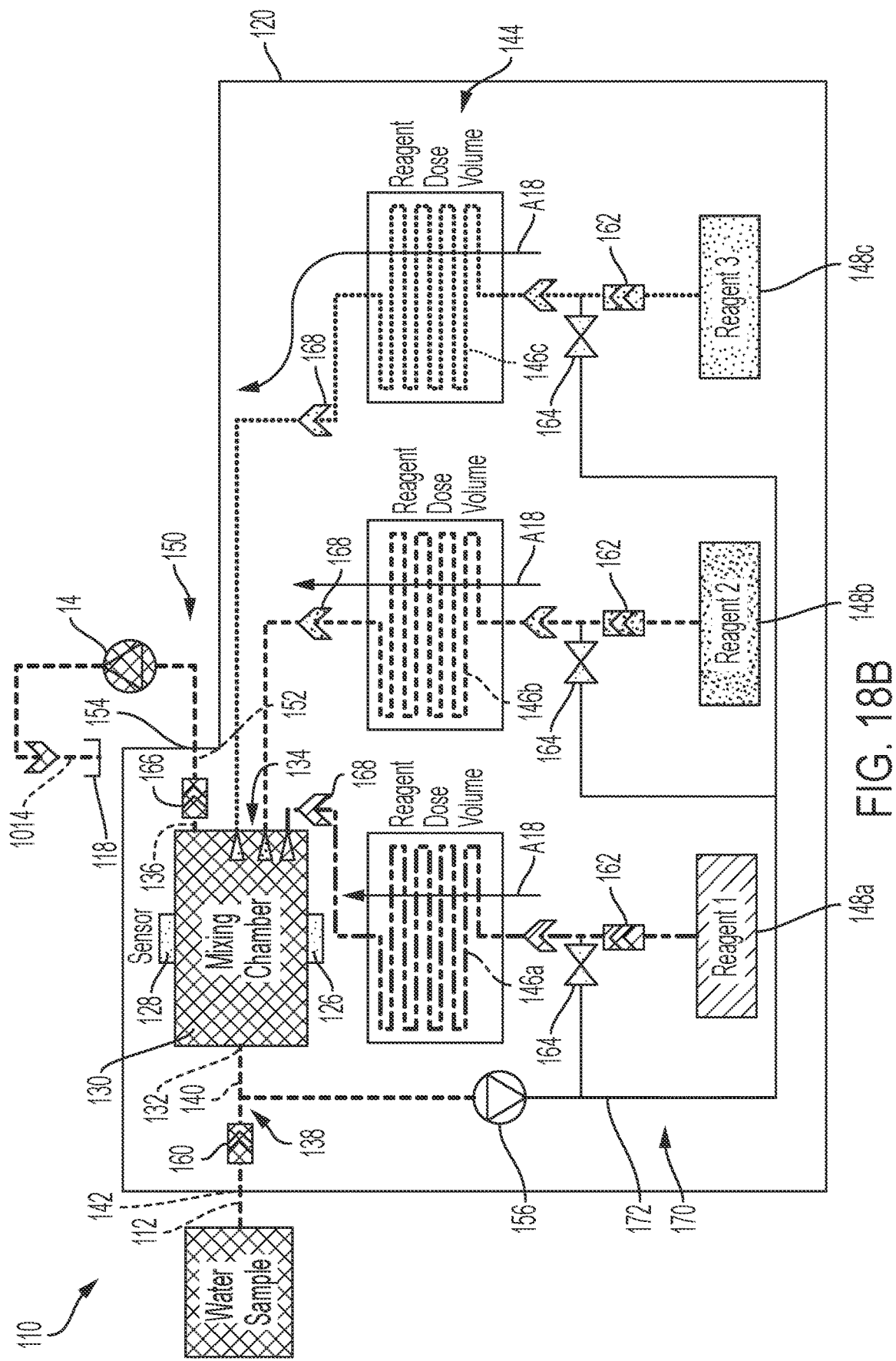
Figure 19:
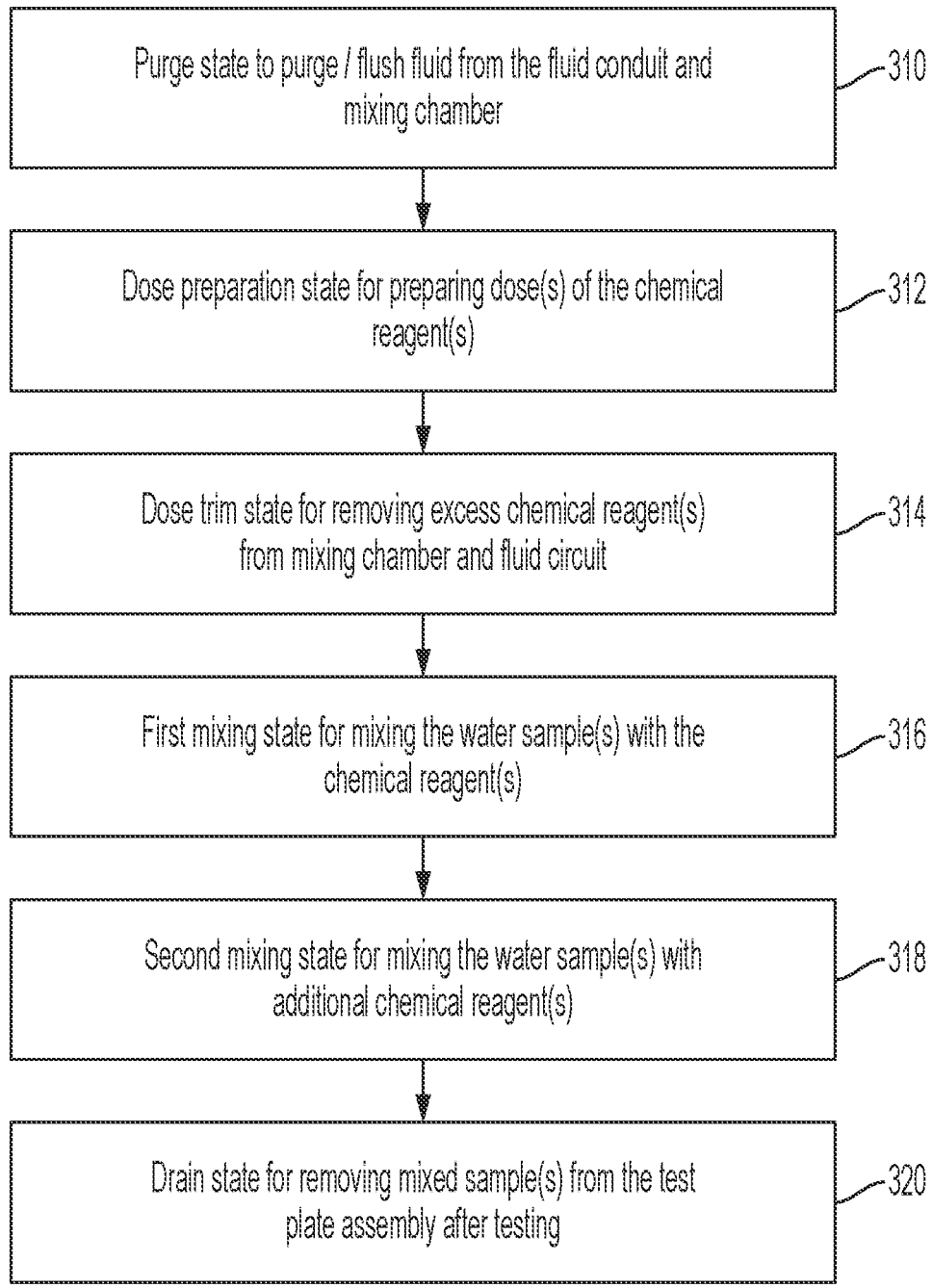
FIG. 19 is a flow chart of a water test protocol for a test plate assembly.

FIG. 18B depicts the water test device 110 in a reagent dose preparation state. In the reagent dose preparation state, the reagent inflow valve or valves 162 for the reagent dose being prepared are open. Reagent valves 162 for any other reagents are closed. The mixing loop valves 164 are closed to prevent reagent from flowing into the mixing loop portion 170 of the fluid circuit and, in particular, to prevent the reagent from flowing to the mixing pump 156. The mixing pump 156 can be off.

During the reagent dose preparation step, the reagent or reagents pass from the reagent sources to the device reagent port or ports 148. In some examples, the reagents are introduced to the water test device 110 under power provided by one or more reagent pumps. In other examples, the reagents may flow from the reagent sources to the water test device 110 by gravity. Once the reagent is introduced to the water test device 110, the reagent passes through the open reagent inflow valve 162 and flows through the reagent dose conduits 146a-146c toward the reagent ports 134 of the mixing chamber 130, as shown by arrow A18. As the reagent advances through the reagent portion 144, any water remaining in the reagent portion 144 from the previously described purge state is displaced and flows toward the mixing chamber 130. As previously discussed, the reagent dose conduits 146a-146c form a serpentine path having a total volume corresponding to a volume for the dose of reagent needed for the water test being performed. Also, it is believed that the serpentine path in combination with the narrow cross-sectional area of the conduit allows the advancing reagent to displace any water in the conduit with only limited mixing during the dose preparation stage.

Figure 18C:
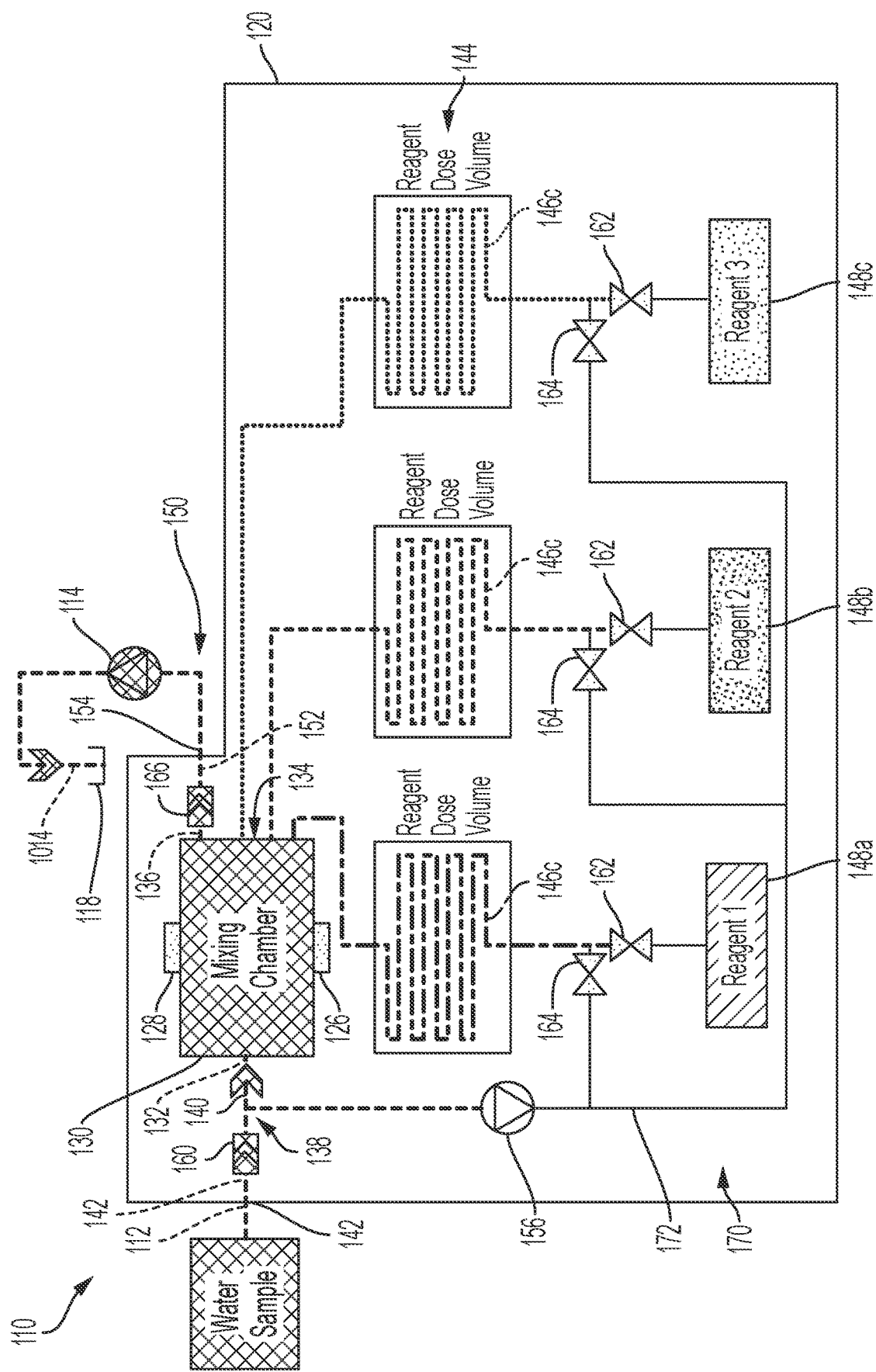

At step 314, a dose trim state is performed to flush any excess reagents from the fluid circuit that may have passed into the mixing chamber 130 and/or portions 138, 144, 150 of the fluid circuit. During the dose trim state, the reagent inflow valves 162 can be closed to prevent reagent from flowing back toward the reagent source, as shown in FIG. 18C. The mixing loop valves 164 are closed to prevent reagent from passing to the mixing loop portion 170. The water inflow valve 160 is open. Water passes through the inflow portion 138 of the fluid circuit into the mixing chamber 130, which flushes the mixing chamber 130 to remove any reagent that has passed into the mixing chamber 130 during the dose preparation state. This trimming operation skims off the reagent such that the reagent dose volume in the reagent dose conduit 146a-146c between the reagent input valves 162 and the reagent ports 134 of the mixing chamber 130 are the correct reagent dose. Following the dose trim step, an amount of fresh water remaining in the mixing chamber 130 is a sufficient amount for the water test to be performed. The remaining water becomes the water sample, which is mixed with the reagent in the following steps of the water test protocol.

In this reagent dose preparation state, the external circulation pump 14 is on, but may be operating in a low operating state (e.g., a lower volumetric flow rate and/or pressure than when in the purge state). During the dose trim stage, the external circulation pump 14 is turned on and may be operated at a higher pressure and/or volumetric flow rate than the low state at which the pump 14 is operating during the dose preparation stage. Accordingly, water from the spa 1000 is pumped through the device inflow port 142 and inflow portion 138 of the fluid circuit. The water then passes through the water sample port 132 into the mixing chamber 130. The water passes through mixing chamber 130 and drain port 136 to carry off excess reagent that is pumped into the mixing chamber 130. During the dose trim state, the mixing pump 156 is turned off and the mixing loop valves 164 are closed so that the spa water does not pass through the mixing loop portion 170 or reagent portion 144 of the fluid circuit.

In order to avoid affecting the reagent dose volume, water in the mixing chamber 130 should not backflow through the reagent port(s) 134 of the mixing chamber 130 to the reagent portion 144 of the fluid circuit. In some examples, the structure of the serpentine fluid line itself, which can be formed from rigid materials, inhibits backflow of water pumped through the mixing chamber 130 from flowing through the reagent port(s) 134 so that any remaining reagent in the mixing chamber 130 instead flows toward the drain port 136 and into the drain portion 150 of the fluid circuit. Alternatively or in addition, a one-way check valve 168 can be positioned upstream from the reagent ports 134, which also inhibits backflow of water into the reagent dose conduits 146a-146c from the mixing chamber 130 when the circulation pump 14 is activated. Beneficially, this dose trim method allows for imprecise pumping of the reagent, since any extra reagent is purged or trimmed from the water test device 110 before mixing the reagent with the water sample. Beneficially, this arrangement allows for a less expensive and/or a somewhat imprecise pump, since the pump is not used to determine the exact fluid volume for the reagent dose.

At step 316, once the reagent dose is prepared and other reagent purged from the water test device 110, the water test device 110 is moved to a mixing state for combining the prepared reagent dose(s) with the water sample. In some examples, multiple reagent doses are combined together simultaneously. In other examples, only a reagent dose for one type of reagent is mixed with the water sample. Also, in some examples, the water test protocol can include multiple mixing steps where a first reagent or group of reagents is added to the water sample during a first mixing step, and a second reagent or group of reagents is added to the water sample during a second mixing step. A water test protocol including multiple mixing steps is shown schematically in FIGS. 18D and 18E.

Figure 18D:
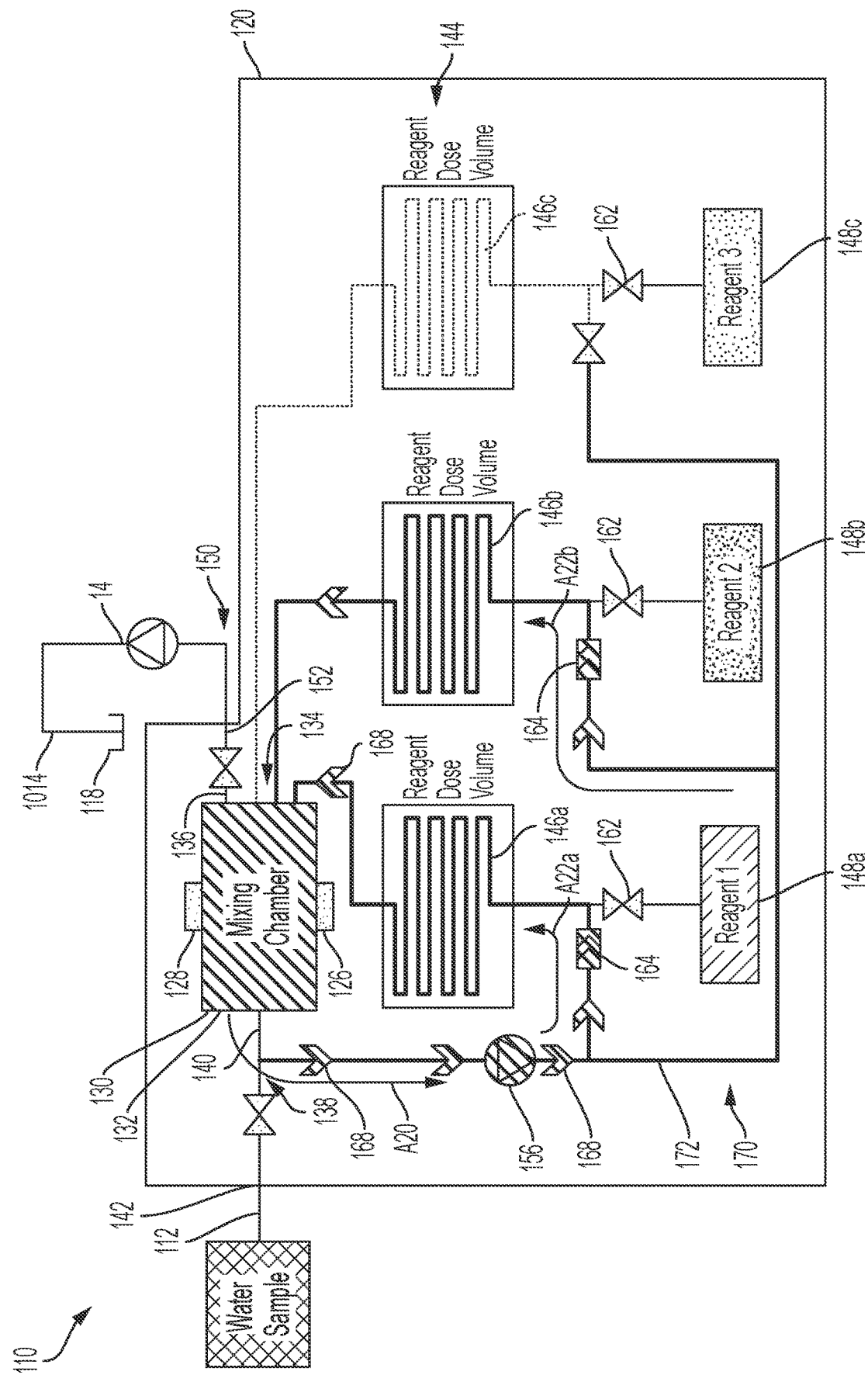
Figure 18E:
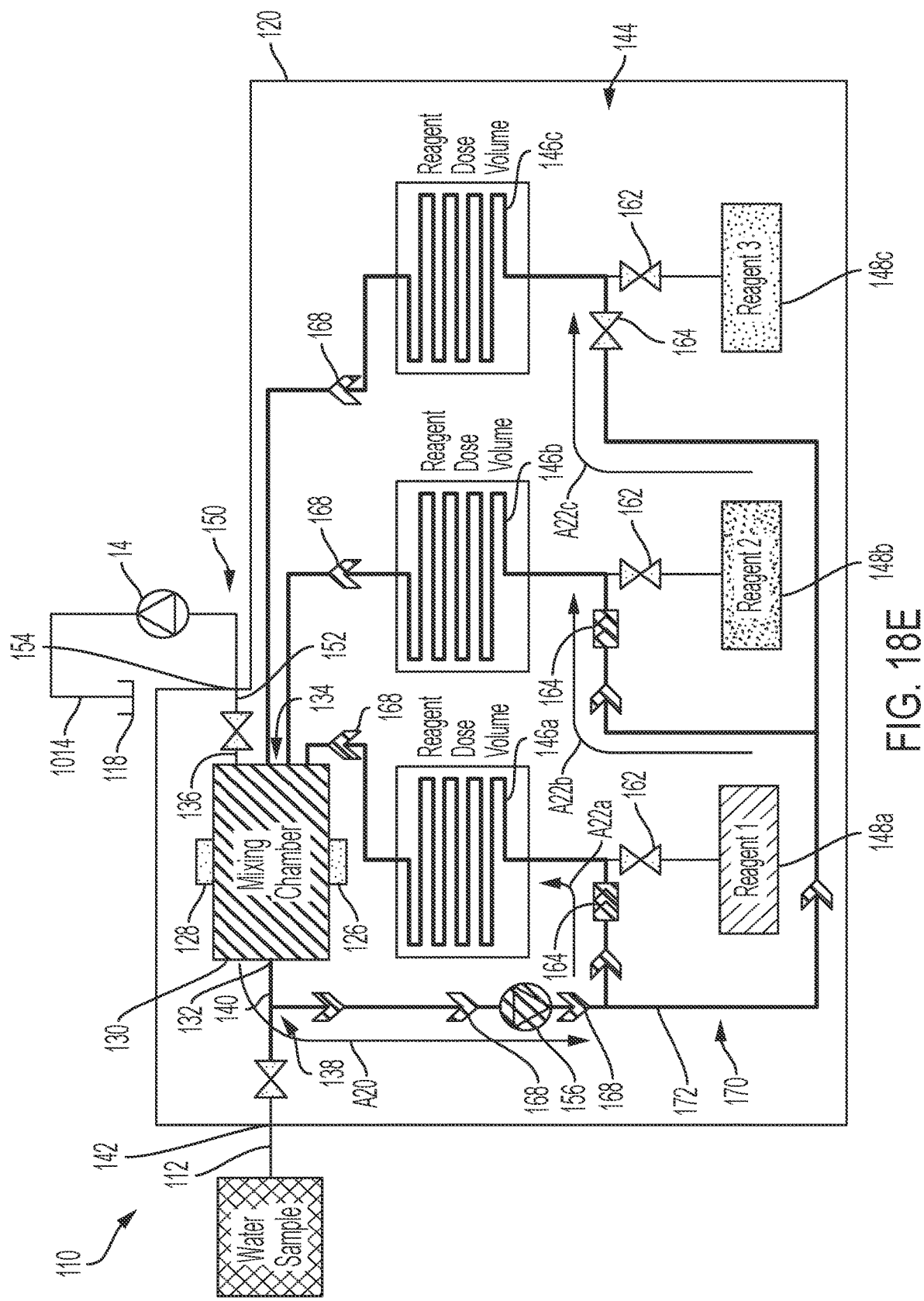

As shown in FIG. 18D, in the first mixing state, two reagents are mixed together with the water sample to provide the mixed sample. For this first mixing step, the circulation pump 14 is off and the water inflow valve 160 is closed. The mixing pump 156 is on and the mixing loop valves 164 for Reagent 1 and Reagent 2 are open. The mixing loop valve 164 for Reagent 3 remains closed. In the mixing state, the reagent input valves 162 are closed to prevent additional reagent from being introduced to the water test device 110. The drain valve 166 is also closed to prevent the mixed sample from draining from the mixing chamber 130.

In this first mixing state, the water sample (e.g., water remaining in the mixing chamber 130 after the dose trim step) in the mixing chamber 130 flows through the water sample port 132 toward the mixing pump 156, as shown by arrow A20. The water passes through the mixing pump 156 and toward mixing loop valves 164 associated with the reagents to be used (e.g. Reagent 1 and Reagent 2). As shown in FIG. 18D, the mixing loop valves 164 for Reagent 1 and Reagent 2 are open, which allows the water to pass through the open valves and to the reagent dose conduits 146a, 146b for Reagent 1 and Reagent 2, as shown by arrows A22a and A22b. The mixing loop valve 164 for Reagent 3 is closed, which prevents the circulating water from being diverted to the reagent dose conduit 146c for Reagent 3 and from contacting any reagent in the reagent dose conduit 146c. The water passing through the reagent dose conduit 146a, 146b for Reagent 1 and Reagent 2 mixes with and/or pushes the dose of reagent through the reagent port 134 and back into the mixing chamber 130, where it forms a mixed sample along with the water sample. The mixed sample can continue to circulate through the mixing loop portion 170 and reagent portions 144 of the fluid circuit as shown by arrows A20, A22a, and A22b for as long as the mixing pump 156 is turned on or activated. The mixing pump 156 can be turned on or activated for a predetermined amount of time to provide for adequate mixing of the reagent and the water sample. For example, the mixing pump 156 can be turned on to a speed of 250 rpm for about 120 seconds.

After the water sample and reagents are sufficiently mixed, the light source 126 is turned on to project light through the mixing chamber 130. Projected light that is transmitted through or reflected from the mixed sample in the mixing chamber 130 is detected by the sensor 128. Measurements by the sensor 128 are provided to the controller 232, which can process received data to determine water quality parameters for the water sample being tested.

At step 318, after testing of the mixed sample produced by the first mixing process is completed, a second mixing step can also be performed. During the second mixing step, the chemical reagent dose for Reagent 3 is introduced to the mixed sample. In order to perform the second mixing step, the mixing loop valve 164 associated with Reagent 3 is opened. The mixing loop valves 164 associated with Reagent 1 and Reagent 2 can also remain in the open position. Mixing is performed again by activating the mixing pump 156 to draw the mixed sample from the mixing chamber 130. As in the previous mixing step, the sample moves through the inflow portion 138 and mixing loop portion 170 of the fluid circuit, as shown by arrow A20. The sample then branches off, passing through the open mixing loop valves 164 associated with each of the three reagents, as shown by arrows A22a, A22b, and A22c, and then through the reagent dose conduits 146a-146c for each reagent. Water passing through the reagent dose conduit 146c for Reagent 3 contacts the third reagent dose, causing the third reagent dose to pass through the reagent port 134 and into the mixing chamber 130. Portions of the mixed sample passing through the reagent dose conduits 146a, 146b for Reagent 1 and Reagent 2 also pass through reagent port 134 and into the mixing chamber 130. As for the previous mixing step, water can continue to flow from the mixing chamber 130 and through the mixing loop portion 170 and reagent portions 144 of the fluid circuit (shown by arrows A20, A22a, A22b, and A22c) for a predetermined duration, such as about 120 seconds, selected to allow the three reagents and water sample to mix completely. Once the water sample and reagents are sufficiently mixed, light transmittance and/or reflectance measurements can be obtained by the sensor 128, as previously discussed. The measurements detected by the sensor 128 can be provided to the controller 232, which can process received data to determine water quality parameters for the water sample being tested.

At step 320, after testing for the mixed sample or mixed samples is completed, a drain step can be performed to drain the mixed sample from the mixing chamber 130. In order to drain the mixed samples from the mixing chamber 130, the drain valve 166 can be opened and the circulation pump or a separate circulation pump, which can be external to the water test device 10, is activated. The activated circulation pump draws the mixed water sample from the mixing chamber 130, through the drain portion 150 of the fluid circuit, and to the drain 1014 and/or to the waste receptacle 118.

Remote Spa Control Systems

The water testing assemblies and systems disclosed herein can be integrated and/or used with remote spa control systems, such as the spa control system described in the '325 publication. As described in further detail herein, remote spa systems can comprise computer devices, servers, databases, and other electronic components remote from the spa. The remote computer devices and other systems can be configured to receive information from one or more spas, provide the information to users, spa owners, manufacturers, dealers, and other third parties, and, in some cases, provide instructions to the spa for controlling operation of the spa 1000.

Figure 21:
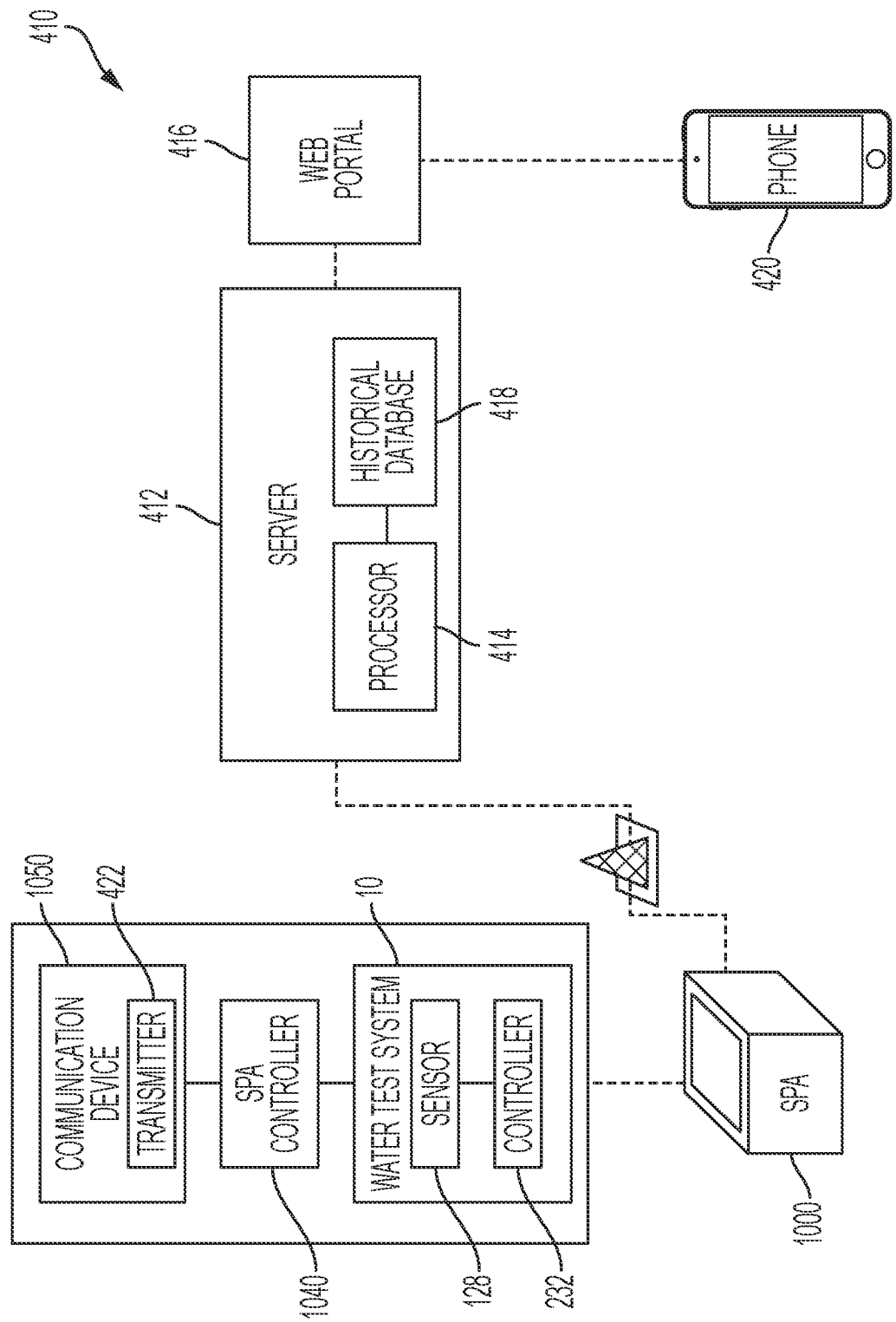
FIG. 21 is a schematic drawing of a remote control system for a spa, according to an example of the disclosure.

For example and with reference to FIG. 21, the water testing assemblies 12 and systems 10 disclosed herein can be used with a system 410 for remote monitoring and control of one or more spas 1000 using a computer or portable electronic device 420 (e.g., smartphone) with Internet connectivity. The system 410 can be configured to permit remote monitoring and control of one or more spas 1000 utilizing a website, web-based portal 416, or App accessible by a spa owner, spa dealer, or another authorized party over, for example, computer server and web portal. The website, portal 416, or App provides a user interface (shown by user interface screens 610a, 610b, 610c in FIGS. 22A-22C), which allows a user to: control different components and devices on the spa 1000; schedule spa operations remotely; and review real-time or previously collected data (e.g., diagnostic information, pump/heater data, water parameters, fault logs, etc.) uploaded from the spa 1000 to the website or App. The user interface may also provide notifications about faults or errors identified by the spa controller 1040 and scheduled maintenance activities.

As shown in FIG. 21, the remote spa control system 410 includes the spa 1000 including any or all of the previously described components, devices, assemblies, and systems. For example, the spa can include a water circulation system including the circulation pump 14 and the testing system 10, as previously described. The testing system 10 includes the controller 232 for determining water quality parameters based on information from the sensor 128 on each test plate assembly or water test device 110. The spa 1000 also includes the spa controller 1040 electronically connected to devices of the water circulation system and the testing system 10. For example, the spa controller 1040 can be electronically connected and configured to control the pumps, heaters, filtration devices, chlorinators, and any other devices on the spa 1000. The spa 1000 also includes the communication system or devices 1050, which can include, for example, a wired or wireless transmitter 422 in electronic communication with the spa controller 1040. The wired or wireless transmitter 422 can be configured to transmit and/or receive electronic signals from remote computer devices, systems, computer servers 412, and networks (e.g., the Internet). A wired transmitter can be configured to be connected to a computer network via, for example, coaxial, fiber optic, or Ethernet cables. A wireless transmitter, if present, can be configured to transmit electronic signals by any known short-range or long-range wireless transmission system including, for example, WiFi, cellular, or Bluetooth®. Additional details of wired and wireless communications systems that can be used with a spa 1000 are described in the '325 publication, which is incorporated by reference herein.

As in previous examples, the spa testing system 10 includes the water testing assembly 12 which includes the one or more water test devices 110 or test plate assemblies fluidly connected to the spa 1000 by the water circulation system (e.g., the circulation pump 14) to receive water and/or water samples from the spa 1000. The water test device 110 or test plate assemblies can include components of any of the previously described water test devices 110 or test plate assemblies. For example, the water test device 110 or test plate assembly can include the mixing chamber 130 and the sensor 128 electrically connected to the controller 232 of the test assembly configured to detect color and/or light intensity information for light transmitting through or reflecting from the mixing chamber 130. The water test device 110 or test plate assembly also includes the fluid circuit 138, 144, 150 for providing water or water samples from the spa 1000 to the mixing chamber 130 using, for example, the circulation pump 14 of the spa circulation system. The fluid circuit 138, 144, 150 also provides a dose of the chemical reagent to the mixing chamber 130 and, following testing, moves the mixed sample from the mixing chamber 130 through the drain port 136 of the mixing chamber 130.

The remote control system 410 also comprises the remote computing device and/or computer server 412 comprising a processor 414 for receiving and processing information from the spa 1000. The system 410 can also include a web portal 416 for providing water quality information to the user and for receiving commands and instructions from the user over a website or App. The processor 414 can be a general purpose or specialized computer microprocessor, as are known in the art. The processor 414 can be contained within a general purpose computer controlled by a spa owner or another party. In other examples, the remote processor 414 can be a processor of a remote computer server 412 controlled by, for example, a spa manufacturer or spa dealer.

Figure 20:
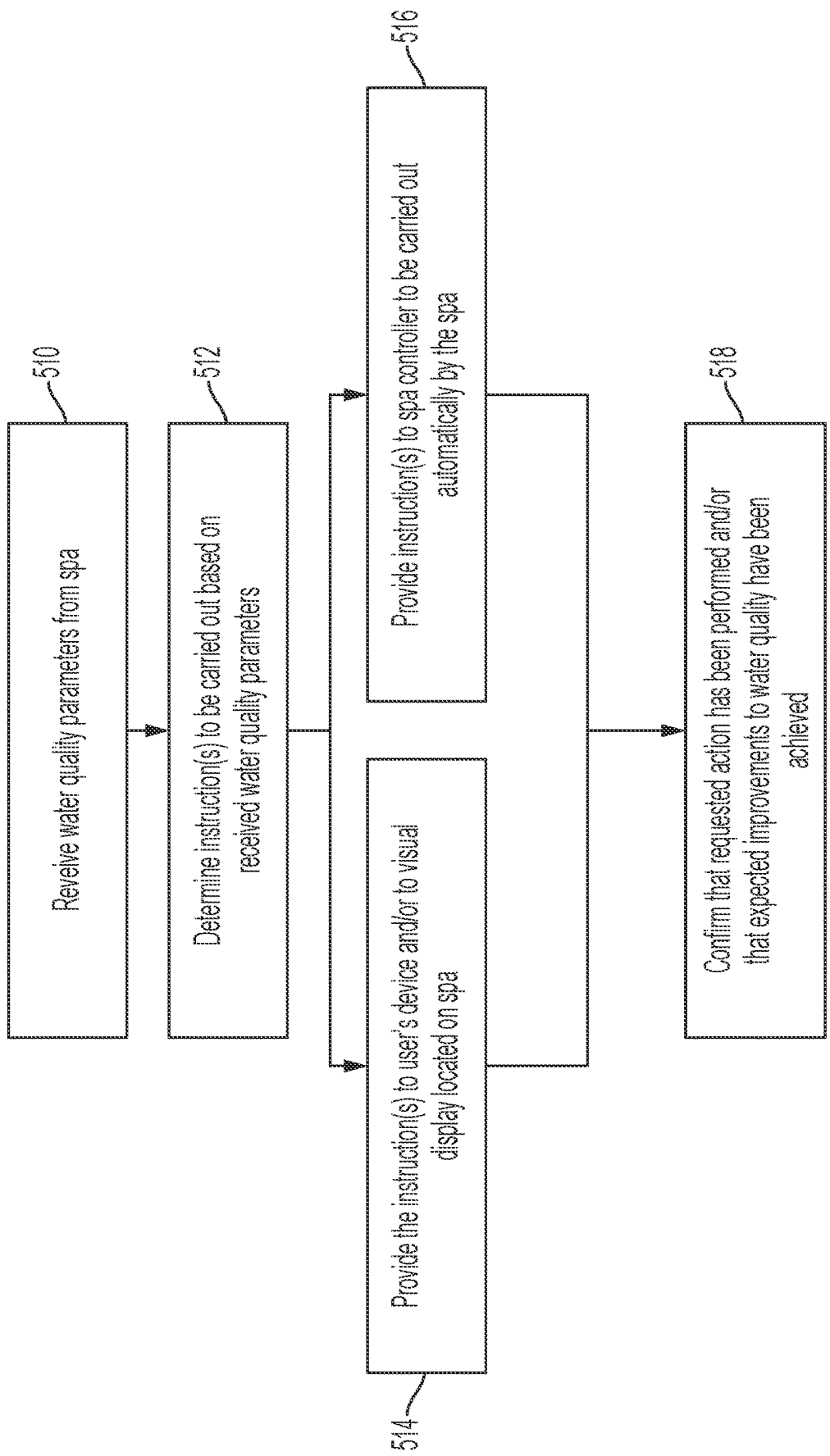
FIG. 20 is a flow chart for remotely controlling a spa to monitor and improve water quality.
Figure 22C:
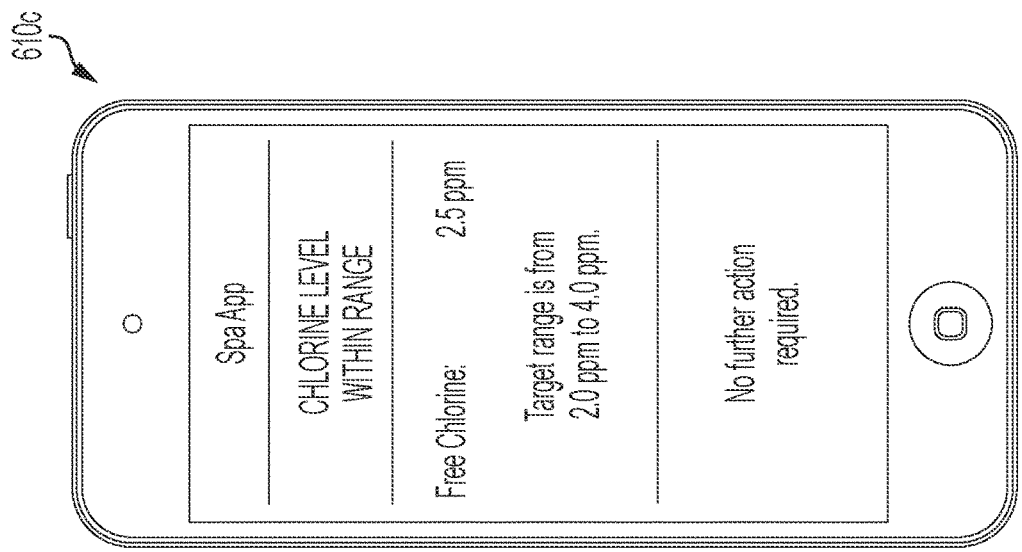
FIGS. 22A-22C are drawings of user interface screens shown on a portable electronic device for controlling a spa using the remote spa control system of FIG. 21.
Figure 22B:
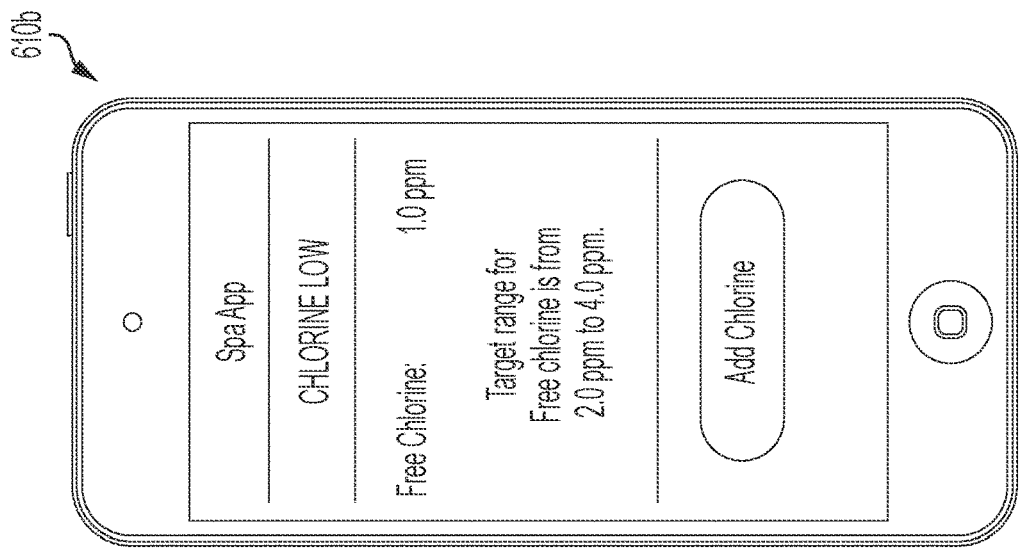
Figure 22A:
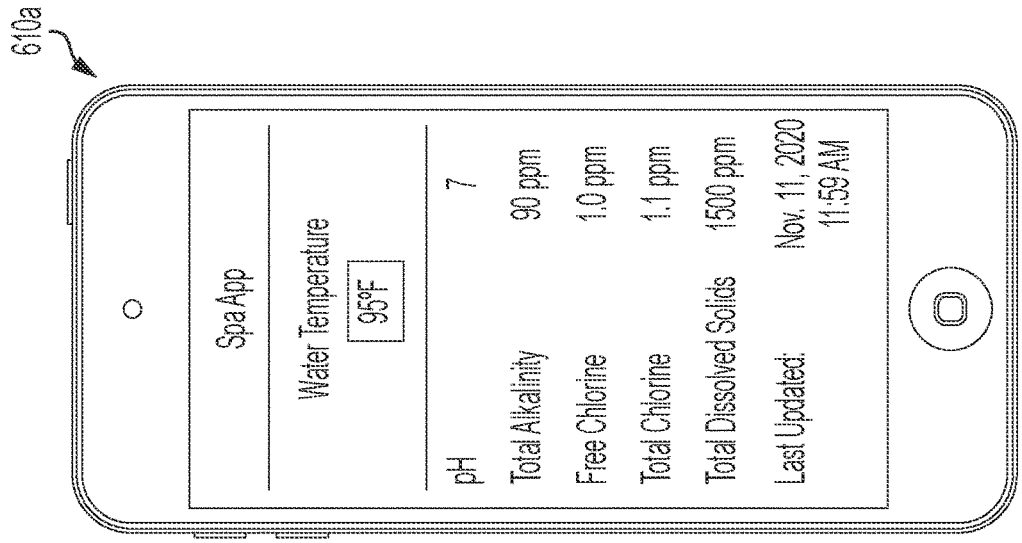

The remote processor 414 can be configured to perform various functions related to data received from the spa 1000 as shown in the flow chart in FIG. 20. For example, at step 510, the processor 414 can be configured to receive water quality parameters from the spa controller 1040 determined based on the sensed color and/or light intensity information provided by the sensor 128. As described previously, the water quality parameters can be calculated on the spa 1000 by the spa controller 1040 or by a separate controller or processor, such as a computer processor 232 contained in the housing of the water testing system of the spa. Calculated water quality parameters can include for example, acidity (e.g., pH), total alkalinity, free chlorine, total chlorine, or total dissolved solids. The processor 414 can cause the received water quality parameters to appear on a visual display of the user's portable electronic device 420, such as smartphone, computer tablet, smartwatch, or similar device, as are known in the art. An exemplary user interface screen 610a showing measured water quality parameters is shown in FIG. 22A.

At step 512, the processor 414 can be configured to determine an instruction to be carried out based on the received water quality parameters. In some examples, determining the instruction can include comparing the received water quality parameters to predetermined target water quality parameter values and/or to baseline values for the spa 1000 determined, for example, during manufacture of the spa 1000. If the received water quality parameters are within a range of predetermined target values or within a predetermined percentage of a target value, then the determined instruction may be to take no action. If the received water quality parameters for the spa 1000 are outside of the target range or differ from the target value by more than the predetermined percentage, then the determined instruction may include an instruction to perform an action to improve water quality.

In some examples, predetermined target water quality parameter values or target ranges can be updated or adjusted based on data sensed by the testing system or available to the processor. For example, the target water quality parameters may be determined or updated based, in part, on real-time measurements by environmental sensors of the spa 1000. The environmental sensors may measure, for example, ambient temperature, humidity, ambient light or ultraviolet light (e.g., to determine whether it is daytime or night), or other environmental parameters. In other examples, the processor 414 can include and/or be in electronic communication with a database 418 containing historical information about the spa 1000 and/or about the location where the spa 1000 is installed. For example, historical information can include water quality parameters previously received for the spa 1000, such as previous values for one or more of pH, total alkalinity, total chlorine, total dissolved solids, or temperature for the spa water. The information can also include historical information for environmental parameters and/or historical weather information for the location where the spa is installed. The determined instruction can be based, at least in part, on information in the historical database 418. For example, the processor 414 can be configured to analyze the information in the historical database, along with measured water quality parameter values to detect trends for the parameters over time. The determined instruction can be based, at least in part, on the identified trends.

At step 514, the processor 414 can be configured to provide the determined instruction to the user's portable electronic device 420 or to other devices for displaying information to the spa user, owner, and other parties. The determined instruction can include, for example, an instruction to add chemicals to the spa to improve water quality. In other examples, the instruction can be an instruction to turn on a pump, such as a pump of the spa circulation system, to filter the spa water. In some examples, the determined instruction is provided on the spa 1000 itself. For example, the determined instruction may be sent to the spa controller 1040. The spa controller 1040 can be configured to cause a visual display, such as a display on a control panel of the spa 1000, to display the instruction to the user.

In other examples, the determined instruction is provided to the user on the user's portable electronic device 420. The portable electronic device 420 can be configured to receive information from the remote processor 414 through the web portal 416 for viewing on a website or App accessible over a specialized computer network or the Internet. In some examples, the user may be able to perform some action on the portable electronic device 420 to confirm (1) that the instruction was received, and (2) that the instructed action was performed. In other examples, the user may remotely control the spa 1000 from the portable electronic device 420 to cause the spa 1000 to perform the requested action. For example, if the determined instruction is that additional chemicals should be added to the spa 1000, the device 420 may display a screen asking the user to confirm that the additional chemicals should be added to the spa 1000. Once the user confirms that the additional chemicals should be added, an instruction can be sent from the user's portable electronic device 420 to the spa controller 1040 through the web portal 416 and server 412. Upon receiving the instruction from the user's device 420, the spa controller 1040 can cause the chemical to be added to the spa water. An example user interface screen 610*b* that provides an instruction to the user and asks the user to confirm that the spa 1000 should perform the requested action is shown in FIG. 22B.

At step 516, in other examples, the processor 414 is configured to provide the determined instruction directly to the spa controller 1040 without requesting input from the user. If the measured water quality parameters are outside of the target range for water quality parameters, the instruction can include an instruction to activate a device or system of the spa 1000 to improve water quality. In that case, the processor 414 may generate and transmit a control signal to the spa controller 1040, which can be received and provided to the spa controller 1040 by the wireless transmitter 422. Once the control signal is received, the control signal can cause the spa controller 1040 to automatically activate a spa chemical and/or filter system, such as a chlorine generator device fluidly connected to the spa water circulation system, in response to the received instruction.

At step 518, the processor 414 can be configured to confirm that the instruction has been followed and, for example, that the requested action has been performed. The processor 414 may also be configured to confirm that the action achieved an expected or desired result. For example, the processor 414 can be configured to request updated water quality parameters from the spa 1000 at a predetermined time after the instruction is provided or after the user confirms that the instructed action has been performed. Upon receiving the updated water quality parameters, the processor 414 can be configured to compare the received water quality parameter to threshold values or to updated threshold values. A new instruction may be determined based upon results of the comparison. If the updated water quality parameters are within an acceptable range, the processor 414 may cause an indication of acceptable water quality to appear on the user's portable electronic device 420. An exemplary user interface screen 610*c* showing that the requested action has been effective and that water quality parameters are within the acceptable range is shown in FIG. 22C.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:
1. A spa tub, comprising:
  a spa shell defining an interior cavity configured to contain a volume of water;
  at least one spa circulation pump in communication with the interior cavity of the spa shell, the at least one spa circulation pump being configured to create a flow of the water to and from the interior cavity of the spa shell; and
  a testing system configured to acquire water samples from the volume of water and perform water quality tests on the water samples, the testing system comprising:
    a housing;

a testing system circulation pump disposed within the housing, the testing system circulation pump being configured to acquire the water samples from the volume of water;

a replaceable reagent cartridge removably received within the housing, the replaceable reagent cartridge comprising at least one pouch for containing at least one chemical reagent;

a test plate assembly disposed within the housing, the test plate assembly being configured to receive the water samples acquired by the testing system circulation pump and the at least one chemical reagent from the reagent cartridge, wherein the test plate assembly is configured to mix the water samples and the at least one chemical reagent and perform the water quality tests on the mixed water samples and the at least one chemical reagent; and a discharge filter disposed downstream of the test plate assembly, the discharge filter being configured to at least partially remove the at least one chemical reagent from the water samples after the water quality tests are performed.

2. The spa tub according to claim 1, wherein the test plate assembly comprises a cartridge receiving portion and a reusable test portion.

3. The spa tub according to claim 2, wherein the reusable test portion comprises at least one reagent dispenser for accessing the at least one reagent in the at least one pouch and distributing the at least one reagent within the reusable test portion.

4. The spa tub according to claim 3, wherein the at least one pouch comprises a sealable closure at an end thereof and the at least one reagent dispenser comprises a needle configured to extend through the sealable closure to access the at least one reagent.

5. The spa tub according to claim 3, wherein the reagent cartridge and the cartridge receiving portion are configured to align the at least one reagent pouch with the at least one reagent dispenser, and wherein the cartridge receiving portion comprises at least one recess defined therein aligned with the at least one reagent dispenser and the at least one pouch comprises a spout projecting from the reagent cartridge, the spout of the at least one pouch being configured to be received in the at least one recess in the cartridge receiving portion to align the spout with the at least one reagent dispenser.

6. The spa tub according to claim 1, wherein the reagent cartridge comprises a plurality of vent openings defined therein to allow cooling air to flow through the cartridge to maintain a temperature of the reagent.

7. The spa tub according to claim 1, wherein the testing system further comprises a testing system main pump configured to draw a portion of the volume of water through the testing system, the testing system main pump being disposed downstream of the test plate assembly.

8. The spa tub according to claim 7, wherein the testing system circulation pump within the housing is configured to acquire the water samples from the portion of the volume of water drawn by the testing_ system main pump.

9. The spa tub according to claim 1, wherein the test plate assembly comprises:

a base plate comprising a top surface, a bottom surface, and a peripheral edge extending therebetween;

a mixing chamber on the base plate comprising a water sample port, a reagent port, and a drain port;

a sensor on the base plate configured to detect light transmitting through or reflecting from the mixing chamber; and a fluid circuit on the base plate for providing the water samples to the mixing chamber through the water sample port, for providing a dose of the at least one chemical reagent to the mixing chamber through the reagent port, and for conducting a mixed sample from the mixing chamber through the drain port after testing, the fluid circuit comprising:

an inflow portion comprising at least one conduit extending between a plate inflow port and the water sample port of the mixing chamber;

a reagent portion comprising at least one conduit extending from at least one plate reagent port to the reagent port of the mixing chamber;

a drain outlet portion comprising a conduit extending from the drain port of the mixing chamber to a plate drain port; and at least one pump mounted to the base plate for moving the water samples, dose of the at least one chemical reagent, and/or mixed sample through the portions of the fluid circuit.

10. The spa tub according to claim 9, wherein the at least one pump comprises a peristaltic pump configured to contact a flexible portion of one of the conduits of the fluid circuit to move the water and/or the reagent through the conduits.

11. The spa tub according to claim 9, further comprising a light source for projecting light through the mixing chamber, the light source comprising a broad spectrum white light source, wherein the mixing chamber comprises a conduit arranged in a serpentine path on the top surface of the base plate, the serpentine path comprising multiple substantially straight segments connected by curved segments, and wherein the light source is configured to shine light through the multiple substantially straight segments of the serpentine path, and wherein the sensor measures an intensity of light passing through the multiple substantially straight segments.

12. The spa tub according to claim 9, wherein the fluid circuit further comprises a reagent input valve positioned on the reagent portion between the plate reagent inflow port and the reagent port of the mixing chamber, the reagent input valve having an open state in which the at least one chemical reagent from the reagent cartridge passes through the reagent input valve toward the mixing chamber and a closed state in which the at least one chemical reagent is prevented from passing through the reagent input valve, and wherein a volume of a conduit extending between the reagent input valve and the reagent port of the mixing chamber is a predetermined volume for a dose of the at least one chemical reagent to be used for a water test being performed.

13. The spa tub according to claim 9, wherein the fluid circuit further comprises a mixing loop portion comprising at least one conduit extending between the water inflow portion and the reagent portion for flushing the at least one chemical reagent from the reagent portion into the mixing chamber, and wherein the mixing loop portion further comprises at least one mixing loop valve configured such that, when in an open state, the water samples flow from the mixing chamber, through the mixing loop portion, and reagent portion back to the mixing chamber, and when in a closed state, the water samples are prevented from passing from the mixing loop portion to the reagent portion of the fluid circuit.

14. The spa tub according to claim 9, wherein the water test assembly comprises multiple test plate assemblies, and wherein the testing system further comprises a motor configured to operate the at least one pump of each of the test plate assemblies.

15. The spa tub according to claim 9, wherein the fluid circuit of the at least one test plate assembly further comprises at least one valve for preventing the water samples from flowing through conduits of the fluid circuit to control delivery of the water sample and/or reagent to the mixing chamber,
wherein the testing system further comprises a valve actuator plate operably connected to a motor of the water testing system by a cam assembly,
wherein the base plate is mounted to the valve actuator plate, and
wherein movement of the valve actuator plate opens and closes the at least one valve of the test plate assembly.

16. A spa tub, comprising:
a spa shell defining an interior cavity configured to contain a volume of water;
at least one spa circulation pump in communication with the interior cavity of the spa shell, the at least one spa circulation pump being configured to create a flow of the water to and from the interior cavity of the spa shell; and
a testing system configured to acquire water samples from the volume of water and perform water quality tests on the water samples, the testing system comprising:
a housing;
a testing system circulation pump disposed within the housing, the testing system circulation pump being configured. to acquire the water samples from the volume of water;
a replaceable reagent cartridge removably received within the housing, the replaceable reagent cartridge comprising at least one pouch for containing at least one chemical reagent;
a test plate assembly disposed within the housing, the test plate assembly being configured to receive the water samples acquired by the testing system. circulation pump and the at least one chemical reagent from the reagent cartridge, wherein the test plate assembly is configured to mix the water samples and the at least one chemical reagent and perform the water quality tests on the mixed water samples and the at least one chemical reagent; and
a thermoelectric cooler configured to maintain a temperature of the reagent cartridge.

17. The spa tub according to claim 16, wherein the testing system further comprises a testing system main pump configured to draw a portion of the volume of water through the testing system, the testing system main pump being disposed downstream of the test plate assembly, and
wherein the portion of the volume of water drawn through the testing system by the testing system main pump is directed through the thermoelectric cooler and the thermoelectric cooler is configured to transfer heat from an interior of the housing of the testing system to the portion of the volume of water directed through the thermoelectric cooler.

18. The spa tub according to claim 16, wherein the testing system further comprises a discharge filter disposed downstream of the water test assembly, the discharge filter being configured to at least partially remove the at least one reagent from the water samples after the water quality tests are performed.

19. A water test device for a pool or spa for testing water from the pool or spa using one or more fluid reagents, the test device comprising:
a base plate comprising a top surface, a bottom surface, and a peripheral edge extending therebetween;
a mixing chamber on the base plate comprising a water sample port, a reagent port, a drain port, and a conduit arranged i.n a serpentine path on the top surface of the base plate between the water sample port and the drain port, the serpentine path comprising multiple substantially straight segments connected by curved segments;
a sensor on the base plate configured to detect light transmitting through the multiple substantially straight segments of the serpentine path to measure intensity of light passing through the multiple substantially straight segments of the conduit of the mixing chamber; and
a fluid circuit on the base plate for providing the water from the pool or spa to the mixing chamber through the water sample port, for providing a dose of a reagent to the mixing chamber through the reagent port, and for conducting a mixed sample from the mixing chamber through the drain port after test, the fluid circuit comprising:
an inflow portion comprising at least one conduit extending between a device inflow port and the water sample port of the mixing chamber;
a reagent portion comprising at least one conduit extending from at least one device reagent port to the reagent port of the mixing chamber;
a drain outlet portion comprising a conduit extending from the drain port of the mixing chamber to a device drain port; and
at least one pump for moving the water from the pool or spa, reagent, and/or mixed sample through the portions of the fluid circuit.

20. A method for testing a water sample from a pool or spa with a water test device in fluid communication with water contained in the pool or spa, the method comprising:
connecting a water test device to a water circulation assembly of the pool or spa for providing water from the pool or spa to the water test device, wherein the water test device comprises: a base plate comprising a top surface, a bottom surface, and a peripheral edge extending therebetween; a mixing chamber on the base plate comprising a water sample port, a reagent port, and a drain port; a sensor on the base plate configured to detect light transmitting through or reflecting from the mixing chamber; and a fluid circuit on the base plate for providing the water from the pool or spa to the mixing chamber through the water sample port, for providing a dose of a reagent to the mixing chamber through the reagent port, and for conducting a mixed sample from the mixing chamber through the drain port after testing;
introducing the reagent to the water test device from a reagent source by (i) opening a reagent inflow valve positioned on a reagent portion of the fluid circuit so that reagent from the reagent source flows into a reagent dose conduit of the reagent portion of the fluid circuit and so that excess reagent passes through the reagent port into the mixing chamber and (i) trimming the excess reagent from the mixing chamber by flushing the mixing chamber with water from the pool or spa, wherein a volume of the reagent dose conduit between the reagent inflow valve and the reagent port of the mixing chamber corresponds to a volume for the dose of reagent for the water test being performed, in combination with the remaining features and elements of the claimed invention;

introducing the water of the pool or spa to the water test device;

causing the reagent dose of the introduced reagent and a sample of the water from the pool or spa to mix together thereby providing the mixed sample in the mixing chamber of the water test device;

measuring color and/or light intensity for light shown through or reflected from the mixed sample in the mixing chamber with the sensor of the water test device; and determining, with at least one computer processor, water quality parameters for the water sample based on the measured color and/or light intensity.

* * * * *

UNITED STATES PATENT AND TRADEMARK OFFICE
CERTIFICATE OF CORRECTION

PATENT NO. : 11,833,517 B2
APPLICATION NO. : 17/097153
DATED : December 5, 2023
INVENTOR(S) : James Edward Szpak et al.

It is certified that error appears in the above-identified patent and that said Letters Patent is hereby corrected as shown below:

In the Claims

Column 47, Line 61, Claim 8, delete "testing__" and insert -- testing --

Column 49, Line 9, Claim 15, delete "claim 9 ," and insert -- claim 9, --

Column 49, Line 36, Claim 16, delete "configured." and insert -- configured --

Column 49, Line 44, Claim 16, delete "systern." and insert -- system --

Column 50, Line 11, Claim 19, delete "i.n" and insert -- in --

Signed and Sealed this
Thirtieth Day of January, 2024

Katherine Kelly Vidal
*Director of the United States Patent and Trademark Office*